US011890336B2

(12) United States Patent
Wren et al.

(10) Patent No.: US 11,890,336 B2
(45) Date of Patent: Feb. 6, 2024

(54) ***FRANCISELLA* GLYCOCONJUGATE VACCINES**

(71) Applicant: London School of Hygiene and Tropical Medicine, London (GB)

(72) Inventors: Brendan Wren, London (GB); Jon Cuccui, London (GB); Madeleine Moule, Bryan, TX (US)

(73) Assignee: London School of Hygiene and Tropical Medicine, London (GB)

(*) Notice: Subject to any disclaimer, the term of this patent is extended or adjusted under 35 U.S.C. 154(b) by 519 days.

(21) Appl. No.: 17/098,809

(22) Filed: Nov. 16, 2020

(65) Prior Publication Data

US 2021/0069312 A1 Mar. 11, 2021

Related U.S. Application Data

(62) Division of application No. 16/326,642, filed as application No. PCT/GB2017/052653 on Sep. 11, 2017, now abandoned.

(30) Foreign Application Priority Data

Sep. 12, 2016 (GB) ..................................... 1615427

(51) Int. Cl.

| | |
|---|---|
| ***A61K 39/00*** | (2006.01) |
| ***A61K 39/02*** | (2006.01) |
| ***A61K 47/64*** | (2017.01) |
| ***A61P 31/04*** | (2006.01) |
| ***C07K 14/195*** | (2006.01) |
| ***C12N 15/74*** | (2006.01) |

(52) U.S. Cl.

CPC ........ *A61K 39/0208* (2013.01); *A61K 47/646* (2017.08); *A61P 31/04* (2018.01); *C07K 14/195* (2013.01); *C12N 15/74* (2013.01); *A61K 2039/55566* (2013.01); *A61K 2039/55572* (2013.01); *A61K 2039/575* (2013.01); *A61K 2039/6037* (2013.01); *A61K 2039/6068* (2013.01); *A61K 2039/70* (2013.01); *C07K 2319/40* (2013.01)

(58) Field of Classification Search

CPC .................................................. A61K 39/0208

See application file for complete search history.

(56) References Cited

U.S. PATENT DOCUMENTS

| | | | |
|---|---|---|---|
| 4,601,903 | A | 7/1986 | Frasch |
| 9,642,902 | B2 | 5/2017 | Wren et al. |
| 2020/0054732 | A1 | 2/2020 | Wren et al. |

FOREIGN PATENT DOCUMENTS

| | | | |
|---|---|---|---|
| WO | WO 2009/104074 | A2 | 8/2009 |
| WO | WO 2014/114926 | A1 | 7/2014 |

OTHER PUBLICATIONS

Cuccui and Wren, "Hijacking bacterial glycosylation for the production of glycoconjugates, from vaccines to humanised glycoproteins," *J Pharm Pharmacol. 67*:338-350, 2015.

Cuccui et al., "Exploitation of bacterial N-linked glycosylation to develop a novel recombinant glycoconjugate vaccine against *Francisella tularensis," Open Biol. 3*:130002, 2013.

Hug er al., "Exploiting Bacterial Glycosylation Machineries for the Synthesis of a Lewis Antigen-containing Glycoprotein," *J Biol Chem. 286*:37887-37894, 2011.

Lehrer et al., "Functional Characterization and Membrane Topology of *Escherichia coli* WecA, a Sugar-Phosphate Transferase Initiating the Biosynthesis of Enterobacterial Common Antigen and O-Antigen Lipopolysaccharide," *J Bacteriol. 189*:2618-2628, 2007.

Valderrama-Rincon er al., "An engineered eukaryotic protein glycosylation pathway in *Escherichia coli," Nat Chem Biol. 8*:434-437. 2012.

PCT/GB2017/052653 International Search Report and Written Opinion dated Jul. 3, 2018 (21 pages).

*Primary Examiner* — Albert M Navarro

(74) *Attorney, Agent, or Firm* — Klarquist Sparkman, LLP

(57) ABSTRACT

The disclosure relates to a glycoconjugate vaccine conferring protection against *Francisella tularensis* infections and a method to manufacture a glycoconjugate antigen.

18 Claims, 24 Drawing Sheets

Specification includes a Sequence Listing.

| Conjugate ID | total protein produced from 2L (µg) |
| --- | --- |
| DnaK-FT | 9519.7 |
| IglC-FT | 5851.4 |

Figure 3 (SEQ ID NO: 2)

MGKIIGIDLGTTNSCLAIMDGKTAKVIENAEGHRTTPSVVAYTDSGEILVGQAAKRQAVT
NPDNTFFAIKRLIGRKYDDKAVQEDIKKKVPYAVIKADNGDAWVATKEGKKMAPPQVSAE
VLRKMKKTAEDYLGEPVTEAVITVPAYFNDSQRQATKDAGKIAGLEVKRIINEPTAAALA
YGVDSKKGEQTVAVYDLGGGTFDISIIEIADVDGDNQIEVLSTNGDTFLGGEDFDLALMN
YLIDEFKKEQGIDLHNDKLALQRVREAAEKAKVELSSAQQTDVNLPYITADATGPKHLNI
KVTRAKFESLVSDLVMRSLEPCKKALEDAGLSKSDITEVLLVGGQTRMPLVQEKVKEFFG
KEPRKDVNPDEAVAVGAAIQGGVLAGDVKDILLLDVTPLSLGIETMGGVMTKLIERNTTI
PTKKSQVFSTAEDNQPAVTIHVLQGEREMASANKSLGRFDLADIPPAPRGMPQIEVTFDI
DANGILNVSAKDKATGKEQNIVIKSSSGLSEEDIEKMVQDAEANAEADKKFHDLVTARNT
ADNLIHSSRKAIQELGDKVTAAEKEKIEEACKELEAATKGDDKQAIESKTKALEEAFAPI
AQKAYAEQAQAAVAQGGAKAEEPKKEEDVVDADFEDVEDDKK

Figure 4 (SEQ ID NO: 1)

MIMSEMITRQQVTSGETIHVRTDPTACIGSHPNCRLFIDSLTIAGEKLDKNIVAIDGGED
VTKADSATAAASVIRLSITPGSINPTISITLGVLIKSNVRTKIEEKVSSILQASATDMKI
KLGNSNKKQEYKTDEAWGIMIDLSNLELYPISAKAFSISIEPTELMGVSKDGMRYHIISI
DGLTTSQGSLPVCCAASTDKGVAKIGYIAAA

Figure 5A (SEQ ID NO: 8)

TTAACTACTTGTATCTAGTCTAACAATATCGTCTTCACTTATATATTCTCCAACTTGTAC
TTCTATAAGAATAACTGGAATCTTGCCATTATTTTCAAGTCTGTGAGATTCGCCTATTTT
TATATATACAGACTCATTTGGTCTAACAATAGACTTAGTAGTACCAATAGTTACCGTAGC
AGTTCCAGAAATCACAATCCAATGCTCACTACGGTGATAATGTTGCTGTAATGATAACTT
CTTGCCCGGTTCAAGTTGAATCGCCTGTATCTTATAACCAGACTTATCCTCTAATATTGT
CGCTGAACCCCAAGGTTTATAAATTTGCTTATGCTGTAATAATTCACTTCGCTGCTGAAT
TTTCAAAACTTCGACTATTTTTTTGACATCTTGAGTTTTGTTCTTATCCGCGACAAGTAT
AGCATCTGCTGTTTCAACAATTATTAAATCATTAACTCCGACTGCAGCCAATAAACGATC
ATGCGAGCGTAAATAACTATTTTTGACATTACTAGTAATCACATCGCCAATAACCACATT
ACCACAACTATCTTTTGCAGCAATATCATACAAAGAGTCCCAAGAGCCAACATCAGACCA
GCCACTTTGTTGCATAGGCACTATAGCAACATTAGTTGCTTTCTCCATAACTGCGTAGTC
TATTGACTGTGATTGAACTAGGGCAAAGCTTTGTTTATCAAAACGCACAAAATCTAAATC
CTGCTGTGACTTTTGATAAGTTTTTTCACATCCTCTGTAAATCTCTGGCTGTAACTTCTC
TAAAACCTCTAAATACACTCTAGCTGTGAACATAAACATACCGCTATTCCAATAGTATTT
GCCACTATCTAAATACTCTTGTGCAACGACCACACTAGGCTTCTCAACAAATTTATCTAC
CTTATAAACTCCATTTACAGTAGTCTGTACCCCTTGTTTAATATAACCATAGCCTTCATG
AGGACAAGTTGGTGTAATGCCAAAGGTAACTAAAGAATCATCTTTAATAACTTTTTGCTG
TGCTTTTTCGATAGCTTGATGAAAAATCTCCAGATTTTCAATATGATGGTCAGCAGCTAA
AACTAGCATAATTGTATTTGGATCATTAATAGCTAAATGTAGTGCTGCAAGTGCAATTGC
TGGAGCAGTATTTCTGGCTAATGGCTCTAGGAGTATATCGCCTTTTTTATTGATTTTCCG
CAACACTTCAGCAACTTGGAATCTATGACTTTCATTACAGACAACTACAGGTGAAGTTAT
ATCCTTGACATTATCTAGTCGCTTAATTGTATTTTCTAATAGACTATGTTCATCAACCAA
GCCGATAAACTGCTTTGGCGATGCCTCTCGTGATAGTGGCCATAGCCTTGAGCCGAATCC
TCCAGATAAGATAATAGGAGTAATCATTATAAAAACCTAAATAACTTTGATATTGATTAA
TTATATAGAAAGCTAATATATTCAACAATAAATCAGCAAATTAAATATTGTCATAACTTA
ACTTACTAAATTTAGATAGTAGGTTTATAATAGGATCTCTAAAAATTACCTTTGTATGTT

Figure 5B

TGTTTAGATAATATTTGTAGCAAACCTTATACAAAGTAGAGCATCATTATGTCAGTTTTG
ACCAGAGAATACCAAGAATATTTTAGCAGCATGATATAGTTAATCCGAGAGTATTTTGTT
AAACACATAAGAGATAGCATCACAAAATTTTTCAAAACTATTATTCACTTTTCTAAATAT
TTTTTTAATAGTTAGCCCAAACCTTTTCAATAGGATTTAAATCTGGAGAGTACGGAGGTA
GATATAATATTTGTACATCAAATTTATTGGCTATTTCTTTTAGTTTTTCTATATACTCCA
ACCTTTCATGTTCTTTTCTTTGCTTATATTTTGGAGTCTTTTTTTAAAACTAAAACCAAG
TCTATTAAGACAATCATAAAATGTACTTCTTGGAATATCAGGGGCTAATGCTTCTTTTAT
ATCTAATGCACTTGCATCTGGATGATCTATCAAATACTGTTCAATCAATGTTTTATCGGT
AAAGCTAGCGACTCTGCCACAACCAACTCCTTGCTTTGAACTATAATCTCCGGTTCTTTT
ATAAAACTCTATCCATGAAACAACTGTACGCTTATCTATGTTAAAAAACTTACTCAGCTC
GAACTCCGTCATACCTTCTTCATGTTTATTAATTACGATGTCTCTAAAATCTTGGCTATA
TGATGGCATTTTTATTAGACATTATAACATTTCTACAAATATCTTTTTCTACAAATATCT
TTCGGATTAACTATATTCTTGCGAACACTACTTTTTAACACAAAAATAAATTAAATTGAT
TTTTTAGAGATACTCATAAGATAAATATTTAAGCTATAGATAAAACTCAATAGTTTGTCT
AAACATCTTATCAAAATCTTGTGATGGCTTCCATCCTAACTCATTCTGAATCTTGCTGTT
ATCAATAGCATAACGCCAATCATGTCCTTTTCTATCTTCCACAAATGTGATTAAGTTAGA
ATGTGGAGCATTTTCTGGTTTATATTCATCCATTAGTTTACAGATAGTTTTTACCAAGGT
TAGATTATCAACTTCATTAATACCACCAATATTATAAACCTCTCCAACCACTCCTTTCTC
AACAATTGTCTGGATAGCATCGCAGTGATCTTCTACATATAGCCAATCTCGAATATTCGA
ACCATCTCCGTAAACAGGAATAGGCTTGTAGTTTATACAACTATTTATCACTACAGGGAT
TAATTTCTCTCGATGTTGGTATGGTCCATAGTTGTTTGAACAATTTGAAATTGTTACCGG
AAGTTTATAGGTATGATGATATGCTCTAGAAATATGATCAGATCCCGCCTTAGATGCCGA
ATACGGTGAATTTGGCTCATAAGCCTTAATCTCAGTAAAGGCTGGTTCATCTTTTGCCAA
GGTACCATATACCTCATCAGTAGATACATGATGAAACCTACAACTAGTTTCTTCTAAACC
TAGCTCATCTAACCAATACCTTTTAGCACAATCTAAAAGTGTAAATGTACCTATCACATT
CGTTTCTAAAAATACCTTTGGATTAGCAATTGAATTATCAACATGCGATTCTGCAGCAAA
ATGTACTATCGTATCAATTTTATATTCTTTCAGTGTTTGATATACTAAAACTTCATCACA
AATATCACCTTTTATAAAAGTATGGTTATGTTCATTATTCAAGTCTTTTAGATTATCTAA
ACTACCCGCATAAGTAAGCTTATCATACGAGATTATTTTGATATCACTATAGCGTGATAA
CATCATACGCACATAGTTACTACCAATAAATCCCGCCGCACCTGTTACTAGGATATTTTT
TGGTTTGTAGTTCATTTTTTCATTCCTCATTACATCATCATTCCTATAGTGACTAGTCAT
TCTCTCACTAAACTATCATTACCGCATAAACTTGTCATTACCGCGTAGGCGGTAATCTCC
CAATCACATCTGATATTTAGAGATACCTATCTGCACCAGTAAGACAAAAGTTTTACTCAC
ATATTAATTCATATAAATCATTCCAATTCGGATTCATCTCATTAATAATTCGTTCTTTCC
AAGATCTGTTTCATTTTTTCAACTGCTTTTCTCACAGAATTGCTGCTTTTATATCTTCAT
AAATTTCAAAATAAACTAACTTATTAACATTATATTTTTAGTAAAACCATCTGCAAGGCT
ATGTTTATGCTCATACATTCTTTTTATCAAATTAGATGTTACAACTATGTACAGAACAGT
ATTATCCTTATTTGTAAGAATATACATAAAACCATTTTTAGTCATTGTAAAACATCGCTA
TATATTACCAAACCTGTCATTACTGCGCAGATTGGAATCTCCAAAACATATCCAACTTTT
ATGAGATACCCACCTTCATGGGTATGACGGATTAATTTATAAACCATCCTTAATTAAATT
CTTCAGATACTGACCATACTCTGTCTTAGAAAGTTTTTCAGCTTGAGCTAGAACTTGTTG
TGTTGAGATAAAGCCTTTACGCCATGCAATTTCTTCCAAACATGCAATTTTAAGCCCTTG
TCTTTTCTCAATAGTTGCGACATATTGACCTGCCTCTAGCAATGAATCATGCGTACCAGC
ATCAAGCCAAGCAAAGCCACGCCCTAAGAGTTCGACATTTAGCTTATTTTCTTTTAGATA
TAACTCATTAAGTGAAGTAATCTCTAGCTCACCACGTGCAGATGGTTTGACTTGTTTAGC
ATACTCAACAACATTATTATCATAAAAATATAAACCTGTGATAGCATAGTGTGACTTAGG
ATTCTGTGGCTTTTCCTCTACCGAAATTACATTTTTTTGCTTATCAAATTCGACTATACC
ATATCTATGCGGATCATTAACATAATAACCAAAAACACAAGCGCCACCAGCTGGACCTCC
ACACTGTGCTCTTGCAGACTCTAGCATTGTAGTCATACCTTGACCATAGTAGATATTATC
TCCTAATATCAAACAAGCTGAGTCACCCGCCAAAAACTCCTCACCAAGAATAAATGCTTG
AGCAAGCCCATCTGGTGATGGCTGGATTTTATAACTCAACTGTATACCAAATTGTGAACC
ATCACCAAGAAGCTCTTGGATAAGTGAGATATCACGCACTGTAGAGATAATTAATATCTC

Figure 5C

CCTAATACCTGCAAGCATAAGCACAGATAGTGGATAGTATAACAATGGCTTGTCATAAAC
AGGTAGCAGCTGTTTGCTAACACCCAAGGTAAGTGGATATAGCCTTGTACCACTGCCACC
AGCTAGAATTATTCCCTTCATTTCACATAATCCTCTAAATGATATTTATTTTTCAAATCT
ATATTTAAACCAACTTACTAATGGAATACATCTTGATCTAATTAAAATTTTGAATAGACG
AATAGCACTAATAAAACATCTCCCTTTAATAGCCGAAATTATCATTTGCACAACAGGGAT
ACAAATATTTAATTTCTCTTCAGGATATCTATCCAAAAAATATTCAAATAATCCAGCATA
AGTATTATAGATTTTTTCCTTAGACTTAGATGTGATACCAATACCTTTTCTGTACACACT
ATAGGATTCATTAGAATTTAAAAAACTTAAATAACCTTTTTCTGCTGTTATAACATGAAA
ATAATAATCTAGAAGCTCTATATCCGGTAAAATCAAATCATCCAAAACCGATGTTCTGAA
CATTTTTGAACTATTTGCACCAACAGCAACTCCGCGTAAAGTGTCTGATAAATTGAATAT
ACTCTTATTTGAACAAGCAAACCTACTATGTTGTATATTACCATTTGGATAGAGTATATT
TATATTATGAAAAACTCCCGTACATCTTGGATTATTATCCAAAAAATCAGCCTGAATTTG
AAGTTTACCAGGCAATGCATAATCATCACCATCCATATGAGCTATATACTCACCATTTGC
AACAAAATAGATTTCTTTAATATTTTCAGTAATTCCCACATTCTTATCTCTAAAAACTGG
CTTTATGATATCCGGATACTTTTTTTGATACTCTTGAATAACATCTCTTGTACCATCTGT
AGAAAAATCATCTCCAACGATTATCTCAAAGTCAAAATCAGTCTCTTGAGTAACCAAAGA
CTCTAAACATTGACCAATATACTTTTCTTGATTGTATGTCATCACACATACTGAAACTTT
AATCATCTATACACCTCAAAACCTTGTACCGAAACAAAACATACTCTATACAAATTTGTA
TAAATAAAAATGCAAACCCAATCAATATTAATTCTACCAACCCAATTTTACTTGGATAAA
TATACCAACCCTTAAATATTAACGATAATAAAAAACATACTATAGTAATAACTGCTAAAT
TTATAAAAAAATACCTATTGATACCTTTAGCAAATACATGGTGTACAATAGGCATCCAGA
TTATCAGCCCCACTATAGCATATCCAAGCCATAATAGTGCTGTAGTATACACTCCATAAT
TATAAGCAGTATATATAACTATAGGAGCAAAAAATACTAAACTAATTGTATTATATGTAT
TATGTAGCTTTAACTTACCATAAGCATACTGTAAAAAATATTGAAATGATATTATACAAA
TAATAGATGCTGATAAAACATATATATTTAAGATATTACTACCCCAATTAGCAATTTCCA
TACTTCCTGTCCATGACTGCAACAGCTGATGAGAATACATCAAAACACATGTTACTACAG
CAGATAAAAAAGTAATTGAGATCAAGGATGATTTTAAATATAAGCTTTCCATTCCTTTTA
CATTTTGTTGGGCTAATAGCATTGTCATTCTAGGCTGAATAGCTATGCTAATCGGAGAGG
ACAATATCGTAACAGCACTAGATATCACTATCAATAAAGATAAATAACCATACTCAGATA
ATGGTAATACATGTGAGAACACTAATTTATCAGATTGAGTGACAATAATCCAAACTGTTG
TAGAATATGCAATGCCTAGTGCAAATGGAAGCACTTTTCTAATTATTTTAAAATCAAACC
TTAAACCCACGCTAAATGATGATGGTAGTATTTTATAAAATGCAATTGCAATACATACTA
GATATAGTATCGCAATTATTGTCTGATATACAAAATAATACATAATATTAGTAGACACAT
AGCAGATAAATAATAATCCACCAATAAACTGTAGTGTCGTTTGTATGATACTTAAATTAT
TATAAAGAACCTGTCTTTCAAAGCCACGCAAACCACCACCATATAGATCAGACACCCATC
TTAATGCAAACATTAAACCCATAAGTGCAATACATACACTTACACTATCAGCATCTAGCG
AGCCTATATGTAACCAAGAGGTGGATATATACCTTGAATGTGTACTAATTACAATAAATA
CCAGAACACCAACAATAATGAAAAATAGCTCTAACGATCTAACCAACTTGCGTAAGTAAT
GATAGTCATCAGTACTACCTCTAACATGAGCCACTTCTCTTGATAAAGTTGGTGTTATAC
CAACATCCAACAACCGTAACCACGTTTGAAAAACTGTAAAAAAACCAATCAGACCAAATG
CATCATGACTTAAATGTTGTAAATACAAAGGAAGTATAACAATACCAATTAAGCTAGTAT
ATAGTTGTGTTATATAATTTGATATTGTATTTTTTTAAGGCTCATTTTTCTAACTTATC
TTTTCAAGTTCAAGAGCAACAAATACTTTATTTCCATGCTCATCAATGAAATAACTATTT
TTATATGGAGGGTGTGTCATAGCCCTTAGATAGTCAATTGCTTCCCGCATTGTTACTATT
TTATCTAAATCAATTTCACACATGTTTTTATAATCATGAATTGAATTATAGTTGCCTTCG
GAGTTAGGTTTGATTCGAGTGAACTTATTATTCAAAATATCATCTATGACTTTAGTGAAC
AACTCAACTTCTTTTTTTTGAACTTTAGCATAAACATCAAAAGAGTTTTCGAAAGAATTA
ACTTCAACTTCTTCCTGAATGATTATATCTCCATGATCTATCTCTTCATCCATCACATGA
ATAGTTGCTCCTATAGGTAGTTTATTTATAATAGAGAAGACCTGTGGAAACCACCCTCTA
TTATATGGATTAAGTCCAGGATGAATATTTATACATAATACTGAATTAACTAATTTTGCT
GGAAATAATTGTTTCGAATGACAAGAAAAACCTAAATCATACTTACCAATAAGATCATTG
CCATTTTTTTTCATATCTATTGGCTTAATCTCACTGTTATATATTTCTTTGGCAAAAGAA
GTTTGACTCTTGAAACTACAAAAATAATCAACCTCTACATCATTTTTACTACCAATGATA
TTTTTAAAATCACTTAGAATAGTTCTATTATCTGTAACAACAAATATTTTTTTCATGAGG

Figure 5D

AAACCTCTTTGATATTATTAATTATTTTATTAATTTTATCGTCTTCTAACTCTGCATAAA
TTGGCAAACATAATATTCTTTTAGATATATCTCTTGAGATTGGCATATACTGCTTTGGCT
CTATATAACTAAGACTATCTAATGATGGATAAAAATATCTACGCGATATTATATCATTTT
GTATTAGTGCTTTCTGTACTCTGAGAAGTTCCTCCTCAGTCCTAAATATTACTGGAAAAT
AGCTATAATTCCTACTAGAATGCTGATTCTGTTCTTGAAACTTTACCAATCCATCTAACC
CAGCCTCATATATCTCTGTAATAACTTTCCTTTTGCTCTTAATTTCTATAATATCATCTA
GAACACAAAGTCCCATAGCCGCCTCAAATTCATTCATTTTAGCATTAGTACCTAAGTAAG
GTATTGATTCTGAGCTTTCTATACCAAAATTAATGAAATAACGAACTTTTTCAACAAGAC
TATCATCATTAATGATAAGCGCACCTCCTTCAATAGAATGAAAAATCTTTGTTGCATGAA
AACTTAATGTCGAAATATCACCATAGTTTAATATACTCTCACCCTTATACTTAACATCAA
AAGCATGTGCTGCATCATAAATAACTTTTAAGTTATGTTTTTTAGCCAGCATGTCTATTT
TTTCAACTTCACAACCATTTCCAAACACATGAACTGGCACAATAGCTGAAGTATCCTCTT
CAATAGCATACTTAATTTTAGAGACGTCTATACTTAGAGTATTCTCATCAATATCAACAA
ACACTGGTTTTACATTGTTAGAAACCAATGAAGATGTAGTAGCAACAAATGAAAATGGAG
TAGTAATTGCACTTCCTTTGACTCCTAACGCTCTATACGCGATTTCTAATGCAATTGTAC
CATTTGATACTAAAACTATATTTTTAACACCTAGATACTTTGCAAGTCTTTTTTCTAGCT
CTTGCACTAACGGACCATTATTAGTAAGCCATCCATTTTTGTATATTTTATTTACATAGC
TTTTATATTTATTTATATCTGGTAAGTATGGTTTTGTTACATTTACTTTACTCATTATCT
AACCACTCCTGAAAAATTAGAATATTCCATAATATTGCTTGCCAATTTCTTTTACCACTC
AAATGCTCTTGCCAATATTTTTGCACCACCTCAGGACTTAAGTAACCTTGCTTGTCTATT
TTACTATAATCCAGTAAATTATCTGCCCACTCTCGTAAATCTTCTCTTAACCATTTAGCA
AGCGGAATACCAAACCCCATCTTAGACCTATTGACCAAACTTTCTGGCACATATTTATAT
AACAAATCTTTCAAAATTCTTTTTCCGTTACCTCGTTGTATTTTATAGTCAATTGGTAAG
GAATAAGCAAATTCATAAATATTATGATCTAAAAATGGCACTCTTGTCTCTAGAGAGTTA
GCCATAGCTGCTCTATCAACCTTAACCAATATATCATCTATCATATATGTATTAGAATCA
ACAAACATCATCCACTCTTGGAAAGATAATTGTGGAATATCATAAATATTCTTATCTCTT
AATATATCATACTCTTTTGCTCCTAACACAAAGCTAGTATCATTTATTTGTGAACAAAGT
AGTACATAAAGCTCTTTATTTGTTTTTGCTTTTTCGAGAACTCTTTTTAGTTTTAGTAGT
TTATCTGCTAATAAAGCGAACTTACCAAAATTTAATATCTCAGCTTTTTTTATCCAAGCA
TCTGGTGCATATTTAAGTAACTTAGCAAATTTGATTTTTTTAGCAATATTTGGTGCTAAA
AAGTATCTATTATAACCGCCAAAGAGCTCATCACCAGCGTCACCTGATAGTGCAACTGTT
ACTTTCGACTTAGCTATTTTACTCACAAGATACGTTGGTATTTGTGATGAATCAGCAAAG
GGCTCGTCATATATTCCAGCAAGTTTTGGTATTACATCAAGAGCATCTCTTTCTGTAACA
TACATATCTGTGTGGTTTGTACCTATATGTTTTGCTACTGCTCTTGCATGCTCAGCTTCA
TTATATTCTTTTTGATTAAAACCTATACTAAAAGTGTTTATCTTATCTTTAGACATACTT
TGCATAAGAGCAACTACAGTTGTTGAGTCAATTCCTCCGGATAAAAATGCTCCTAGAGGA
ACATCTGACTGCATTTGTATTGATAGTGTACTTTTAAGCTTAATTTCTAAATCTAGGATT
GCTTGATCATACGAATCTTTATATTTTTCTGAATCTAGTACTTTTTTAGAATCCCAATAT
TTATACTCTTTACTATTACCTTTAGCATCAAATTTTATGTAACTACCTACATTTAGTTTA
GATATATTTTTATAAATAGAGTATGGTGTTGGTACATAAGCATACCTCATATATGTTGCT
AAAGCATCTCTATCTATATCAAACCTCCAGCCACATTCCTTTAATGGCTTAAGTGCCTTC
AATTCTGATGCAAAACCCAAAATACCATTTTGGATACCAAAATATAATGGCTTCTCGCCA
AATCTATCTCTAGCTAGTATTAAGCAACTAGTTTTTCTACTGTAAACTCCAAAAGCAAAC
ATTCCTATGCATTTTTCTAAAGTTTTATCTATACCCCAAAGTTCAATAGCATTGACCAAA
ACCTCAGTATCACTGTTACTTTTAAATTTAAGATTTGAATATTCACTTAATAGCTGATTT
TTTATGGATAAGTAATTATATATTTCTCCATTAAACACAATAGCAGTATTACCGCTATTA
GATAACATTGGCTGATGTCCCGCATTAGTTATATCGTGTATTGATAATCTAGTATGCCCC
AGAGTAACTTGATTGTCGCACCAATACCCACTATCATCCGACCCTCTATGCTTTATAGAA
AGCAATGATTGATTAATTATTGAGTCAAAACCTTCTTCTTTATTAAATGAGTAAAAGCCT
ACTACTCCACACATTAGACACTGCCCTCATGATAAAGTTTTTCGTGTTTTTCCAAAATAG
CTTCTATACTAAAATTATTTATTATATATTCTCTCATGCGCTTTTTCATGACTACCGTTG
TTTCTAAAACTTTCATAATCTTTTCTATTATTTCTTTATTACCTTGACTAAGCTCAAAAA
CTTCACCGTATCCATTAAGTATATCTTTACAATCTCCAACATTAGAAGCAACAATAGGAA
CTTCACATAGCATGGCTTCTGCAAGTATATTTGGAAAACCTTCAACTTTTGATGTAGACA

Figure 5E

AATATAAATCTAATACTGGTAAGTATTCACTAGAATCCACAGATTCAAATACAAAAAACT
TATTTACATTACTTTTGTTATCTAGATAACTACCTATATCTATTTTCGAACACTCTCTTC
CAGCAATTAAAAACCGTAAACTAGGATTACTTTTTAACAATAAATTAGCTATTTGTAAGA
AACGAGAAATATTTTTATCAGCATGATTTCTTGCTATGATACCTATAATTTTAACATTAT
CATCTAAATCATTATTTAAACGAAATTTTTCATACTTTAAAAAGCTCGGTTTAAAAACAT
CTTTATCAAAACCATTTGCTATAAAGCATTGGTTTTTAAAACCTATATTTTGATGATCTT
CTAATGATTTCTTTGAATTATTTAATGTTAAATCTGAGAACTTAGAAAATTTTGCATTCA
ACTTTATCATAAACTTTGTAAGATTCTTATGACCATCATAATTCTCCAATCCCATTCTTA
TACTATTTATATATTTAGTCTTTCTATAAAAAGGCTTGCATAATATAGAAATTACATTTG
CATGATACATCCAAGCATGAATAACATCAGGCTTTATTCTTCTGATAATCTTAATATATT
TAAACAATACAAATAGTACATTAAATTTATTTAAATTTAATGTATAAACTTTAACACCAT
AAGCTTCTAACTTATTTGCAAATACTCCCCTACCCATAAGTGATATAATCGTAATATGAT
ATATTGACTTATCCATAGATTTGCAAAGTTTATAAAGCATTGTTTCAGCACCACCTTGGT
TAAGGTTTATTATTAAATGTACAAACCTTTTCAAATCACACTCCTAGTTGTAAAGCTGTT
TTCTTTAAGAGAAAAAATAAATAATATAATGGTTAATTTAGTAAATAATCCTACTGTCAA
AAAAATTATTTTTGCTTGAAAAACTAAACATACTATTAACAACAATAGAAATAATGATCG
ATACTCTGAAAATATAAAACATTTTCTCATTTCAAAGTACAAGAAAATAATAAGAATATA
AAAAAACATACTAAATATAATCCCATAATAGTATAAATATTTAATATAACCAATATCAGT
ATTACTAACATCCTCACAACCAAATATCCAAGTCAAAAGGTTATCTGGCACAAAAAGCAT
TTTATTGATTAAAACACTTAGACTTCCATGTGAAAAATCGCCAGATTGAATGTACGAGTA
AATATTTTCAAAAGCCCAACTCAAATTCAAATTTAATTTGAACAATATCCATATTGATAA
AAAGAATAGCGCCAATATTATAATAAACAGTAATTTTTCTTTTTTAATATATATATAAAA
TATTGTTATTAACAATATAAGTGAAGAAGTTAAGAGTGATGTTCTAGATATGAAAATATT
AGAAAACACAATAAGAATTAAAGGTACAAACAGCATAAGTTTGGTAAATATAGATTTACC
TTTAATATATTTGATAAAATAAAATATAGAAAAACATAATCCTATAGTAATTGAAAATCC
TAAACCATCCCCTCCAGCGTTACTAAGTCCGAATACTCTTAACTTATATTCAATAACATT
CGAAATCTCAATATTCCCTTTTTTCACTAAAAAAAAGAATATCCAATCATTTAAAAATAT
ATAATACCTTGAAAGAAATACAAAAATAGATTGTAAGAAAGTAACAAAAAATATTATTTT
AGACATATTAAAAAAATAATTTTCATTATTATCATATGAAACAAAAATAAAGTTACAAAA
ACCTATCGCGATCAAAATGTTAAATAAAAACTGAGGAAACAATGATGCTGCATCAAGTAA
GATTATTTGGACTATTATTAAATAAATCATTGATAAAAAGAAAAAGAAAAAAAGGAAAGC
TAATTGTTTCTTAACAATATTTCCGACAAATAGTTTTTTAAGAGCTAAAAAACCCAAAAT
ACAAGCCGGAAGATAAACTATAATATTCAATATAGCAAATTTAAATTCTAAACTAAAAAT
AATACAAAAAGCTAGTAAATATAAATATAAAATTTTAAAAGACACTTTTTTTATGTACAC
TTGATTAAAATACCATTTAATTAATTAAATACCACTCAACAGCATGCTTTATGCCTAATT
CAAAATCATATTCCGGATTATATCCGAGCATATTCCTAGCCTTCGAAATATCAGCATTAC
TATGCTTAATATCACCCGCTCTATCTGGACCAAAATTTGGCTCTATTTTTTTACCCAAGG
CATCACAAAGATTATAGTACAAATCTATAAGATACTCTCTACCTCCATAAGCTATATTAA
AAGACTCTCCGGCATACTTACTATCTGCTAAACATGCTTTAAGATTTGCCTCAATAACAT
TCTCTATATATGTAAAATCTCTCGACTGTTTACCATCTCCATTTATAGTTGGCGCTTCAT
CATTTAATAACTGTTTGATAAATTTAGGTATAACTGCTGCATACGCACCATTAGGATCTT
GTCTTCTACCGAAAACATTAAAATATCTTAGACCATAAGTATCTAGACCATATAACTTTG
TGTATAGTCTCGCCCACTCTTCATTAGCTTTCTTTGTAAATGCATAGGGTGATAAAACAT
TTCCTTCTCTACCTTCTTTTTTAGGTAAATTTGGCTCATCACCATATACTGATGAACTAG
AAGCATAGACAAATTTTTTAACGTTATTTTGTCTAGCCGCTTCAAGCATATTTAATGCAC
CTTTAACATTTATATCTTCATACACTAATGGCATCTCAATACTTCTTGGTACGCTTCCCC
AAGCAGCTTGATGTAGAACATAATCAATACCTTCACAAGCTTTCATGCAAGTATCTAAAT
CTCTAATATCACCTTTTATAAACTCATAATTAGAATTAGTTAAAAACGGCTCAACATTGT
GATAGTGACCATTTGAGAGATCATCTAAACACCTAACTCTATAACCCTTACTAAGTAAAA
CTTCACATAAATTAGAGCCAATAAAACCCGCACCTCCAGTCACCAAAAAAAACGAACCAT
GAGGAAATTTAACATTATCGTAAGCCACTACAATCTCCAATAAATATAATCTTTTTCAAA
CTCAGATTTATCTAAACTACCTTTGATGTCAAATATAATCTTTCTAGAATTATGCGCATA
TAGCCTATCAAACTGTTGCTTTGTTATATCTTTAAACTGTTCGTGACTAACAGCAATAAT
GATCGCATCTAGATTGACCATTTTACTTAGATCATCAAACTCAAGTCCATACTCATGTTT

Figure 5F

AGCCTCTTCTTTATCAGCTACCGGATCTATAATATATGGCTCTATACCATACTCGTTGAG
CTCTTTTACCATATCTATAACTCGAGTATTCCTAGTGTCAGGACAGTCTTCTTTAAAAGT
AAAGCCGAAAATTGCTACTCTAGCTCGCTTAACAGGTATATCTGCAGATATCAGTTTTTT
GACTAAATTCTCAACTACAAATTTACCCATACTATCATTTATCCTACGACCAGATAATAT
TACCTGAGAATGATATCCAAGCTCAGCTGCCTTGTACGTTAGGTAATATGGGTCAACACC
AATACAATGTCCACCAACAAGACCAGGCTTAAAGTTTAAGAAATTCCATTTAGTTGCAGC
TGCTGCTAAAACCTCTAGAGTATCAATACCCATCTGATTAAATATTATCGATAACTCATT
AACAAAAGCTATATTAACATCTCTTTGAGAGTTTTCTATAACCTTAGCAGCTTCAGCCAC
TTTTATACTACTAGCTCTATAAACTCCTGCGTCTACTACTAGCTCATAAACTTTTGCTAT
AGTATCTAAAGACTCTTCATCCATACCAGATACTACTTTGATAATTGTTTCTAACCTATG
AACCTTATCACCAGGATTTATCCTCTCAGGAGAGTAACCAACTTTGAAATCTTCACCAGA
CCTCAAGCCAGACTCTTTTTCAAGTATTGGTACGCAAACATCTTCTGTAACACCAGGATA
AACAGTTGATTCAAACACAACATAAGCGCCTTTGACAAGATTCCTACCAACCGTCTCACT
TGCCTTAATAATCGGCGTCAAATCAGGAGTTTTATCTGCTTTAACTGGTGTAGGAACTGC
AACAATATGAAATTTACACTCTTTAAGACTTGTTTCATCACAACTAAATTTCATTGTCGT
ATTTCTGACAGCCTCATCTCCTACTTCTTTTGTTGGATCAAAACCATCCTTATAATGTTG
AACTTTTGTTTCACAAATATCAAATCCTAACACATCTATTTTTTTTGCAAATGCAATAGC
TATTGGTAAACCAACATAACCCAAGCCAACCAATGAAACCTTTTCTCTTTTAGCGACTAT
ATCCTCATATAAACTCATAATTTAAACCCTTATTATTAATTTTGCTGTAAGTATGCATTG
ACAACAATACTTCTATCAAAATCTTTTTCTATCTTAGCTCTAGCTTTATAGCTCATAGCT
ATTTTATCAGTATACGACATATTTATAAACTGCTCTAATGAGTTACGTAAAGAACTCACA
TCATTAGGGTTACATGATAAGCCAGAGAGACCATCATCAAAAATTTCTCTACACCCAGGA
ATATCTGACGCAATTACAGGTCTACCTATCGCAGCTGCTTCTAACAGCACATTTGACATT
CCTTCATGGTAAGATGGCAAAACAACTGCATGTGCACTAGCTATTTTTTCTTTAGTATTA
TCAGTAAAACCATAAAATTTTACTGATTTTATCGTATTAACCTTTCCCATAAAATTAGAT
TTATTTTCATCACAAAAACCATAAATGTCAAGACTAATATTTTTATATTTTTTCTCAAGT
ATAGCAAAGGCTTCTAACAATTCATAAATCCCCTTTTCTTTCATTATTCGGCCAAGAAAA
ACGAATTTTAATATTCCTTGGTCTTTAGGATAGTCAACATATTTATTTTCATCTAAGTTT
ACCCCAGAACCTGGTAATAATATTGATTTTTCTCCACTGATTATTTTCTTAGCTATAAAT
AACTTTTTATTTTGCTCATTCTGAAAGAATACTTTTGTGGTGCTTTTAAATGATAACTTA
TATAAAGATATTATAAACTTCTGAACAATACCATGATTAGCAAAAACACTTCCTAAGCCT
GTTACATTTGGATAAAACTTCTTCCTAAAAAACAAATTCACTAACCCAACATACAAATTT
GGTTTAATTGTATAGCTAAAAATGTAATCAGGTTTTTCTTTTTTTATTATTTTGAAATAG
TTAAATAAAAGAAGCAAATCCTTAAAAGGATTTTTGCCTCGTCTATCTATATCAACATTT
ATATACTTAACACCAAGACTTTTACAAAAAACCTCTGCTTTCTTAGAATATGGTGTTACT
AGTACTATCTCATACTCTTTAGCAGCAAAAGACTCGATTACTTCTCTTCTGAAACGATAT
ATTACAATATCAAAATCATTAGCTATGAATAATAACTTACTTCTCATAAGTCAAATTCCC
AAAAACTTTATTAATAAAATCTACTTTTTTAGCAAGCAATCTTATAATTGGATTAAAAAT
TTTTGTCAGATAAGTTCTCTTACCTAAAACATCTTTTCTATAGTTTTTTATAAACTGTGA
AGTGCAAAAATATTCATTATCTTGAAGTAGAAAAACTCCATGTTTAGTTTGCAAAATTAT
TTCTGCAATCTCTTTAGATAAATTATCTATAGATATAACACTTCTTTGGTTATTAATATT
AGGAAAAATAAAAGTATACTTTGCAAGTTTAACCAACTTTGGATAGTTGCCTTTTGAGCC
TTCTCCATATACCATTGGTGGTCTGATTATAGCAATATTAAAGTCATCACTAGCCAGGCT
ATTTAGCTTAATTTCAGTTTGAAGCTTACTATCTCCATAAAAATCATCTGGTTTAGGTTC
GGTATATTTAGTTATAACTTTTTGTTGACCTATTGGCGCACTATCACCATAAACTATAAT
ACTACTTAAAAACACAAACTGTCGAACACCTTGATCTTTAGCTTGTTTTGCCAGATCATA
AGTTAATTGCGTATTTATTTTATAGTATTTTTCTTTTAGTTTAGGATCCTTTGAAGTATG
GGCAATTCCAGCGACATGCAATACAGCATCATAACCACTTAAGTCTATATTTGCCCACGA
AACATCGCGCAAAGATATTTTATCGATACTAAAATCTGAGTTATATTTAGCCGCAAATGA
GTTACCAATATAGCTACTCAAACCTGTAACTAAGATTCTTTTTTTCATACTACTTTAAAT
CCTCTTTGTTACCTAAAGCTCCAGTACCACCCTCAACGACGCCCTTTTTGGCAAAAACAG
AAAATACTGTCAAAAAAATACATTTTAAATCAAACCATGTACTTTTATTTTTTACATAAT
CACCATCAAGTTTAGCTTTATCAGGTATTGGTAATTCATCCCTACCATTAATCTGTGCCC
AGCCAGTCAGTCCCACAGGCACAGCATTTGCCCCATACTTATCTCTTTGTGCTATTAAGT

Figure 5G

CATCTTGATTCCATAATGCTGGTCTTGGACCCACGATGCTCATTTCACCTTTTAGAATAT
TTATAATTTGTGGCAACTCATCTAAAGATGATTTCCTTAAAAATCCTCCAACCTTAGTTA
TACATTTCGATGGATCCTGTAACATGTGCGTTGGCATATCTTTTGGAGTATCAACATACA
TAGTTCTAAACTTATATATGTAAAAAAATTGCTTATCTTTACCATAGCGCTTTTGTTTAA
AAAATATAGGTCCTTTTGAATCTTTCTTTATCATAAAAATAATAATTAAGAAAATAGGAC
TTAATAACAACAACCCCATAAAAGAAAGTAAAATATCAAGCAATCTTTTAAAAACCTCAT
AAAACATAAAACCACTACCCATTCAATCTATGTTCAAATTCCGGAACAATTTTCTTTAAT
ATCACAAGCTGATCAACATCATCCTTGATCAACGATTCAATATCTTGGTTTAGAGTATTA
ATATCGTAAAAAGTCCTTCTACCAATAAAAATATCTTTATAGTCGGTACTAACATCATCT
TCCTCTATCAAAAGCTCTTCGTAAAGTTTCTCTCCTGGACGCAAACCAACTATTTTAATA
TCAATATCACCTCTACCAGAAAGTCTAATAAATTGTTTAGCAAGATCAATAATCTTGACA
GGTTGCCCCATATCTAAGACAAAGACCTCTGAATTTTTTGCAATAGCACCAGCTTGTAGG
ACCAGTTCACAAGCTTCTGGTATCAACATAAAATAACGTGTAATTTCAGGATGAGTAACT
GTAACAGGACCACCTTTTCTTATTTGCTCTTCAAATTTTGGAATCACACTGCCACTACTA
CCAAGCACATTACCAAAACGCACTGCAGCAAGCTTGGTATTTTTGGGATCAACATTCTGT
AAATACAGCTCACAAACTCTCTTGGTAGCCCCCATAACATTCGTTGGTCGCACTGCTTTA
TCAGTGGAAATCAATATAAATGACTCAACACCAGCTTCTATAGCCAGATCTATAGCATTC
TTAGTACCTAAGATATTATTTCTAATTGCTCTAGAGATATTCTCCTCAACTAAGGGAACA
TGCTTGTAGGCAGCAGCATGAAATACTATATTTGGAGTATACTTTTGAAAAACCTCAGCC
AATGCTTTTCTATCACAAACAGAACATAGCACACTATTGATATTAAAATGACTACACTCC
TCAGTAATTTTATATAAGTTAAACTCACTATGATCAACCAATATCAACTCTTTTGCCTGA
TACTTGATACATTGATGTACTATTTCAGAACCTATACTACCTCCAGCTCCTGTGACTAGC
ACCACCTTATTTTTGATAAAATTAGAGATAGATTCTTTATCTAAACTCTTAGTATCACGC
GCTAATAGATCATAGAGTGAAACAGGCTTCAACTGTGACATAAAATTCTCATCTTGAAGA
ATTTCCTCAAGAGGCGGCATAATTCTAATCTGATTAAAATCCTTTTCAAATTCTTTATAT
ATATTTTTGACTACTTGGTTTGCATTTCTTGGCAATGCAATAACCAAAAGGTCAAATCTA
CTAGATAGCAATAGTTTTGTTAATTCAGCTTTAGATAGAACCTTTTTACTATCAATACTT
CTTTTTTGTAAAGTTTCATTGTCATCAACAAAACATTTGATGCGATAACCAGCAGAAGCA
AGTTCTTGAGCAATCTTTGTTCCTGCAGCACCTGCACCATAAATAACCGCAGTTTTACTT
TTATCCACTGATCCTCTGTTCATCAAATACCAATAAAAGTAGACACTTAAACTGATCAAA
AAAACATAAAATAAAAACTCAGAGAATATCAACGAAAAAGTGACTTTGCCATAAAAAAAT
AATGCCACTATGAAAAATACTGGCAAATTAATAAAAGCCTTACGTAAAAAAGTTTTTTGA
GTCGACTTACGCCAACTAGCCATATAATCTCTAAGTAGTAAAAAAGATGACAAGCATCTC
AGCAAAACTAATGCAAGTAAAAAATGTAAATTAACATCTTGCTTGAAAATATAGAAAGTC
CAATTAACAGTAATAATAGTTAAAACTATTATTACCACGAAATTAAGCGTTCTATTATCG
TAGAAAGACATTTGTTAATTTTTAGAAAATATCCTATTAAAGTCTATTATATCAAAAAAA
TTTTCTTTGTGCACAAAAATGCAAATTAGGTTCTGTGCACAAAAATAAATATTCATCGTA
ACCAAATAAAAGTACAAGCTAATTTAATCATTCCTATATATGCTAAAATGGTTTTATCAA
ATCTAGAGAATACTCTTCTAAAATGCTTAATTTTAGAAAAGAAATTCTCTATCAAATGTC
TTTCTTTATATACATGACTATCAAAAGGTATATGGTTTAGAGTATTTGATTTACAAGGGA
TAACAGCTTCAGAGGATATACCTTGAATATGCTGCCTGATTTCATTAGAATGATATGCTC
TATCAGCGATAACTTTTGTATTATATACATTTTTTAGTAAATCTATAGCTACTTTACTAT
CATGAGTTTTATCCTCTGACAACAATATTTCTATTGGATTACCTAAAGCATCAGTCATAG
CATGGATTTTAGTGGTTATCCTACCAACTGATCTACCAATTGCTTGGTTATCATCTTTAT
CATATCCCGTAGCACAAGCATGTGCTCTTGCTATTGTTGAATCAAGCATGACTTCTTGTA
AATCAGGGTTTTGTACTGATTTAAATAATCTAGAAAATATATCTTTATCACACCAATCTT
TAAAACGCTTATGTATTGATCTATATTTACCATAATAAAATGGTAACATTCTCCATTGAC
AGCCTGTACGTAACACATAAAATACAGCTTCAATAAACAATCTTAATTTGGCTTCATCAT
TGGTATGTATACCTTTTTGTGATTTTAAGAATGATAAAATAATTGACCAGAATACTTCTT
TTATATGATAATTCATTTGCTAAACCATTGATATTTATTGCTTTTCAAATCTTAAATAAC
AGCGGTTTAGCTATTTTCAATATAATTTAAGTTTTTTGTGCACAGAACCTATTATTTTTT
GTTTGCTATCATCATTTATAAAAGAAGCTCTTGCAGCATTTAGATTCATAATAACCATAT
TTCAAAGGAAAGATTATTTTTAAGATAAGCATTATAATACTCATCTGTCATTGTTATGTT
TCTAAGCATCAATCGATCATCCGTATAATACTGATATTATCAGCTAACATTCTTTGATAA

Figure 5H

GAGTGATTTTCAAAACTATCTACAATACCTAAAGCTACGTTACTACTTACATTTGACTCT
ATATGAATATTTCTATCAATTAGTAAAGCAATAACTTCACGTAAAAGATCTAAATCTTTA
GTTTTATATAGATTACAACCATGACCTATTCTAGATGCACCACTTAAAATACTAGCTTTG
ATATTACTAATACTAGAAAACTCACCACTATGAACAGTAAATTTAACATTATTATTTCTA
AGAAACTCTAGTGTTCTAGGTAATACTTTAGATACATCACCAGCAATATCCATTCCAGCA
ACATCATAACCAACAATTTGAGAATATTTCGTACATAACTCCGCTAATTCAAGGTTAATA
TCATCACTAAGGCTATACATACCACAAACAAGTATACCTGCTTCTATATCATATTTTTGT
TTGGCTCTCGCAAACCCTGCTGATATACTTTCGATTATCTCAGCATATGATAAATCTTGA
TTACGGTGGAAATAAGGGCAAAATCTGGCTTCGACATAAATAACATTATCTAAAGCATGA
TCTTCAACAAACTCAAATGCAACCCGTTCAAGACCTTCTTTAGTTTGCATAACAGCGCCA
GCAATATTAAAAGCAGCAAAACATTTGTCAAAGTCTTTTGATGAAAATTCACCATAGAAC
CATTCTAAAAGTTCAGCTGAGTATGCTTCGGAAGTTTAATATTGTACTTAGCAGCAAGTT
CTATAATAGTATCAACACGCAAACCACCATCAAGATGATCATGCAAAACAACTTTTGGTA
TCGAAAAAATCTTATCTCTCAT

Figure 6: (SEQ ID NO:9)

```
ATGTTGAAAA AAGAGTATTT AAAAAACCCT TATTTAGTTT TGTTTGCGAT GATTATATTA     60
GCTTATGTTT TTAGTGTATT TTGCAGGTTT TATTGGGTTT GGTGGGCAAG TGAGTTTAAT    120
GAGTATTTTT TCAATAATCA GTTAATGATC ATTTCAAATG ATGGCTATGC TTTTGCTGAG    180
GGCGCAAGAG ATATGATAGC AGGTTTTCAT CAGCCTAATG ATTTGAGTTA TTATGGATCT    240
TCTTTATCCG CGCTTACTTA TTGGCTTTAT AAAATCACAC CTTTTTCTTT TGAAAGTATC    300
ATTTTATATA TGAGTACTTT TTTATCTTCT TTGGTGGTGA TTCCTACTAT TTTGCTAGCT    360
AACGAATACA AACGTCCTTT AATGGGCTTT GTAGCTGCTC TTTTAGCAAG TATAGCAAAC    420
AGTTATTATA ATCGCACTAT GAGTGGGTAT TATGATACGG ATATGCTGGT AATTGTTTTG    480
CCTATGTTTA TTTTATTTTT TATGGTAAGA ATGATTTTAA AAAAAGACTT TTTTTCATTG    540
ATTGCCTTGC CGTTATTTAT AGGAATTTAT CTTTGGTGGT ATCCTTCAAG TTATACTTTA    600
AATGTAGCTT TAATTGGACT TTTTTTAATT TATACACTTA TTTTTCATAG AAAAGAAAAG    660
ATTTTTTATA TAGCTGTGAT TTTGTCTTCT CTTACTCTTT CAAATATAGC ATGGTTTTAT    720
CAAAGTGCCA TTATAGTAAT ACTTTTTGCT TTATTCGCCT TAGAGCAAAA ACGCTTAAAT    780
TTTATGATTA TAGGAATTTT AGGTAGTGCA ACTTTGATAT TTTTGATTTT AAGTGGTGGG    840
GTTGATCCTA TACTTTATCA GCTTAAATTT TATATTTTTA GAAGTGATGA AAGTGCGAAT    900
TTAACGCAGG GCTTTATGTA TTTTAATGTC AATCAAACCA TACAAGAAGT TGAAAATGTA    960
GATCTTAGCG AATTTATGCG AAGAATTAGT GGTAGTGAAA TTGTTTTTTT GTTTTCTTTG   1020
TTTGGTTTTG TATGGCTTTT GAGAAAACAT AAAAGTATGA TTATGGCTTT ACCTATATTG   1080
GTGCTTGGGT TTTTAGCCTT AAAAGGGGGG CTTAGATTTA CCATTTATTC TGTACCTGTA   1140
ATGGCCTTAG GATTTGGTTT TTTATTGAGC GAGTTTAAGG CTATAATGGT TAAAAAATAT   1200
AGCCAATTAA CTTCAAATGT TTGTATTGTT TTTGCAACTA TTTTGACTTT AGCTCCAGTA   1260
TTTATCCATA TTTACAACTA TAAAGCGCCA ACAGTTTTTT CTCAAAATGA AGCATCATTA   1320
TTAAATCAAT TAAAAAATAT AGCCAATAGA GAAGATTATG TGGTAACTTG GTGGGATTAT   1380
GGTTATCCTG TGCGTTATTA TAGCGATGTG AAAACTTTAG TAGATGGTGG AAAGCATTTA   1440
GGTAAGGATA ATTTTTTCCC TTCTTTTGCT TTAAGCAAAG ATGAACAAGC TGCAGCTAAT   1500
ATGGCAAGAC TTAGTGTAGA ATATACAGAA AAAAGCTTTT ATGCTCCGCA AAATGATATT   1560
TTAAAAAACAG ACATTTTGCA AGCCATGATG AAAGATTATA ATCAAAGCAA TGTGGATTTG   1620
TTTCTAGCTT CATTATCAAA ACCTGATTTT AAAATCGATA CGCCAAAAAC TCGTGATATT   1680
TATCTTTATA TGCCCGCTAG AATGTCTTTG ATTTTTTCTA CGGTGGCTAG TTTTTCTTTT   1740
ATTAATTTAG ATACAGGAGT TTTGGATAAA CCTTTTACCT TTAGCACAGC TTATCCACTT   1800
GATGTTAAAA ATGGAGAAAT TTATCTTAGC AACGGAGTGG TTTTAAGCGA TGATTTTAGA   1860
AGTTTTAAAA TAGGTGATAA TGTGGTTTCT GTAAATAGTA TCGTAGAGAT TAATTCTATT   1920
AAACAAGGTG AATACAAAAT CACTCCAATT GATGATAAGG CTCAGTTTTA TATTTTTTAT   1980
TTAAAGGATA GTGCTATTCC TTACGCACAA TTTATTTTAA TGGATAAAAC CATGTTTAAT   2040
AGTGCTTATG TGCAAATGTT TTTTTTAGGA AATTATGATA AGAATTTATT TGACTTGGTG   2100
ATTAATTCTA GAGATGCTAA GGTTTTTAAA CTTAAAATTT AA
```

Figure 7: SEQ ID NO: 22

```
MLKKEYLKNP YLVLFAMIIL AYVFSVFCRF YWVWWASEFN EYFFNNQLMI ISNDGYAFAE    60
GARDMIAGFH QPNDLSYYGS SLSALTYWLY KITPFSFESI ILYMSTFLSS LVVIPTILLA   120
NEYKRPLMGF VAALLASIAN SYYNRTMSGY YDTDMLVIVL PMFILFFMVR MILKKDFFSL   180
IALPLFIGIY LWWYPSSYTL NVALIGLFLI YTLIFHRKEK IFYIAVILSS LTLSNIAWFY   240
QSAIIVILFA LFALEQKRLN FMIIGILGSA TLIFLILSGG VDPILYQLKF YIFRSDESAN   300
LTQGFMYFNV NQTIQEVENV DLSEFMRRIS GSEIVFLFSL FGFVWLLRKH KSMIMALPIL   360
VLGFLALKGG LRFTIYSVPV MALGFGFLLS EFKAIMVKKY SQLTSNVCIV FATILTLAPV   420
FIHIYNYKAP TVFSQNEASL LNQLKNIANR EDYVVTWWDY GYPVRYYSDV KTLVDGGKHL   480
GKDNFFPSFA LSKDEQAAAN MARLSVEYTE KSFYAPQNDI LKTDILQAMM KDYNQSNVDL   540
FLASLSKPDF KIDTPKTRDI YLYMPARMSL IFSTVASFSF INLDTGVLDK PFTFSTAYPL   600
DVKNGEIYLS NGVVLSDDFR SFKIGDNVVS VNSIVEINSI KQGEYKITPI DDKAQFYIFY   660
LKDSAIPYAQ FILMDKTMFN SAYVQMFFLG NYDKNLFDLV INSRDAKVFK LKI          713
```

Figure 8 (SEQ ID NO: 11)

```
ATGGGAAAAATAATAGGTATAGATTTAGGTACTACTAACTCTTGTCTTGCTATTATGGAT
GGCAAGACTGCTAAAGTTATTGAGAATGCTGAAGGACATAGAACAACACCTTCAGTTGTG
GCATATACTGATAGCGGTGAAATATTAGTAGGTCAAGCTGCTAAAAGACAAGCTGTAACT
AACCCTGATAATACATTCTTTGCTATCAAGAGACTTATAGGTCGTAAGTACGATGATAAA
GCTGTACAAGAAGATATTAAAAAGAAAGTACCTTATGCGGTAATTAAAGCTGATAATGGT
GATGCTTGGGTTGCTACTAAAGAAGGCAAAAAAATGGCTCCACCACAAGTTTCTGCAGAA
GTTCTAAGAAAAATGAAAAAAACAGCAGAAGACTATCTAGGTGAACCAGTTACAGAAGCT
GTAATTACAGTGCCAGCATACTTTAACGATAGTCAAAGACAAGCTACAAAAGATGCTGGT
AAAATAGCAGGTCTTGAAGTTAAAAGAATTATCAACGAGCCTACAGCGGCAGCGCTGGCA
TATGGTGTAGACTCTAAGAAAGGTGAGCAAACTGTAGCGGTGTATGACCTAGGTGGTGGT
ACATTCGATATCTCAATTATTGAGATTGCTGATGTTGATGGCGATAACCAAATCGAAGTA
TTATCAACCAATGGTGATACTTTCTTAGGTGGTGAAGACTTCGACTTGGCTTTAATGAAC
TATCTAATTGACGAGTTCAAAAAAGAGCAAGGTATAGATCTTCACAATGATAAGCTTGCT
TTACAAAGAGTTAGAGAGGCTGCTGAGAAAGCTAAAGTAGAATTATCTTCAGCACAACAA
ACTGATGTTAACCTACCTTACATCACAGCAGATGCTACTGGACCTAAGCACTTAAATATC
AAAGTAACTAGAGCTAAGTTTGAGTCTTTAGTTTCTGATCTTGTAATGAGATCACTTGAG
CCTTGTAAGAAAGCTCTTGAAGATGCTGGTTTAAGTAAGTCTGATATTACAGAAGTATTA
CTAGTGGGTGGACAAACTCGTATGCCTCTAGTACAAGAGAAAGTAAAAGAGTTTTTTGGT
AAAGAGCCACGTAAAGATGTGAACCCTGATGAAGCTGTTGCAGTTGGTGCGGCTATTCAA
GGTGGTGTATTAGCAGGTGATGTTAAAGATATTCTTTTATTGGATGTAACACCGCTTTCT
CTAGGTATTGAGACTATGGGAGGTGTTATGACTAAGCTTATCGAGAGAAATACTACGATT
CCTACTAAGAAGTCGCAAGTATTCTCAACAGCTGAAGATAACCAGCCTGCGGTAACTATT
CATGTACTTCAAGGTGAGCGTGAAATGGCTTCTGCAAACAAATCTTTAGGTAGATTTGAT
CTGGCAGATATTCCACCAGCGCCACGTGGTATGCCACAAATTGAGGTTACTTTTGATATA
GATGCTAACGGTATATTAAATGTGTCTGCTAAAGATAAAGCTACTGGTAAAGAGCAAAAT
ATTGTGATTAAGTCTTCAAGTGGTTTATCTGAAGAGGATATCGAAAAAATGGTACAAGAC
GCTGAAGCTAATGCAGAAGCAGATAAAAAGTTCCATGATTTAGTTACTGCTAGAAATACT
GCTGATAACTTAATTCATAGCTCAAGAAAAGCAATTCAAGAACTGGGTGACAAAGTAACA
GCAGCAGAAAAAGAAAAAATCGAAGAAGCTTGTAAAGAGCTTGAAGCAGCAACTAAAGGT
GATGATAAGCAAGCGATTGAATCTAAAACTAAGGCTCTAGAAGAAGCATTTGCGCCAATA
GCTCAAAAAGCTTATGCTGAGCAAGCTCAAGCTGCTGTTGCCCAAGGTGGTGCTAAAGCT
GAAGAACCTAAGAAAGAAGAAGATGTTGTTGATGCTGACTTTGAGGATGTTGAAGACGAC
AAAAAATAA
```

Figure 9 (SEQ ID NO: 10)

ATGATTATGAGTGAGATGATAACAAGACAACAGGTAACAAGTGGCGAGACCATTCATGTG
AGAACTGATCCTACTGCATGTATAGGATCTCATCCTAATTGTAGATTATTTATTGATTCT
TTAACTATAGCTGGGGAGAAACTTGATAAAAATATCGTTGCTATAGATGGTGGAGAGGAT
GTCACGAAAGCTGATTCGGCTACAGCTGCTGCTAGTGTAATACGTTTATCTATAACGCCA
GGCTCTATAAATCCAACAATAAGTATTACTCTTGGTGTTCTAATTAAATCAAATGTTAGA
ACTAAAATTGAAGAGAAAGTTTCGAGTATATTACAAGCAAGTGCTACAGATATGAAAATT
AAGTTAGGTAATTCTAATAAAAAACAAGAGTATAAAACTGATGAAGCATGGGGTATTATG
ATAGATCTATCTAATTTAGAGTTATATCCAATAAGTGCTAAGGCTTTTAGTATTAGTATA
GAGCCAACAGAACTTATGGGTGTTTCAAAAGATGGAATGAGATATCATATTATATCTATA
GATGGTCTTACAACATCTCAAGGAAGTTTGCCAGTATGTTGCGCAGCTAGCACAGATAAA
GGAGTTGCTAAAATAGGATATATTGCAGCTGCATAG

Figure 10: (SEQ ID NO 3)

MKKIWLALAG LVLAFSASDQ NATGGDQNAT GGDQNATGGD QNATAAEEAF DLWNECAKAC 60
VLDLKDGVRS SRMSVDPAIA DTNGQGVLHY SMVLEGGNDA LKLAIDNALS ITSDGLTIRL 120
EGGVEPNKPV RYSYTRQARG SWSLNWLVPI GHEKPSNIKV FIHELNAGNQ LSHMSPIYTI 180
EMGDELLAKL ARDATFFVRA HESNEMQPTL AISHAGVSVV MAQAQPRREK RWSEWASGKV 240
LCLLDPLDGV YNYLAQQRCN LDDTWEGKIY RVLAGNPAKH DLDIKDNNNS TPTVISHRLH 300
FPEGGSLAAL TAHQACHLPL EAFTRHRQPR GWEQLEQCGY PVQRLVALYL AARLSWNQVD 360
QVIRNALASP GSGGDLGEAI REQPEQARLA LTLAAAESER FVRQGTGNDE AGAASADVVS 420
LTCPVAKDQN RTKGECAGPA DSGDALLERN YPTGAEFLGD GGDVSFSTRG TQNWTVERLL 480
QAHRQLEERG YVFVGYHGTF LEAAQSIVFG GVRARSQDLD AIWRGFYIAG DPALAYGYAQ 540
DQEPDARGRI RNGALLRVYV PRWSLPGFYR TGLTLAAPEA AGEVERLIGH PLPLRLDAIT 600
GPEEEGGRVT ILGWPLAERT VVIPSAIPTD PRNVGGDLDP SSIPDKEQAI SALPDYASQP 660
GKPPREDLKD QNATGGDQNA TGGDQNATGG DQNATVD

Figure 11: (SEQ ID NO 4)

MKKIIKLSLL SLSIAGLASC STLGLGGSDD AKASAKDTAA AQTATTEQAA AVSKPTAKVS 60
LNKLGQDKIK ATVYTAYNNN PQGSVRLQWQ APEGSKCHDT SFPITKYAEK NDKTWATVTV 120
KQGNNFCSGK WTANVVYDKE VIASDSINI

Figure 12: (SEQ ID NO 5)

MVSREDFIMT INKLSLTDEL LNNFGGSTEV DSVLKNIDFD VSDDASKVLS LSTDYNARNL 60
MALSLVLANN DNINNYNQKY IQKVITVIDK LIDLQVNSII SNDEFRALEQ EWLKVQEVCQ 120
EDYDNVEVSI LDVKKEELQY DFERNLYDIS SSDFFKKVYV SEFDQYGGEP YGAILGLYNF 180
ENTTNDIIWL TGMGMVAKNS HAPFIASIDK SFFGVKDLSE ITHIKSFEAL LEHPRYKEWN 240
DFRNLDVAAY IGLTVGDFML RQPYNPENNP VQYKLMEGFN EFVDYDKNES YLWGPASIHL 300
VKNMMRSYDK TRWFQYIRGV ESGGYVKNLV ACVYDNKGIL ETKSPLNVLF ADYMELSLAN 360
IGLIPFVSEK GTSNACFFSV NSAKKVEEFV DGFDSANSRL IANLSYTMCI SRISHYIKCV 420
IRDKIGSIVD VESIQKILSD WISEFVTTVY QPTPLEMARY PFRNVSIEVE TIPGKPGWYS 480
CKINVIPHIQ FEGMNTTMTI DTRLEPELFG TNNN

Figure 13 (SEQ ID NO 6)

MNIRPLQDRV LVRRAEEEKK SAGGIILTGS AQEKPSQGEV VAVGNGKKLD NGTTLPMDVK 60
VGDKVLFGKY SGSEVKVGDE TLLMMREEDI MGIIA

Figure 14: (SEQ ID NO 7)

```
MAAKQVLFSD EARAKMLDGV NTLANAVKVT LGPKGRNVVL DKSFGTPTIT KDGVSVAKEI    60
ELEDKFENMG AQIVKEVASK TADVAGDGTT TATVLAQALL TEGLKAVAAG MNPMDLKRGI   120
DKATARLVEE LKALSKPCSD PKSIEQVGTI SANSDATVGK LIADAMAKVG KEGVITVEEG   180
KGFEDELDVV EGMQFDRGYL SPYFATNQEN MTTDLENPYI LIVDKKISNI RDLLPILEGV   240
SKSGRALLII AEDVESEALA TLVVNNMRGV VKVCAVKAPG FGDRRKAMLE DIATLTGATF   300
VSEDLSMKLE ETNMEHLGTA SRVQVTKDNT TIIDGAGEKE AIAKRINVIK ANIAEANSDY   360
DREKLQERLA KLSGGVAVIK VGAVTEAEMK EKKDRVDDAL HATRAAVEEG IVAGGGVALI   420
RAQKALDGLT GENDDQNYGI ALLRKAIEAP LRQIVSNAGG ESSVVVNQVK ANQGNYGYNA   480
ANDTYGDMVE MGILDPTKVT RSALQHAASI AGLMITTEAM IGEIKEAAPA MPMGGGMGGM   540
PGMM
```

Figure 15: (SEQ ID NO 22)

```
MLKKEYLKNP YLVLFAMIIL AYVFSVFCRF YWVWWASEFN EYFFNNQLMI ISNDGYAFAE    60
GARDMIAGFH QPNDLSYYGS SLSALTYWLY KITPFSFESI ILYMSTFLSS LVVIPTILLA   120
NEYKRPLMGF VAALLASIAN SYYNRTMSGY YDTDMLVIVL PMFILFFMVR MILKKDFFSL   180
IALPLFIGIY LWWYPSSYTL NVALIGLFLI YTLIFHRKEK IFYIAVILSS LTLSNIAWFY   240
QSAIIVILFA LFALEQKRLN FMIIGILGSA TLIFLILSGG VDPILYQLKF YIFRSDESAN   300
LTQGFMYFNV NQTIQEVENV DLSEFMRRIS GSEIVFLFSL FGFVWLLRKH KSMIMALPIL   360
VLGFLALKGG LRFTIYSVPV MALGFGFLLS EFKAIMVKKY SQLTSNVCIV FATILTLAPV   420
FIHIYNYKAP TVFSQNEASL LNQLKNIANR EDYVVTWWDY GYPVRYYSDV KTLVDGGKHL   480
GKDNFFPSFA LSKDEQAAAN MARLSVEYTE KSFYAPQNDI LKTDILQAMM KDYNQSNVDL   540
FLASLSKPDF KIDTPKTRDI YLYMPARMSL IFSTVASFSF INLDTGVLDK PFTFSTAYPL   600
DVKNGEIYLS NGVVLSDDFR SFKIGDNVVS VNSIVEINSI KQGEYKITPI DDKAQFYIFY   660
LKDSAIPYAQ FILMDKTMFN SAYVQMFFLG NYDKNLFDLV INSRDAKVFK LKI          713
```

Figure 16 (SEQ ID NO 23)

```
ATGTCAAATT TTAATTTCGC TAAATTTCTA AATAAATTAC CTAGACTTTC TAAACATACT      60
ATTTTAATGA TTGTTTTAGC TGTTTGTTTT GGGATATTTT GCAGATTTTA CTGGGTAGTT     120
TGGGCTAGTG CTTATCCGCA TTTTATATGG AATGATCAGC TTATGATAAG CACAAATGAC     180
GGATATGCAT TTGCTGAGGG CACAAGAGAT ATGATAGCTG GTTTTCATCA ACCAAACGAT     240
CTTTCTTACT ATGGCTCATC TCTTTCGACG CTTAGCATGT GGTTATATAA CATTTTGCCA     300
TTTTCATTAG AAACTATACT TTTGTATATG AGTACATTTT TATCTCCACT CTTAGCTGTG     360
CCTTTGATAC TTATAGGTAA AGAACTAAAC GCTTCAAAAG CGGGTTTTAT AGCTGCACTT     420
CTAGCTATTA TTGCAAATAG TTATTATAAT AGAACAATGA GTGGATATTA CGATACGGAT     480
ATGCTAAATA TCACTCTTCC TATGATGGTT TTTTGGAGCA TAACAAGACT TGTTCAAAGA     540
AAAGAGAGAG TAAATTTAAT ATTTATTCCG GTTTTTATGG CGATATATGG ATGGTGGTAT     600
CCATCTTCTT ACTCACTATT ACTTGCCATG ATTGGAATGT TTTTTTTATA TACCATTGTT     660
TTTGAAAGAT ACGAAAAACT AAACTATGAA GCTATGGTTT TTATGATTTT AGCAATCACA     720
AGCTTTTCTA TACAAATTAA ATTTATTATA GTTATTGTTT TGTATGCTTT AATCTATTTT     780
TACCAAAGAT TTTTTGATAA AAAAGTAATA TTTGCATTAA TTATGGCTTC GTTAATATGC     840
TTTATATGGC TTGGCGGGCT AAACCCTATA CTTTTTAACA TTAAATTTTA TATATTTAGA     900
GACATTGCAG ATAGCGGTGA TGCTGTTTTT AAATTTTTCA ATGTAAATCA AACAATAAGA     960
GAAAGTTCTG CGATAGATTT TAACACAGTT GTAACTAGGA TTAGCGGGCA TTTAATAGTA    1020
TTTTTGGTAT CTATTATAGG ATATATTTTA TTTATAAAAA ACAATAAAAT TTTACTACTA    1080
ACTTTACCGA TTCTGTTTTT GGGTCTTATG TCATTTAAAA GTGGTTTAAG ATTTACAATA    1140
TACTCAGTTC CAGTAATGGC TCTTGGTTTT GGCTATTTTG TTATGTATTG TTTTGCAAAA    1200
ATAGATATAA AAGATCGTTT TTTAGGTTAT GTGTTTTTAT TTGTTGTAAC ATTTAGTGCA    1260
TTATATCCAT CTTTAAAACA TATTTATGAT TATAAAGTAT TTCCTGTTTT TACACATAGC    1320
GAAGTTGAAA GTTTGGATAA TTTAAAAAAT ATTGCAAAAA GAGAAGATTA TGTGCTTTCT    1380
TGGTGGGATT ATGGTTATCC GATCAGATAT TATTCAGATG TAAAAACTCT CATAGATGGA    1440
GGAAAACATC TTGGAAGTGA TAACTTCGCC GTTAGCTTTG CACTTGGAAG CGATCAAAAT    1500
AGCTCTGCAA ATATGGCAAG ATTAGAAGTT GAATATACAG AAAAAAATTA TGAAGAAAAA    1560
TTTGGATTAA ATTTAAAAAA GATGATGAAA GATTATAATG CTACAAATGT TAATGAGTTT    1620
TTATTATCAT TAAAAGATGA AAATTTAACT CTGCCAAAGC AAACAAGAGA TATTTATTAC    1680
TATTTACCAG ATAGAATGAT ATACATATAT CCGATAGTGC TAGATTTTTC TAGACTTGAT    1740
TTGACAACAG GGCAAGAATT TGCCCAGCCG TTTTTTATGG TTAGTGAGAG ATTTTCAGCT    1800
ACAAATGATA ATCAAATAAT GTTAAATAAC AATGTCATAT TAAGTAATGA TGGCACTAAA    1860
TTATCGATAA ATGGCAACTC TTATAGTGTA AATACATATG TTGAAACAAG TTATGATCAA    1920
AACGAAAAAT TAAATGTAAA TTATTTTAAC ATAGATCCAA ATAGCAATTT TTATGTGATT    1980
TTTATGAAAG ATTATTTGAG AATTTTGGTT TTAGATAAAA CTTTGTATGA TAGTGCGTAT    2040
ATTCAACTTT TTGTATTAGA AAATTATGAT AAAAATTTAT TTGAACCAGT GATTTTAAAC    2100
GGATCAACTA AAATTTATAA ACTCAAAAAA TGA
```

Figure 17: (SEQ ID NO 24)

```
MSNFNFAKFL NKLPRLSKHT ILMIVLAVCF GIFCRFYWVV WASAYPHFIW NDQLMISTND      60
GYAFAEGTRD MIAGFHQPND LSYYGSSLST LSMWLYNILP FSLETILLYM STFLSPLLAV     120
PLILIGKELN ASKAGFIAAL LAIIANSYYN RTMSGYYDTD MLNITLPMMV FWSITRLVQR     180
KERVNLIFIP VFMAIYGWWY PSSYSLLLAM IGMFFLYTIV FERYEKLNYE AMVFMILAIT     240
SFSIQIKFII VIVLYALIYF YQRFFDKKVI FALIMASLIC FIWLGGLNPI LFNIKFYIFR     300
DIADSGDAVF KFFNVNQTIR ESSAIDFNTV VTRISGHLIV FLVSIIGYIL FIKNNKILLL     360
TLPILFLGLM SFKSGLRFTI YSVPVMALGF GYFVMYCFAK IDIKDRFLGY VFLFVVTFSA     420
LYPSLKHIYD YKVFPVFTHS EVESLDNLKN IAKREDYVLS WWDYGYPIRY YSDVKTLIDG     480
GKHLGSDNFA VSFALGSDQN SSANMARLEV EYTEKNYEEK FGLNLKKMMK DYNATNVNEF     540
LLSLKDENLT LPKQTRDIYY YLPDRMIYIY PIVLDFSRLD LTTGQEFAQP FFMVSERFSA     600
TNDNQIMLNN NVILSNDGTK LSINGNSYSV NTYVETSYDQ NEKLNVNYFN IDPNSNFYVI     660
FMKDYLRILV LDKTLYDSAY IQLFVLENYD KNLFEPVILN GSTKIYKLKK
```

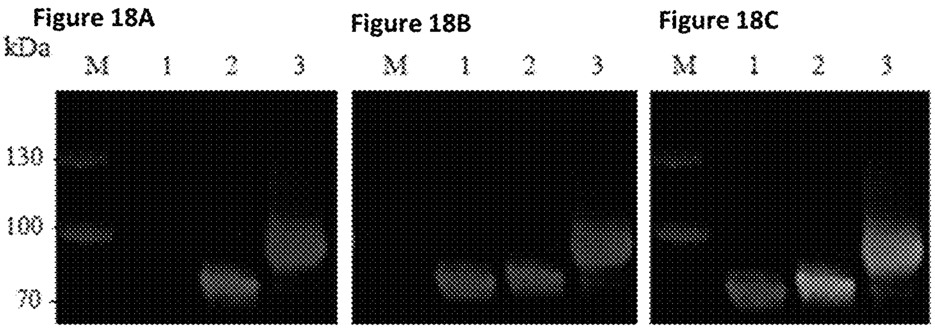
Figure 19A
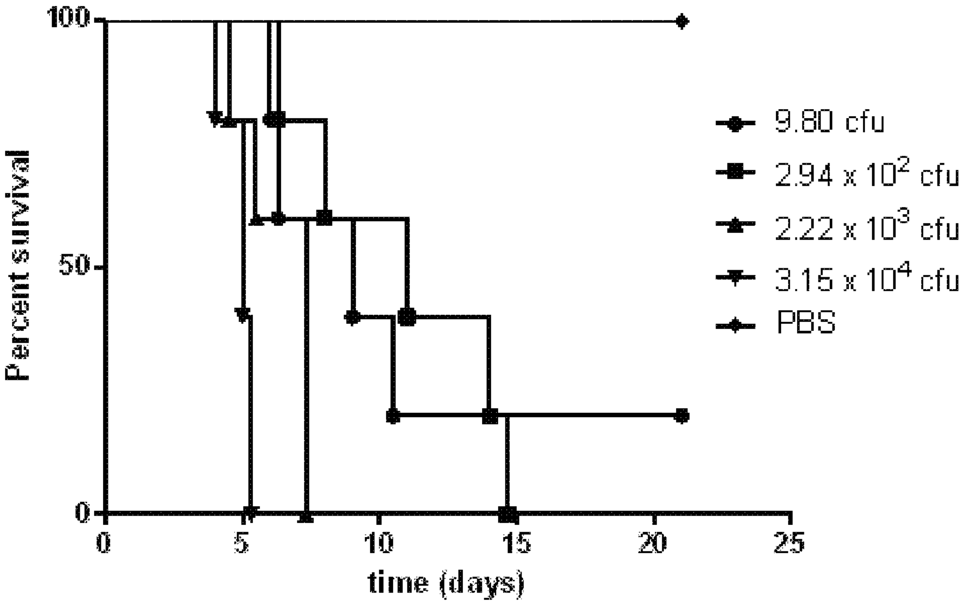

PBS
LVS 10^5
LVS 10^7

IFN+ IL17+
+ -
+ +
- +
% CD4 expressing cytokine
% CD8 expressing cytokine
LVS sonicate
FT sonicate
FT son.
Con-A

SEQUENCE LISTING

<160> NUMBER OF SEQ ID NOS: 35

<210> SEQ ID NO 1
<211> LENGTH: 211
<212> TYPE: PRT
<213> ORGANISM: Francisella tularensis

<400> SEQUENCE: 1

```
Met Ile Met Ser Glu Met Ile Thr Arg Gln Gln Val Thr Ser Gly Glu
1               5                   10                  15

Thr Ile His Val Arg Thr Asp Pro Thr Ala Cys Ile Gly Ser His Pro
            20                  25                  30

Asn Cys Arg Leu Phe Ile Asp Ser Leu Thr Ile Ala Gly Glu Lys Leu
        35                  40                  45

Asp Lys Asn Ile Val Ala Ile Asp Gly Gly Glu Asp Val Thr Lys Ala
    50                  55                  60

Asp Ser Ala Thr Ala Ala Ala Ser Val Ile Arg Leu Ser Ile Thr Pro
65                  70                  75                  80

Gly Ser Ile Asn Pro Thr Ile Ser Ile Thr Leu Gly Val Leu Ile Lys
                85                  90                  95

Ser Asn Val Arg Thr Lys Ile Glu Glu Lys Val Ser Ser Ile Leu Gln
            100                 105                 110

Ala Ser Ala Thr Asp Met Lys Ile Lys Leu Gly Asn Ser Asn Lys Lys
        115                 120                 125

Gln Glu Tyr Lys Thr Asp Glu Ala Trp Gly Ile Met Ile Asp Leu Ser
    130                 135                 140

Asn Leu Glu Leu Tyr Pro Ile Ser Ala Lys Ala Phe Ser Ile Ser Ile
145                 150                 155                 160

Glu Pro Thr Glu Leu Met Gly Val Ser Lys Asp Gly Met Arg Tyr His
                165                 170                 175

Ile Ile Ser Ile Asp Gly Leu Thr Thr Ser Gln Gly Ser Leu Pro Val
            180                 185                 190

Cys Cys Ala Ala Ser Thr Asp Lys Gly Val Ala Lys Ile Gly Tyr Ile
        195                 200                 205

Ala Ala Ala
    210
```

<210> SEQ ID NO 2
<211> LENGTH: 642
<212> TYPE: PRT
<213> ORGANISM: Francisella tularensis

<400> SEQUENCE: 2

```
Met Gly Lys Ile Ile Gly Ile Asp Leu Gly Thr Thr Asn Ser Cys Leu
1               5                   10                  15

Ala Ile Met Asp Gly Lys Thr Ala Lys Val Ile Glu Asn Ala Glu Gly
            20                  25                  30

His Arg Thr Thr Pro Ser Val Val Ala Tyr Thr Asp Ser Gly Glu Ile
        35                  40                  45

Leu Val Gly Gln Ala Ala Lys Arg Gln Ala Val Thr Asn Pro Asp Asn
    50                  55                  60

Thr Phe Phe Ala Ile Lys Arg Leu Ile Gly Arg Lys Tyr Asp Asp Lys
65                  70                  75                  80

Ala Val Gln Glu Asp Ile Lys Lys Lys Val Pro Tyr Ala Val Ile Lys
                85                  90                  95

Ala Asp Asn Gly Asp Ala Trp Val Ala Thr Lys Glu Gly Lys Lys Met
```

-continued

```
            100                 105                 110

Ala Pro Pro Gln Val Ser Ala Glu Val Leu Arg Lys Met Lys Lys Thr
        115                 120                 125

Ala Glu Asp Tyr Leu Gly Glu Pro Val Thr Glu Ala Val Ile Thr Val
    130                 135                 140

Pro Ala Tyr Phe Asn Asp Ser Gln Arg Gln Ala Thr Lys Asp Ala Gly
145                 150                 155                 160

Lys Ile Ala Gly Leu Glu Val Lys Arg Ile Ile Asn Glu Pro Thr Ala
                165                 170                 175

Ala Ala Leu Ala Tyr Gly Val Asp Ser Lys Lys Gly Glu Gln Thr Val
            180                 185                 190

Ala Val Tyr Asp Leu Gly Gly Gly Thr Phe Asp Ile Ser Ile Ile Glu
        195                 200                 205

Ile Ala Asp Val Asp Gly Asp Asn Gln Ile Glu Val Leu Ser Thr Asn
    210                 215                 220

Gly Asp Thr Phe Leu Gly Gly Glu Asp Phe Asp Leu Ala Leu Met Asn
225                 230                 235                 240

Tyr Leu Ile Asp Glu Phe Lys Lys Glu Gln Gly Ile Asp Leu His Asn
                245                 250                 255

Asp Lys Leu Ala Leu Gln Arg Val Arg Glu Ala Ala Glu Lys Ala Lys
            260                 265                 270

Val Glu Leu Ser Ser Ala Gln Gln Thr Asp Val Asn Leu Pro Tyr Ile
        275                 280                 285

Thr Ala Asp Ala Thr Gly Pro Lys His Leu Asn Ile Lys Val Thr Arg
    290                 295                 300

Ala Lys Phe Glu Ser Leu Val Ser Asp Leu Val Met Arg Ser Leu Glu
305                 310                 315                 320

Pro Cys Lys Lys Ala Leu Glu Asp Ala Gly Leu Ser Lys Ser Asp Ile
                325                 330                 335

Thr Glu Val Leu Leu Val Gly Gly Gln Thr Arg Met Pro Leu Val Gln
            340                 345                 350

Glu Lys Val Lys Glu Phe Phe Gly Lys Glu Pro Arg Lys Asp Val Asn
        355                 360                 365

Pro Asp Glu Ala Val Ala Val Gly Ala Ala Ile Gln Gly Gly Val Leu
    370                 375                 380

Ala Gly Asp Val Lys Asp Ile Leu Leu Leu Asp Val Thr Pro Leu Ser
385                 390                 395                 400

Leu Gly Ile Glu Thr Met Gly Gly Val Met Thr Lys Leu Ile Glu Arg
                405                 410                 415

Asn Thr Thr Ile Pro Thr Lys Lys Ser Gln Val Phe Ser Thr Ala Glu
            420                 425                 430

Asp Asn Gln Pro Ala Val Thr Ile His Val Leu Gln Gly Glu Arg Glu
        435                 440                 445

Met Ala Ser Ala Asn Lys Ser Leu Gly Arg Phe Asp Leu Ala Asp Ile
    450                 455                 460

Pro Pro Ala Pro Arg Gly Met Pro Gln Ile Glu Val Thr Phe Asp Ile
465                 470                 475                 480

Asp Ala Asn Gly Ile Leu Asn Val Ser Ala Lys Asp Lys Ala Thr Gly
                485                 490                 495

Lys Glu Gln Asn Ile Val Ile Lys Ser Ser Ser Gly Leu Ser Glu Glu
            500                 505                 510

Asp Ile Glu Lys Met Val Gln Asp Ala Glu Ala Asn Ala Glu Ala Asp
        515                 520                 525
```

Lys Lys Phe His Asp Leu Val Thr Ala Arg Asn Thr Ala Asp Asn Leu
530 535 540

Ile His Ser Ser Arg Lys Ala Ile Gln Glu Leu Gly Asp Lys Val Thr
545 550 555 560

Ala Ala Glu Lys Glu Lys Ile Glu Glu Ala Cys Lys Glu Leu Glu Ala
565 570 575

Ala Thr Lys Gly Asp Asp Lys Gln Ala Ile Glu Ser Lys Thr Lys Ala
580 585 590

Leu Glu Glu Ala Phe Ala Pro Ile Ala Gln Lys Ala Tyr Ala Glu Gln
595 600 605

Ala Gln Ala Ala Val Ala Gln Gly Gly Ala Lys Ala Glu Glu Pro Lys
610 615 620

Lys Glu Glu Asp Val Val Asp Ala Asp Phe Glu Asp Val Glu Asp Asp
625 630 635 640

Lys Lys

<210> SEQ ID NO 3
<211> LENGTH: 697
<212> TYPE: PRT
<213> ORGANISM: Pseudomonas aeruginosa

<400> SEQUENCE: 3

Met Lys Lys Ile Trp Leu Ala Leu Ala Gly Leu Val Leu Ala Phe Ser
1 5 10 15

Ala Ser Asp Gln Asn Ala Thr Gly Gly Asp Gln Asn Ala Thr Gly Gly
20 25 30

Asp Gln Asn Ala Thr Gly Gly Asp Gln Asn Ala Thr Ala Ala Glu Glu
35 40 45

Ala Phe Asp Leu Trp Asn Glu Cys Ala Lys Ala Cys Val Leu Asp Leu
50 55 60

Lys Asp Gly Val Arg Ser Ser Arg Met Ser Val Asp Pro Ala Ile Ala
65 70 75 80

Asp Thr Asn Gly Gln Gly Val Leu His Tyr Ser Met Val Leu Glu Gly
85 90 95

Gly Asn Asp Ala Leu Lys Leu Ala Ile Asp Asn Ala Leu Ser Ile Thr
100 105 110

Ser Asp Gly Leu Thr Ile Arg Leu Glu Gly Gly Val Glu Pro Asn Lys
115 120 125

Pro Val Arg Tyr Ser Tyr Thr Arg Gln Ala Arg Gly Ser Trp Ser Leu
130 135 140

Asn Trp Leu Val Pro Ile Gly His Glu Lys Pro Ser Asn Ile Lys Val
145 150 155 160

Phe Ile His Glu Leu Asn Ala Gly Asn Gln Leu Ser His Met Ser Pro
165 170 175

Ile Tyr Thr Ile Glu Met Gly Asp Glu Leu Leu Ala Lys Leu Ala Arg
180 185 190

Asp Ala Thr Phe Phe Val Arg Ala His Glu Ser Asn Glu Met Gln Pro
195 200 205

Thr Leu Ala Ile Ser His Ala Gly Val Ser Val Val Met Ala Gln Ala
210 215 220

Gln Pro Arg Arg Glu Lys Arg Trp Ser Glu Trp Ala Ser Gly Lys Val
225 230 235 240

Leu Cys Leu Leu Asp Pro Leu Asp Gly Val Tyr Asn Tyr Leu Ala Gln
245 250 255

-continued

```
Gln Arg Cys Asn Leu Asp Asp Thr Trp Glu Gly Lys Ile Tyr Arg Val
            260                 265                 270

Leu Ala Gly Asn Pro Ala Lys His Asp Leu Asp Ile Lys Asp Asn Asn
        275                 280                 285

Asn Ser Thr Pro Thr Val Ile Ser His Arg Leu His Phe Pro Glu Gly
    290                 295                 300

Gly Ser Leu Ala Ala Leu Thr Ala His Gln Ala Cys His Leu Pro Leu
305                 310                 315                 320

Glu Ala Phe Thr Arg His Arg Gln Pro Arg Gly Trp Glu Gln Leu Glu
                325                 330                 335

Gln Cys Gly Tyr Pro Val Gln Arg Leu Val Ala Leu Tyr Leu Ala Ala
            340                 345                 350

Arg Leu Ser Trp Asn Gln Val Asp Gln Val Ile Arg Asn Ala Leu Ala
        355                 360                 365

Ser Pro Gly Ser Gly Gly Asp Leu Gly Glu Ala Ile Arg Glu Gln Pro
    370                 375                 380

Glu Gln Ala Arg Leu Ala Leu Thr Leu Ala Ala Ala Glu Ser Glu Arg
385                 390                 395                 400

Phe Val Arg Gln Gly Thr Gly Asn Asp Glu Ala Gly Ala Ala Ser Ala
                405                 410                 415

Asp Val Val Ser Leu Thr Cys Pro Val Ala Lys Asp Gln Asn Arg Thr
            420                 425                 430

Lys Gly Glu Cys Ala Gly Pro Ala Asp Ser Gly Asp Ala Leu Leu Glu
        435                 440                 445

Arg Asn Tyr Pro Thr Gly Ala Glu Phe Leu Gly Asp Gly Gly Asp Val
    450                 455                 460

Ser Phe Ser Thr Arg Gly Thr Gln Asn Trp Thr Val Glu Arg Leu Leu
465                 470                 475                 480

Gln Ala His Arg Gln Leu Glu Glu Arg Gly Tyr Val Phe Val Gly Tyr
                485                 490                 495

His Gly Thr Phe Leu Glu Ala Ala Gln Ser Ile Val Phe Gly Gly Val
            500                 505                 510

Arg Ala Arg Ser Gln Asp Leu Asp Ala Ile Trp Arg Gly Phe Tyr Ile
        515                 520                 525

Ala Gly Asp Pro Ala Leu Ala Tyr Gly Tyr Ala Gln Asp Gln Glu Pro
    530                 535                 540

Asp Ala Arg Gly Arg Ile Arg Asn Gly Ala Leu Leu Arg Val Tyr Val
545                 550                 555                 560

Pro Arg Trp Ser Leu Pro Gly Phe Tyr Arg Thr Gly Leu Thr Leu Ala
                565                 570                 575

Ala Pro Glu Ala Ala Gly Glu Val Glu Arg Leu Ile Gly His Pro Leu
            580                 585                 590

Pro Leu Arg Leu Asp Ala Ile Thr Gly Pro Glu Glu Glu Gly Gly Arg
        595                 600                 605

Val Thr Ile Leu Gly Trp Pro Leu Ala Glu Arg Thr Val Val Ile Pro
    610                 615                 620

Ser Ala Ile Pro Thr Asp Pro Arg Asn Val Gly Gly Asp Leu Asp Pro
625                 630                 635                 640

Ser Ser Ile Pro Asp Lys Glu Gln Ala Ile Ser Ala Leu Pro Asp Tyr
                645                 650                 655

Ala Ser Gln Pro Gly Lys Pro Pro Arg Glu Asp Leu Lys Asp Gln Asn
            660                 665                 670
```

-continued

```
Ala Thr Gly Gly Asp Gln Asn Ala Thr Gly Gly Asp Gln Asn Ala Thr
        675                 680                 685

Gly Gly Asp Gln Asn Ala Thr Val Asp
    690                 695


<210> SEQ ID NO 4
<211> LENGTH: 149
<212> TYPE: PRT
<213> ORGANISM: Francisella tularensis

<400> SEQUENCE: 4

Met Lys Lys Ile Ile Lys Leu Ser Leu Leu Ser Leu Ser Ile Ala Gly
1               5                   10                  15

Leu Ala Ser Cys Ser Thr Leu Gly Leu Gly Gly Ser Asp Asp Ala Lys
            20                  25                  30

Ala Ser Ala Lys Asp Thr Ala Ala Ala Gln Thr Ala Thr Thr Glu Gln
        35                  40                  45

Ala Ala Ala Val Ser Lys Pro Thr Ala Lys Val Ser Leu Asn Lys Leu
    50                  55                  60

Gly Gln Asp Lys Ile Lys Ala Thr Val Tyr Thr Ala Tyr Asn Asn Asn
65                  70                  75                  80

Pro Gln Gly Ser Val Arg Leu Gln Trp Gln Ala Pro Glu Gly Ser Lys
                85                  90                  95

Cys His Asp Thr Ser Phe Pro Ile Thr Lys Tyr Ala Glu Lys Asn Asp
            100                 105                 110

Lys Thr Trp Ala Thr Val Thr Val Lys Gln Gly Asn Asn Phe Cys Ser
        115                 120                 125

Gly Lys Trp Thr Ala Asn Val Val Tyr Asp Lys Glu Val Ile Ala Ser
    130                 135                 140

Asp Ser Ile Asn Ile
145


<210> SEQ ID NO 5
<211> LENGTH: 514
<212> TYPE: PRT
<213> ORGANISM: Francisella tularensis

<400> SEQUENCE: 5

Met Val Ser Arg Glu Asp Phe Ile Met Thr Ile Asn Lys Leu Ser Leu
1               5                   10                  15

Thr Asp Glu Leu Leu Asn Asn Phe Gly Gly Ser Thr Glu Val Asp Ser
            20                  25                  30

Val Leu Lys Asn Ile Asp Phe Asp Val Ser Asp Asp Ala Ser Lys Val
        35                  40                  45

Leu Ser Leu Ser Thr Asp Tyr Asn Ala Arg Asn Leu Met Ala Leu Ser
    50                  55                  60

Leu Val Leu Ala Asn Asn Asp Asn Ile Asn Asn Tyr Asn Gln Lys Tyr
65                  70                  75                  80

Ile Gln Lys Val Ile Thr Val Ile Asp Lys Leu Ile Asp Leu Gln Val
                85                  90                  95

Asn Ser Ile Ile Ser Asn Asp Glu Phe Arg Ala Leu Glu Gln Glu Trp
            100                 105                 110

Leu Lys Val Gln Glu Val Cys Gln Glu Asp Tyr Asp Asn Val Glu Val
        115                 120                 125

Ser Ile Leu Asp Val Lys Lys Glu Glu Leu Gln Tyr Asp Phe Glu Arg
    130                 135                 140
```

-continued

```
Asn Leu Tyr Asp Ile Ser Ser Ser Asp Phe Phe Lys Lys Val Tyr Val
145                 150                 155                 160

Ser Glu Phe Asp Gln Tyr Gly Gly Glu Pro Tyr Gly Ala Ile Leu Gly
                165                 170                 175

Leu Tyr Asn Phe Glu Asn Thr Thr Asn Asp Ile Ile Trp Leu Thr Gly
            180                 185                 190

Met Gly Met Val Ala Lys Asn Ser His Ala Pro Phe Ile Ala Ser Ile
        195                 200                 205

Asp Lys Ser Phe Phe Gly Val Lys Asp Leu Ser Glu Ile Thr His Ile
    210                 215                 220

Lys Ser Phe Glu Ala Leu Leu Glu His Pro Arg Tyr Lys Glu Trp Asn
225                 230                 235                 240

Asp Phe Arg Asn Leu Asp Val Ala Ala Tyr Ile Gly Leu Thr Val Gly
                245                 250                 255

Asp Phe Met Leu Arg Gln Pro Tyr Asn Pro Glu Asn Asn Pro Val Gln
            260                 265                 270

Tyr Lys Leu Met Glu Gly Phe Asn Glu Phe Val Asp Tyr Asp Lys Asn
        275                 280                 285

Glu Ser Tyr Leu Trp Gly Pro Ala Ser Ile His Leu Val Lys Asn Met
    290                 295                 300

Met Arg Ser Tyr Asp Lys Thr Arg Trp Phe Gln Tyr Ile Arg Gly Val
305                 310                 315                 320

Glu Ser Gly Gly Tyr Val Lys Asn Leu Val Ala Cys Val Tyr Asp Asn
                325                 330                 335

Lys Gly Ile Leu Glu Thr Lys Ser Pro Leu Asn Val Leu Phe Ala Asp
            340                 345                 350

Tyr Met Glu Leu Ser Leu Ala Asn Ile Gly Leu Ile Pro Phe Val Ser
        355                 360                 365

Glu Lys Gly Thr Ser Asn Ala Cys Phe Phe Ser Val Asn Ser Ala Lys
    370                 375                 380

Lys Val Glu Glu Phe Val Asp Gly Phe Asp Ser Ala Asn Ser Arg Leu
385                 390                 395                 400

Ile Ala Asn Leu Ser Tyr Thr Met Cys Ile Ser Arg Ile Ser His Tyr
                405                 410                 415

Ile Lys Cys Val Ile Arg Asp Lys Ile Gly Ser Ile Val Asp Val Glu
            420                 425                 430

Ser Ile Gln Lys Ile Leu Ser Asp Trp Ile Ser Glu Phe Val Thr Thr
        435                 440                 445

Val Tyr Gln Pro Thr Pro Leu Glu Met Ala Arg Tyr Pro Phe Arg Asn
    450                 455                 460

Val Ser Ile Glu Val Glu Thr Ile Pro Gly Lys Pro Gly Trp Tyr Ser
465                 470                 475                 480

Cys Lys Ile Asn Val Ile Pro His Ile Gln Phe Glu Gly Met Asn Thr
                485                 490                 495

Thr Met Thr Ile Asp Thr Arg Leu Glu Pro Glu Leu Phe Gly Thr Asn
            500                 505                 510

Asn Asn
```

```
<210> SEQ ID NO 6
<211> LENGTH: 95
<212> TYPE: PRT
<213> ORGANISM: Francisella tularensis

<400> SEQUENCE: 6
```

```
Met Asn Ile Arg Pro Leu Gln Asp Arg Val Leu Val Arg Arg Ala Glu
1               5                   10                  15

Glu Glu Lys Lys Ser Ala Gly Gly Ile Ile Leu Thr Gly Ser Ala Gln
            20                  25                  30

Glu Lys Pro Ser Gln Gly Glu Val Val Ala Val Gly Asn Gly Lys Lys
        35                  40                  45

Leu Asp Asn Gly Thr Thr Leu Pro Met Asp Val Lys Val Gly Asp Lys
    50                  55                  60

Val Leu Phe Gly Lys Tyr Ser Gly Ser Glu Val Lys Val Gly Asp Glu
65                  70                  75                  80

Thr Leu Leu Met Met Arg Glu Glu Asp Ile Met Gly Ile Ile Ala
                85                  90                  95


<210> SEQ ID NO 7
<211> LENGTH: 544
<212> TYPE: PRT
<213> ORGANISM: Francisella tularensis

<400> SEQUENCE: 7

Met Ala Ala Lys Gln Val Leu Phe Ser Asp Glu Ala Arg Ala Lys Met
1               5                   10                  15

Leu Asp Gly Val Asn Thr Leu Ala Asn Ala Val Lys Val Thr Leu Gly
            20                  25                  30

Pro Lys Gly Arg Asn Val Val Leu Asp Lys Ser Phe Gly Thr Pro Thr
        35                  40                  45

Ile Thr Lys Asp Gly Val Ser Val Ala Lys Glu Ile Glu Leu Glu Asp
    50                  55                  60

Lys Phe Glu Asn Met Gly Ala Gln Ile Val Lys Glu Val Ala Ser Lys
65                  70                  75                  80

Thr Ala Asp Val Ala Gly Asp Gly Thr Thr Thr Ala Thr Val Leu Ala
                85                  90                  95

Gln Ala Leu Leu Thr Glu Gly Leu Lys Ala Val Ala Ala Gly Met Asn
            100                 105                 110

Pro Met Asp Leu Lys Arg Gly Ile Asp Lys Ala Thr Ala Arg Leu Val
        115                 120                 125

Glu Glu Leu Lys Ala Leu Ser Lys Pro Cys Ser Asp Pro Lys Ser Ile
    130                 135                 140

Glu Gln Val Gly Thr Ile Ser Ala Asn Ser Asp Ala Thr Val Gly Lys
145                 150                 155                 160

Leu Ile Ala Asp Ala Met Ala Lys Val Gly Lys Glu Gly Val Ile Thr
                165                 170                 175

Val Glu Glu Gly Lys Gly Phe Glu Asp Glu Leu Asp Val Val Glu Gly
            180                 185                 190

Met Gln Phe Asp Arg Gly Tyr Leu Ser Pro Tyr Phe Ala Thr Asn Gln
        195                 200                 205

Glu Asn Met Thr Thr Asp Leu Glu Asn Pro Tyr Ile Leu Ile Val Asp
    210                 215                 220

Lys Lys Ile Ser Asn Ile Arg Asp Leu Leu Pro Ile Leu Glu Gly Val
225                 230                 235                 240

Ser Lys Ser Gly Arg Ala Leu Leu Ile Ile Ala Glu Asp Val Glu Ser
                245                 250                 255

Glu Ala Leu Ala Thr Leu Val Val Asn Asn Met Arg Gly Val Val Lys
            260                 265                 270

Val Cys Ala Val Lys Ala Pro Gly Phe Gly Asp Arg Arg Lys Ala Met
        275                 280                 285
```

-continued

```
Leu Glu Asp Ile Ala Thr Leu Thr Gly Ala Thr Phe Val Ser Glu Asp
    290                 295                 300

Leu Ser Met Lys Leu Glu Glu Thr Asn Met Glu His Leu Gly Thr Ala
305                 310                 315                 320

Ser Arg Val Gln Val Thr Lys Asp Asn Thr Thr Ile Ile Asp Gly Ala
                325                 330                 335

Gly Glu Lys Glu Ala Ile Ala Lys Arg Ile Asn Val Ile Lys Ala Asn
            340                 345                 350

Ile Ala Glu Ala Asn Ser Asp Tyr Asp Arg Glu Lys Leu Gln Glu Arg
        355                 360                 365

Leu Ala Lys Leu Ser Gly Gly Val Ala Val Ile Lys Val Gly Ala Val
    370                 375                 380

Thr Glu Ala Glu Met Lys Glu Lys Lys Asp Arg Val Asp Asp Ala Leu
385                 390                 395                 400

His Ala Thr Arg Ala Ala Val Glu Glu Gly Ile Val Ala Gly Gly Gly
                405                 410                 415

Val Ala Leu Ile Arg Ala Gln Lys Ala Leu Asp Gly Leu Thr Gly Glu
            420                 425                 430

Asn Asp Asp Gln Asn Tyr Gly Ile Ala Leu Leu Arg Lys Ala Ile Glu
        435                 440                 445

Ala Pro Leu Arg Gln Ile Val Ser Asn Ala Gly Gly Glu Ser Ser Val
    450                 455                 460

Val Val Asn Gln Val Lys Ala Asn Gln Gly Asn Tyr Gly Tyr Asn Ala
465                 470                 475                 480

Ala Asn Asp Thr Tyr Gly Asp Met Val Glu Met Gly Ile Leu Asp Pro
                485                 490                 495

Thr Lys Val Thr Arg Ser Ala Leu Gln His Ala Ala Ser Ile Ala Gly
            500                 505                 510

Leu Met Ile Thr Thr Glu Ala Met Ile Gly Glu Ile Lys Glu Ala Ala
        515                 520                 525

Pro Ala Met Pro Met Gly Gly Gly Met Gly Gly Met Pro Gly Met Met
    530                 535                 540
```

```
<210> SEQ ID NO 8
<211> LENGTH: 21682
<212> TYPE: DNA
<213> ORGANISM: Francisella tularensis

<400> SEQUENCE: 8

ttaactactt gtatctagtc taacaatatc gtcttcactt atatattctc caacttgtac      60

ttctataaga ataactggaa tcttgccatt attttcaagt ctgtgagatt cgcctatttt     120

tatatataca gactcatttg gtctaacaat agacttagta gtaccaatag ttaccgtagc     180

agttccagaa atcacaatcc aatgctcact acggtgataa tgttgctgta atgataactt     240

cttgcccggt tcaagttgaa tcgcctgtat cttataacca gacttatcct ctaatattgt     300

cgctgaaccc caaggtttat aaatttgctt atgctgtaat aattcacttc gctgctgaat     360

tttcaaaact tcgactattt ttttgacatc ttgagttttg ttcttatccg cgacaagtat     420

agcatctgct gtttcaacaa ttattaaatc attaactccg actgcagcca ataaacgatc     480

atgcgagcgt aaataactat ttttgacatt actagtaatc acatcgccaa taaccacatt     540

accacaacta tcttttgcag caatatcata caaagagtcc caagagccaa catcagacca     600

gccactttgt tgcataggca ctatagcaac attagttgct ttctccataa ctgcgtagtc     660
```

-continued

```
tattgactgt gattgaacta gggcaaagct ttgtttatca aaacgcacaa aatctaaatc    720
ctgctgtgac ttttgataag ttttttcaca tcctctgtaa atctctggct gtaacttctc    780
taaaacctct aaatacactc tagctgtgaa cataaacata ccgctattcc aatagtattt    840
gccactatct aaatactctt gtgcaacgac cacactaggc ttctcaacaa atttatctac    900
cttataaact ccatttacag tagtctgtac cccttgttta atataaccat agccttcatg    960
aggacaagtt ggtgtaatgc caaaggtaac taaagaatca tctttaataa ctttttgctg   1020
tgctttttcg atagcttgat gaaaaatctc cagattttca atatgatggt cagcagctaa   1080
aactagcata attgtatttg gatcattaat agctaaatgt agtgctgcaa gtgcaattgc   1140
tggagcagta tttctggcta atggctctag gagtatatcg cctttttat tgattttccg   1200
caacacttca gcaacttgga atctatgact ttcattacag acaactacag gtgaagttat   1260
atccttgaca ttatctagtc gcttaattgt attttctaat agactatgtt catcaaccaa   1320
gccgataaac tgctttggcg atgcctctcg tgatagtggc catagccttg agccgaatcc   1380
tccagataag ataataggag taatcattat aaaaacctaa ataactttga tattgattaa   1440
ttatatagaa agctaatata ttcaacaata aatcagcaaa ttaaatattg tcataactta   1500
acttactaaa tttagatagt aggtttataa taggatctct aaaaattacc tttgtatgtt   1560
tgtttagata atatttgtag caaaccttat acaaagtaga gcatcattat gtcagttttg   1620
accagagaat accaagaata ttttagcagc atgatatagt taatccgaga gtattttgtt   1680
aaacacataa gagatagcat cacaaaattt ttcaaaacta ttattcactt ttctaaatat   1740
tttttaata gttagcccaa acctttcaa taggatttaa atctggagag tacggaggta   1800
gatataatat ttgtacatca aatttattgg ctatttcttt tagtttttct atatactcca   1860
acctttcatg ttcttttctt tgcttatatt ttggagtctt tttttaaaac taaaaccaag   1920
tctattaaga caatcataaa atgtacttct tggaatatca ggggctaatg cttcttttat   1980
atctaatgca cttgcatctg gatgatctat caaatactgt tcaatcaatg ttttatcggt   2040
aaagctagcg actctgccac aaccaactcc ttgctttgaa ctataatctc cggttctttt   2100
ataaaactct atccatgaaa caactgtacg cttatctatg ttaaaaaact tactcagctc   2160
gaactccgtc ataccttctt catgtttatt aattacgatg tctctaaaat cttggctata   2220
tgatggcatt tttattagac attataacat ttctacaaat atctttttct acaaatatct   2280
ttcggattaa ctatattctt gcgaacacta ctttttaaca caaaaataaa ttaaattgat   2340
tttttagaga tactcataag ataaatattt aagctataga taaaactcaa tagtttgtct   2400
aaacatctta tcaaaatctt gtgatggctt ccatcctaac tcattctgaa tcttgctgtt   2460
atcaatagca taacgccaat catgtccttt tctatcttcc acaaatgtga ttaagttaga   2520
atgtggagca ttttctggtt tatattcatc cattagttta cagatagttt ttaccaaggt   2580
tagattatca acttcattaa taccaccaat attataaacc tctccaacca ctcctttctc   2640
aacaattgtc tggatagcat cgcagtgatc ttctacatat agccaatctc gaatattcga   2700
accatctccg taaacaggaa taggcttgta gtttatacaa ctatttatca ctacagggat   2760
taatttctct cgatgttggt atggtccata gttgtttgaa caatttgaaa ttgttaccgg   2820
aagtttatag gtatgatgat atgctctaga aatatgatca gatcccgcct tagatgccga   2880
atacggtgaa tttggctcat aagccttaat ctcagtaaag gctggttcat cttttgccaa   2940
ggtaccatat acctcatcag tagatacatg atgaaaccta caactagttt cttctaaacc   3000
tagctcatct aaccaatacc ttttagcaca atctaaaagt gtaaatgtac ctatcacatt   3060
```

-continued

```
cgtttctaaa aatacctttg gattagcaat tgaattatca acatgcgatt ctgcagcaaa   3120
atgtactatc gtatcaattt tatattcttt cagtgtttga tatactaaaa cttcatcaca   3180
aatatcacct tttataaaag tatggttatg ttcattattc aagtctttta gattatctaa   3240
actacccgca taagtaagct tatcatacga gattattttg atatcactat agcgtgataa   3300
catcatacgc acatagttac taccaataaa tcccgccgca cctgttacta ggatattttt   3360
tggtttgtag ttcatttttt cattcctcat tacatcatca ttcctatagt gactagtcat   3420
tctctcacta aactatcatt accgcataaa cttgtcatta ccgcgtaggc ggtaatctcc   3480
caatcacatc tgatatttag agatacctat ctgcaccagt aagacaaaag ttttactcac   3540
atattaattc atataaatca ttccaattcg gattcatctc attaataatt cgttctttcc   3600
aagatctgtt tcattttttc aactgctttt ctcacagaat tgctgctttt atatcttcat   3660
aaatttcaaa ataaactaac ttattaacat tatattttta gtaaaaccat ctgcaaggct   3720
atgtttatgc tcatacattc tttttatcaa attagatgtt acaactatgt acagaacagt   3780
attatcctta tttgtaagaa tatacataaa accattttta gtcattgtaa aacatcgcta   3840
tatattacca aacctgtcat tactgcgcag attggaatct ccaaaacata tccaactttt   3900
atgagatacc caccttcatg ggtatgacgg attaatttat aaaccatcct taattaaatt   3960
cttcagatac tgaccatact ctgtcttaga aagtttttca gcttgagcta gaacttgttg   4020
tgttgagata aagcctttac gccatgcaat ttcttccaaa catgcaattt taagcccttg   4080
tcttttctca atagttgcga catattgacc tgcctctagc aatgaatcat gcgtaccagc   4140
atcaagccaa gcaaagccac gccctaagag ttcgacattt agcttatttt cttttagata   4200
taactcatta agtgaagtaa tctctagctc accacgtgca gatggtttga cttgtttagc   4260
atactcaaca acattattat cataaaaata taaacctgtg atagcatagt gtgacttagg   4320
attctgtggc ttttcctcta ccgaaattac atttttttgc ttatcaaatt cgactatacc   4380
atatctatgc ggatcattaa cataataacc aaaaacacaa gcgccaccag ctggacctcc   4440
acactgtgct cttgcagact ctagcattgt agtcatacct tgaccatagt agatattatc   4500
tcctaatatc aaacaagctg agtcacccgc caaaaactcc tcaccaagaa taaatgcttg   4560
agcaagccca tctggtgatg gctggatttt ataactcaac tgtataccaa attgtgaacc   4620
atcaccaaga agctcttgga taagtgagat atcacgcact gtagagataa ttaatatctc   4680
cctaatacct gcaagcataa gcacagatag tggatagtat aacaatggct tgtcataaac   4740
aggtagcagc tgtttgctaa cacccaaggt aagtggatat agccttgtac cactgccacc   4800
agctagaatt attcccttca tttcacataa tcctctaaat gatatttatt tttcaaatct   4860
atatttaaac caacttacta atggaataca tcttgatcta attaaaattt tgaatagacg   4920
aatagcacta ataaaacatc tccctttaat agccgaaatt atcatttgca caacagggat   4980
acaaatattt aatttctctt caggatatct atccaaaaaa tattcaaata atccagcata   5040
agtattatag attttttcct tagacttaga tgtgatacca ataccttttc tgtacacact   5100
ataggattca ttagaattta aaaaacttaa ataacctttt tctgctgtta taacatgaaa   5160
ataataatct agaagctcta tatccggtaa aatcaaatca tccaaaaccg atgttctgaa   5220
catttttgaa ctatttgcac caacagcaac tccgcgtaaa gtgtctgata aattgaatat   5280
actcttattt gaacaagcaa acctactatg ttgtatatta ccatttggat agagtatatt   5340
tatattatga aaaactcccg tacatcttgg attattatcc aaaaaatcag cctgaatttg   5400
```

-continued

```
aagtttacca ggcaatgcat aatcatcacc atccatatga gctatatact caccatttgc   5460
aacaaaatag atttctttaa tattttcagt aattcccaca ttcttatctc taaaaactgg   5520
ctttatgata tccggatact tttttgata ctcttgaata acatctcttg taccatctgt   5580
agaaaaatca tctccaacga ttatctcaaa gtcaaaatca gtctcttgag taaccaaaga   5640
ctctaaacat tgaccaatat acttttcttg attgtatgtc atcacacata ctgaaacttt   5700
aatcatctat acacctcaaa accttgtacc gaaacaaaac atactctata caaatttgta   5760
taaataaaaa tgcaaaccca atcaatatta attctaccaa cccaatttta cttggataaa   5820
tataccaacc cttaaatatt aacgataata aaaaacatac tatagtaata actgctaaat   5880
ttataaaaaa atacctattg atacctttag caaatacatg gtgtacaata ggcatccaga   5940
ttatcagccc cactatagca tatccaagcc ataatagtgc tgtagtatac actccataat   6000
tataagcagt atatataact ataggagcaa aaaatactaa actaattgta ttatatgtat   6060
tatgtagctt taacttacca taagcatact gtaaaaaata ttgaaatgat attatacaaa   6120
taatagatgc tgataaaaca tatatattta agatattact accccaatta gcaatttcca   6180
tacttcctgt ccatgactgc aacagctgat gagaatacat caaaacacat gttactacag   6240
cagataaaaa agtaattgag atcaaggatg attttaaata taagctttcc attcctttta   6300
cattttgttg ggctaatagc attgtcattc taggctgaat agctatgcta atcggagagg   6360
acaatatcgt aacagcacta gatatcacta tcaataaaga taaataacca tactcagata   6420
atggtaatac atgtgagaac actaatttat cagattgagt gacaataatc caaactgttg   6480
tagaatatgc aatgcctagt gcaaatggaa gcacttttct aattatttta aaatcaaacc   6540
ttaaacccac gctaaatgat gatggtagta ttttataaaa tgcaattgca atacatacta   6600
gatatagtat cgcaattatt gtctgatata caaaataata cataatatta gtagacacat   6660
agcagataaa taataatcca ccaataaact gtagtgtcgt ttgtatgata cttaaattat   6720
tataaagaac ctgtctttca aagccacgca aaccaccacc atatagatca gacacccatc   6780
ttaatgcaaa cattaaaccc ataagtgcaa tacatacact tacactatca gcatctagcg   6840
agcctatatg taaccaagag gtggatatat accttgaatg tgtactaatt acaataaata   6900
ccagaacacc aacaataatg aaaaatagct ctaacgatct aaccaacttg cgtaagtaat   6960
gatagtcatc agtactacct ctaacatgag ccacttctct tgataaagtt ggtgttatac   7020
caacatccaa caaccgtaac cacgtttgaa aaactgtaaa aaaaccaatc agaccaaatg   7080
catcatgact taaatgttgt aaatacaaag gaagtataac aataccaatt aagctagtat   7140
atagttgtgt tatataattt gatattgtat ttttttaag gctcattttt ctaacttatc   7200
ttttcaagtt caagagcaac aaatacttta tttccatgct catcaatgaa ataactattt   7260
ttatatggag ggtgtgtcat agcccttaga tagtcaattg cttcccgcat tgttactatt   7320
ttatctaaat caatttcaca catgttttta taatcatgaa ttgaattata gttgccttcg   7380
gagttaggtt tgattcgagt gaacttatta ttcaaaatat catctatgac tttagtgaac   7440
aactcaactt cttttttttg aactttagca taaacatcaa aagagttttc gaaagaatta   7500
acttcaactt cttcctgaat gattatatct ccatgatcta tctcttcatc catcacatga   7560
atagttgctc ctataggtag tttatttata atagagaaga cctgtggaaa ccaccctcta   7620
ttatatggat taagtccagg atgaatattt atacataata ctgaattaac taattttgct   7680
ggaaataatt gtttcgaatg acaagaaaaa cctaaatcat acttaccaat aagatcattg   7740
ccattttttt tcatatctat tggcttaatc tcactgttat atatttcttt ggcaaaagaa   7800
```

```
gtttgactct tgaaactaca aaaataatca acctctacat catttttact accaatgata   7860
tttttaaaat cacttagaat agttctatta tctgtaacaa caaatatttt tttcatgagg   7920
aaacctcttt gatattatta attattttat taattttatc gtcttctaac tctgcataaa   7980
ttggcaaaca taatattctt ttagatatat ctcttgagat tggcatatac tgctttggct   8040
ctatataact aagactatct aatgatggat aaaaatatct acgcgatatt atatcatttt   8100
gtattagtgc tttctgtact ctgagaagtt cctcctcagt cctaaatatt actggaaaat   8160
agctataatt cctactagaa tgctgattct gttcttgaaa ctttaccaat ccatctaacc   8220
cagcctcata tatctctgta ataactttcc ttttgctctt aatttctata atatcatcta   8280
gaacacaaag tcccatagcc gcctcaaatt cattcatttt agcattagta cctaagtaag   8340
gtattgattc tgagctttct ataccaaaat taatgaaata acgaactttt tcaacaagac   8400
tatcatcatt aatgataagc gcacctcctt caatagaatg aaaaatcttt gttgcatgaa   8460
aacttaatgt cgaaatatca ccatagttta atatactctc acccttatac ttaacatcaa   8520
aagcatgtgc tgcatcataa ataactttta agttatgttt tttagccagc atgtctattt   8580
tttcaacttc acaaccattt ccaaacacat gaactggcac aatagctgaa gtatcctctt   8640
caatagcata cttaatttta gagacgtcta tacttagagt attctcatca atatcaacaa   8700
acactggttt tacattgtta gaaaccaatg aagatgtagt agcaacaaat gaaaatggag   8760
tagtaattgc acttcctttg actcctaacg ctctatacgc gatttctaat gcaattgtac   8820
catttgatac taaaactata tttttaacac ctagatactt tgcaagtctt ttttctagct   8880
cttgcactaa cggaccatta ttagtaagcc atccattttt gtatatttta tttacatagc   8940
ttttatattt atttatatct ggtaagtatg gttttgttac atttacttta ctcattatct   9000
aaccactcct gaaaaattag aatattccat aatattgctt gccaatttct tttaccactc   9060
aaatgctctt gccaatattt ttgcaccacc tcaggactta agtaaccttg cttgtctatt   9120
ttactataat ccagtaaatt atctgcccac tctcgtaaat cttctcttaa ccatttagca   9180
agcggaatac caaaccccat cttagaccta ttgaccaaac tttctggcac atatttatat   9240
aacaaatctt tcaaaattct ttttccgtta cctcgttgta ttttatagtc aattggtaag   9300
gaataagcaa attcataaat attatgatct aaaaatggca ctcttgtctc tagagagtta   9360
gccatagctg ctctatcaac cttaaccaat atatcatcta tcatatatgt attagaatca   9420
acaaacatca tccactcttg gaaagataat tgtggaatat cataaatatt cttatctctt   9480
aatatatcat actcttttgc tcctaacaca aagctagtat catttatttg tgaacaaagt   9540
agtacataaa gctctttatt tgtttttgct ttttcgagaa ctctttttag ttttagtagt   9600
ttatctgcta ataaagcgaa cttaccaaaa tttaatatct cagctttttt tatccaagca   9660
tctggtgcat atttaagtaa cttagcaaat ttgatttttt tagcaatatt tggtgctaaa   9720
aagtatctat tataaccgcc aaagagctca tcaccagcgt cacctgatag tgcaactgtt   9780
actttcgact tagctatttt actcacaaga tacgttggta tttgtgatga atcagcaaag   9840
ggctcgtcat atattccagc aagttttggt attacatcaa gagcatctct ttctgtaaca   9900
tacatatctg tgtggtttgt acctatatgt tttgctactg ctcttgcatg ctcagcttca   9960
ttatattctt tttgattaaa acctatacta aaagtgttta tcttatcttt agacatactt  10020
tgcataagag caactacagt tgttgagtca attcctccgg ataaaaaatgc tcctagagga  10080
acatctgact gcatttgtat tgatagtgta cttttaagct taatttctaa atctaggatt  10140
```

```
gcttgatcat acgaatcttt atatttttct gaatctagta ctttttttaga atcccaatat  10200
ttatactctt tactattacc tttagcatca aattttatgt aactacctac atttagttta  10260
gatatatttt tataaataga gtatggtgtt ggtacataag catacctcat atatgttgct  10320
aaagcatctc tatctatatc aaacctccag ccacattcct ttaatggctt aagtgccttc  10380
aattctgatg caaaacccaa aataccattt tggataccaa aatataatgg cttctcgcca  10440
aatctatctc tagctagtat taagcaacta gtttttctac tgtaaactcc aaaagcaaac  10500
attcctatgc atttttctaa agttttatct ataccccaaa gttcaatagc attgaccaaa  10560
acctcagtat cactgttact tttaaattta agatttgaat attcacttaa tagctgattt  10620
tttatggata agtaattata tatttctcca ttaaacacaa tagcagtatt accgctatta  10680
gataacattg gctgatgtcc cgcattagtt atatcgtgta ttgataatct agtatgcccc  10740
agagtaactt gattgtcgca ccaataccca ctatcatccg accctctatg ctttatagaa  10800
agcaatgatt gattaattat tgagtcaaaa ccttcttctt tattaaatga gtaaaagcct  10860
actactccac acattagaca ctgccctcat gataaagttt ttcgtgtttt tccaaaatag  10920
cttctatact aaaattattt attatatatt ctctcatgcg ctttttcatg actaccgttg  10980
tttctaaaac tttcataatc ttttctatta tttctttatt accttgacta agctcaaaaa  11040
cttcaccgta tccattaagt atatctttac aatctccaac attagaagca acaataggaa  11100
cttcacatag catggcttct gcaagtatat ttggaaaacc ttcaactttt gatgtagaca  11160
aatataaatc taatactggt aagtattcac tagaatccac agattcaaat acaaaaaact  11220
tatttacatt actttttgtta tctagataac tacctatatc tattttcgaa cactctcttc  11280
cagcaattaa aaaccgtaaa ctaggattac tttttaacaa taaattagct atttgtaaga  11340
aacgagaaat atttttatca gcatgatttc ttgctatgat acctataatt ttaacattat  11400
catctaaatc attatttaaa cgaaattttt catactttaa aaagctcggt ttaaaaacat  11460
ctttatcaaa accatttgct ataaagcatt ggtttttaaa acctatattt tgatgatctt  11520
ctaatgattt ctttgaatta tttaatgtta aatctgagaa cttagaaaat tttgcattca  11580
actttatcat aaactttgta agattcttat gaccatcata attctccaat cccattctta  11640
tactatttat atatttagtc tttctataaa aaggcttgca taatatagaa attacatttg  11700
catgatacat ccaagcatga ataacatcag gctttattct tctgataatc ttaatatatt  11760
taaacaatac aaatagtaca ttaaatttat ttaaatttaa tgtataaact ttaacaccat  11820
aagcttctaa cttatttgca aatactcccc tacccataag tgatataatc gtaatatgat  11880
atattgactt atccatagat ttgcaaagtt tataaagcat tgtttcagca ccaccttggt  11940
taaggtttat tattaaatgt acaaaccttt tcaaatcaca ctcctagttg taaagctgtt  12000
ttctttaaga gaaaaaataa ataatataat ggttaattta gtaaataatc ctactgtcaa  12060
aaaaattatt tttgcttgaa aaactaaaca tactattaac aacaatagaa ataatgatcg  12120
atactctgaa aatataaaac attttctcat ttcaaagtac aagaaaataa taagaatata  12180
aaaaaacata ctaaatataa tcccataata gtataaatat ttaatataac caatatcagt  12240
attactaaca tcctcacaac caaatatcca agtcaaaagg ttatctggca caaaaagcat  12300
tttattgatt aaaacactta gacttccatg tgaaaaatcg ccagattgaa tgtacgagta  12360
aatattttca aaagcccaac tcaaattcaa atttaatttg aacaatatcc atattgataa  12420
aaagaatagc gccaatatta taataaacag taatttttct tttttaatat atatataaaa  12480
tattgttatt aacaatataa gtgaagaagt taagagtgat gttctagata tgaaaatatt  12540
```

-continued

```
agaaaacaca ataagaatta aaggtacaaa cagcataagt ttggtaaata tagatttacc  12600
tttaatatat ttgataaaat aaaatataga aaaacataat cctatagtaa ttgaaaatcc  12660
taaaccatcc cctccagcgt tactaagtcc gaatactctt aacttatatt caataacatt  12720
cgaaatctca atattccctt ttttcactaa aaaaaagaat atccaatcat ttaaaaatat  12780
ataatacctt gaaagaaata caaaaataga ttgtaagaaa gtaacaaaaa atattatttt  12840
agacatatta aaaaaataat tttcattatt atcatatgaa acaaaaataa agttacaaaa  12900
acctatcgcg atcaaaatgt taaataaaaa ctgaggaaac aatgatgctg catcaagtaa  12960
gattatttgg actattatta aataaatcat tgataaaaag aaaaagaaaa aaaggaaagc  13020
taattgtttc ttaacaatat ttccgacaaa tagtttttta agagctaaaa aacccaaaat  13080
acaagccgga agataaacta taatattcaa tatagcaaat ttaaattcta aactaaaaat  13140
aatacaaaaa gctagtaaat ataaatataa aattttaaaa gacacttttt ttatgtacac  13200
ttgattaaaa taccatttaa ttaattaaat accactcaac agcatgcttt atgcctaatt  13260
caaaatcata ttccggatta tatccgagca tattcctagc cttcgaaata tcagcattac  13320
tatgcttaat atcacccgct ctatctggac caaaatttgg ctctattttt ttacccaagg  13380
catcacaaag attatagtac aaatctataa gatactctct acctccataa gctatattaa  13440
aagactctcc ggcatactta ctatctgcta aacatgcttt aagatttgcc tcaataacat  13500
tctctatata tgtaaaatct ctcgactgtt taccatctcc atttatagtt ggcgcttcat  13560
catttaataa ctgtttgata aatttaggta taactgctgc atacgcacca ttaggatctt  13620
gtcttctacc gaaaacatta aaatatctta gaccataagt atctagacca tataactttg  13680
tgtatagtct cgcccactct tcattagctt tctttgtaaa tgcatagggt gataaaacat  13740
ttccttctct accttctttt ttaggtaaat ttggctcatc accatatact gatgaactag  13800
aagcatagac aaattttttta acgttatttt gtctagccgc ttcaagcata tttaatgcac  13860
ctttaacatt tatatcttca tacactaatg gcatctcaat acttcttggt acgcttcccc  13920
aagcagcttg atgtagaaca taatcaatac cttcacaagc tttcatgcaa gtatctaaat  13980
ctctaatatc accttttata aactcataat tagaattagt taaaaacggc tcaacattgt  14040
gatagtgacc atttgagaga tcatctaaac acctaactct ataaccctta ctaagtaaaa  14100
cttcacataa attagagcca ataaaacccg cacctccagt caccaaaaaa aacgaaccat  14160
gaggaaattt aacattatcg taagccacta caatctccaa taaatataat ctttttcaaa  14220
ctcagattta tctaaactac ctttgatgtc aaatataatc tttctagaat tatgcgcata  14280
tagcctatca aactgttgct ttgttatatc tttaaactgt tcgtgactaa cagcaataat  14340
gatcgcatct agattgacca ttttacttag atcatcaaac tcaagtccat actcatgttt  14400
agcctcttct ttatcagcta ccggatctat aatatatggc tctataccat actcgttgag  14460
ctcttttacc atatctataa ctcgagtatt cctagtgtca ggacagtctt ctttaaaagt  14520
aaagccgaaa attgctactc tagctcgctt aacaggtata tctgcagata tcagtttttt  14580
gactaaattc tcaactacaa atttacccat actatcattt atcctacgac cagataatat  14640
tacctgagaa tgatatccaa gctcagctgc cttgtacgtt aggtaatatg ggtcaacacc  14700
aatacaatgt ccaccaacaa gaccaggctt aaagtttaag aaattccatt tagttgcagc  14760
tgctgctaaa acctctagag tatcaatacc catctgatta aatattatcg ataactcatt  14820
aacaaaagct atattaacat ctctttgaga gttttctata accttagcag cttcagccac  14880
```

-continued

```
ttttatacta ctagctctat aaactcctgc gtctactact agctcataaa cttttgctat  14940
agtatctaaa gactcttcat ccataccaga tactactttg ataattgttt ctaacctatg  15000
aaccttatca ccaggattta tcctctcagg agagtaacca actttgaaat cttcaccaga  15060
cctcaagcca gactcttttt caagtattgg tacgcaaaca tcttctgtaa caccaggata  15120
aacagttgat tcaaacacaa cataagcgcc tttgacaaga ttcctaccaa ccgtctcact  15180
tgccttaata atcggcgtca aatcaggagt tttatctgct ttaactggtg taggaactgc  15240
aacaatatga aatttacact ctttaagact tgtttcatca caactaaatt tcattgtcgt  15300
atttctgaca gcctcatctc ctacttcttt tgttggatca aaaccatcct tataatgttg  15360
aacttttgtt tcacaaatat caaatcctaa cacatctatt ttttttgcaa atgcaatagc  15420
tattggtaaa ccaacataac ccaagccaac caatgaaacc ttttctcttt tagcgactat  15480
atcctcatat aaactcataa tttaaaccct tattattaat tttgctgtaa gtatgcattg  15540
acaacaatac ttctatcaaa atctttttct atcttagctc tagctttata gctcatagct  15600
attttatcag tatacgacat atttataaac tgctctaatg agttacgtaa agaactcaca  15660
tcattagggt tacatgataa gccagagaga ccatcatcaa aaatttctct acacccagga  15720
atatctgacg caattacagg tctacctatc gcagctgctt ctaacagcac atttgacatt  15780
ccttcatggt aagatggcaa aacaactgca tgtgcactag ctattttttc tttagtatta  15840
tcagtaaaac cataaaattt tactgatttt atcgtattaa cctttcccat aaaattagat  15900
ttattttcat cacaaaaacc ataaatgtca agactaatat ttttatattt tttctcaagt  15960
atagcaaagg cttctaacaa ttcataaatc cccttttctt tcattattcg gccaagaaaa  16020
acgaatttta atattccttg gtctttagga tagtcaacat atttattttc atctaagttt  16080
accccagaac ctggtaataa tattgatttt tctccactga ttattttctt agctataaat  16140
aactttttat tttgctcatt ctgaaagaat acttttgtgg tgcttttaaa tgataactta  16200
tataaagata ttataaactt ctgaacaata ccatgattag caaaaacact tcctaagcct  16260
gttacatttg gataaaactt cttcctaaaa aacaaattca ctaacccaac atacaaattt  16320
ggtttaattg tatagctaaa aatgtaatca ggtttttctt tttttattat tttgaaatag  16380
ttaaataaaa gaagcaaatc cttaaaagga tttttgcctc gtctatctat atcaacattt  16440
atatacttaa caccaagact tttacaaaaa acctctgctt tcttagaata tggtgttact  16500
agtactatct catactcttt agcagcaaaa gactcgatta cttctcttct gaaacgatat  16560
attacaatat caaaatcatt agctatgaat aataacttac ttctcataag tcaaattccc  16620
aaaaacttta ttaataaaat ctactttttt agcaagcaat cttataattg gattaaaaat  16680
ttttgtcaga taagttctct tacctaaaac atcttttcta tagtttttta taaactgtga  16740
agtgcaaaaa tattcattat cttgaagtag aaaaactcca tgtttagttt gcaaaattat  16800
ttctgcaatc tctttagata aattatctat agatataaca cttctttggt tattaatatt  16860
aggaaaaata aaagtatact ttgcaagttt aaccaacttt ggatagttgc cttttgagcc  16920
ttctccatat accattggtg gtctgattat agcaatatta aagtcatcac tagccaggct  16980
atttagctta atttcagttt gaagcttact atctccataa aaatcatctg gtttaggttc  17040
ggtatattta gttataactt tttgttgacc tattggcgca ctatcaccat aaactataat  17100
actacttaaa aacacaaact gtcgaacacc ttgatcttta gcttgttttg ccagatcata  17160
agttaattgc gtatttattt tatagtattt ttcttttagt ttaggatcct ttgaagtatg  17220
ggcaattcca gcgacatgca atacagcatc ataaccactt aagtctatat ttgcccacga  17280
```

-continued aacatcgcgc aaagatattt tatcgatact aaaatctgag ttatatttag ccgcaaatga 17340
gttaccaata tagctactca aacctgtaac taagattctt tttttcatac tactttaaat 17400
cctctttgtt acctaaagct ccagtaccac cctcaacgac gcccttttttg gcaaaaacag 17460 aaaatactgt caaaaaaata cattttaaat caaaccatgt acttttattt tttacataat 17520
caccatcaag tttagcttta tcaggtattg gtaattcatc cctaccatta atctgtgccc 17580
agccagtcag tcccacaggc acagcatttg ccccatactt atctctttgt gctattaagt 17640
catcttgatt ccataatgct ggtcttggac ccacgatgct catttcacct tttagaatat 17700
ttataatttg tggcaactca tctaaagatg atttccttaa aaatcctcca accttagtta 17760
tacatttcga tggatcctgt aacatgtgcg ttggcatatc ttttggagta tcaacataca 17820
tagttctaaa cttatatatg taaaaaaatt gcttatcttt accatagcgc ttttgtttaa 17880
aaaatatagg tccttttgaa tctttcttta tcataaaaat aataattaag aaaataggac 17940
ttaataacaa caaccccata aaagaaagta aaatatcaag caatctttta aaaacctcat 18000
aaaacataaa accactaccc attcaatcta tgttcaaatt ccggaacaat tttctttaat 18060
atcacaagct gatcaacatc atccttgatc aacgattcaa tatcttggtt tagagtatta 18120
atatcgtaaa aagtccttct accaataaaa atatctttat agtcggtact aacatcatct 18180
tcctctatca aaagctcttc gtaaagtttc tctcctggac gcaaaccaac tattttaata 18240
tcaatatcac ctctaccaga aagtctaata aattgtttag caagatcaat aatcttgaca 18300
ggttgcccca tatctaagac aaagacctct gaatttttttg caatagcacc agcttgtagg 18360
accagttcac aagcttctgg tatcaacata aaataacgtg taatttcagg atgagtaact 18420
gtaacaggac cacctttttct tatttgctct tcaaattttg gaatcacact gccactacta 18480
ccaagcacat taccaaaacg cactgcagca agcttggtat ttttgggatc aacattctgt 18540
aaatacagct cacaaactct cttggtagcc cccataacat tcgttggtcg cactgcttta 18600
tcagtggaaa tcaatataaa tgactcaaca ccagcttcta tagccagatc tatagcattc 18660
ttagtaccta agatattatt tctaattgct ctagagatat tctcctcaac taagggaaca 18720
tgcttgtagg cagcagcatg aaatactata tttggagtat acttttgaaa aacctcagcc 18780
aatgcttttc tatcacaaac agaacatagc acactattga tattaaaatg actacactcc 18840
tcagtaattt tatataagtt aaactcacta tgatcaacca atatcaactc ttttgcctga 18900
tacttgatac attgatgtac tatttcagaa cctatactac ctccagctcc tgtgactagc 18960
accaccttat ttttgataaa attagagata gattctttat ctaaactctt agtatcacgc 19020
gctaatagat catagagtga aacaggcttc aactgtgaca taaaattctc atcttgaaga 19080
atttcctcaa gaggcggcat aattctaatc tgattaaaat ccttttcaaa ttctttatat 19140
atatttttga ctacttggtt tgcatttctt ggcaatgcaa taaccaaaag gtcaaatcta 19200
ctagatagca atagttttgt taattcagct ttagatagaa ccttttttact atcaatactt 19260 ctttttttgta aagtttcatt gtcatcaaca aaacatttga tgcgataacc agcagaagca 19320
agttcttgag caatctttgt tcctgcagca cctgcaccat aaataaccgc agttttactt 19380
ttatccactg atcctctgtt catcaaatac caataaaagt agacacttaa actgatcaaa 19440
aaaacataaa ataaaaactc agagaatatc aacgaaaaag tgactttgcc ataaaaaaat 19500
aatgccacta tgaaaaatac tggcaaatta ataaaagcct tacgtaaaaa agttttttga 19560
gtcgacttac gccaactagc catataatct ctaagtagta aaaaagatga caagcatctc 19620

-continued

```
agcaaaacta atgcaagtaa aaaatgtaaa ttaacatctt gcttgaaaat atagaaagtc  19680
caattaacag taataatagt taaaactatt attaccacga aattaagcgt tctattatcg  19740
tagaaagaca tttgttaatt tttagaaaat atcctattaa agtctattat atcaaaaaaa  19800
ttttctttgt gcacaaaaat gcaaattagg ttctgtgcac aaaaataaat attcatcgta  19860
accaaataaa agtacaagct aatttaatca ttcctatata tgctaaaatg gttttatcaa  19920
atctagagaa tactcttcta aaatgcttaa ttttagaaaa gaaattctct atcaaatgtc  19980
tttctttata tacatgacta tcaaaaggta tatggtttag agtatttgat ttacaaggga  20040
taacagcttc agaggatata ccttgaatat gctgcctgat ttcattagaa tgatatgctc  20100
tatcagcgat aacttttgta ttatatacat tttttagtaa atctatagct actttactat  20160
catgagtttt atcctctgac aacaatattt ctattggatt acctaaagca tcagtcatag  20220
catggatttt agtggttatc ctaccaactg atctaccaat tgcttggtta tcatctttat  20280
catatcccgt agcacaagca tgtgctcttg ctattgttga atcaagcatg acttcttgta  20340
aatcagggtt ttgtactgat ttaaataatc tagaaaatat atctttatca caccaatctt  20400
taaaacgctt atgtattgat ctatatttac cataataaaa tggtaacatt ctccattgac  20460
agcctgtacg taacacataa aatacagctt caataaacaa tcttaatttg gcttcatcat  20520
tggtatgtat acctttttgt gattttaaga atgataaaat aattgaccag aatacttctt  20580
ttatatgata attcatttgc taaaccattg atatttattg cttttcaaat cttaaataac  20640
agcggtttag ctattttcaa tataatttaa gtttttttgtg cacagaacct attatttttt  20700
gtttgctatc atcatttata aaagaagctc ttgcagcatt tagattcata ataaccatat  20760
ttcaaaggaa agattatttt taagataagc attataatac tcatctgtca ttgttatgtt  20820
tctaagcatc aatcgatcat ccgtataata ctgatattat cagctaacat tctttgataa  20880
gagtgatttt caaaactatc tacaatacct aaagctacgt tactacttac atttgactct  20940
atatgaatat ttctatcaat tagtaaagca ataacttcac gtaaaagatc taaatcttta  21000
gttttatata gattacaacc atgacctatt ctagatgcac cacttaaaat actagctttg  21060
atattactaa tactagaaaa ctcaccacta tgaacagtaa atttaacatt attatttcta  21120
agaaactcta gtgttctagg taatacttta gatacatcac cagcaatatc cattccagca  21180
acatcataac caacaatttg agaatatttc gtacataact ccgctaattc aaggttaata  21240
tcatcactaa ggctatacat accacaaaca agtatacctg cttctatatc atatttttgt  21300
ttggctctcg caaaccctgc tgatatactt tcgattatct cagcatatga taaatcttga  21360
ttacggtgga aataagggca aaatctggct tcgacataaa taacattatc taaagcatga  21420
tcttcaacaa actcaaatgc aacccgttca agaccttctt tagtttgcat aacagcgcca  21480
gcaatattaa aagcagcaaa acatttgtca aagtcttttg atgaaaattc accatagaac  21540
cattctaaaa gttcagctga gtatgcttcg gaagtttaat attgtactta gcagcaagtt  21600
ctataatagt atcaacacgc aaaccaccat caagatgatc atgcaaaaca acttttggta  21660
tcgaaaaaat cttatctctc at                                          21682
```

<210> SEQ ID NO 9
<211> LENGTH: 2142
<212> TYPE: DNA
<213> ORGANISM: Campylobacter jejuni

<400> SEQUENCE: 9

```
atgttgaaaa aagagtattt aaaaaaccct tatttagttt tgtttgcgat gattatatta     60
```

-continued

```
gcttatgttt ttagtgtatt ttgcaggttt tattgggttt ggtgggcaag tgagtttaat    120

gagtattttt tcaataatca gttaatgatc atttcaaatg atggctatgc ttttgctgag    180

ggcgcaagag atatgatagc aggttttcat cagcctaatg atttgagtta ttatggatct    240

tctttatccg cgcttactta ttggctttat aaaatcacac ctttttcttt tgaaagtatc    300

attttatata tgagtacttt tttatcttct ttggtggtga ttcctactat tttgctagct    360

aacgaataca aacgtccttt aatgggcttt gtagctgctc ttttagcaag tatagcaaac    420

agttattata atcgcactat gagtgggtat tatgatacgg atatgctggt aattgttttg    480

cctatgttta ttttattttt tatggtaaga atgattttaa aaaaagactt tttttcattg    540

attgccttgc cgttatttat aggaatttat ctttggtggt atccttcaag ttatacttta    600

aatgtagctt taattggact ttttttaatt tatacactta tttttcatag aaaagaaaag    660

atttttata tagctgtgat tttgtcttct cttactcttt caaatatagc atggttttat    720

caaagtgcca ttatagtaat actttttgct ttattcgcct tagagcaaaa acgcttaaat    780

tttatgatta taggaatttt aggtagtgca actttgatat ttttgatttt aagtggtggg    840

gttgatccta tactttatca gcttaaattt tatattttta gaagtgatga aagtgcgaat    900

ttaacgcagg gctttatgta ttttaatgtc aatcaaacca tacaagaagt tgaaaatgta    960

gatcttagcg aatttatgcg aagaattagt ggtagtgaaa ttgttttttt gttttctttg   1020

tttggttttg tatggctttt gagaaaacat aaaagtatga ttatggcttt acctatattg   1080

gtgcttgggt ttttagcctt aaaagggggg cttagattta ccatttattc tgtacctgta   1140

atggccttag gatttggttt tttattgagc gagtttaagg ctataatggt taaaaaatat   1200

agccaattaa cttcaaatgt ttgtattgtt tttgcaacta ttttgacttt agctccagta   1260

tttatccata tttacaacta taaagcgcca acagtttttt ctcaaaatga agcatcatta   1320

ttaaatcaat taaaaaatat agccaataga gaagattatg tggtaacttg gtgggattat   1380

ggttatcctg tgcgttatta tagcgatgtg aaaactttag tagatggtgg aaagcattta   1440

ggtaaggata attttttccc ttcttttgct ttaagcaaag atgaacaagc tgcagctaat   1500

atggcaagac ttagtgtaga atatacagaa aaaagctttt atgctccgca aaatgatatt   1560

ttaaaaacag acattttgca agccatgatg aaagattata atcaaagcaa tgtggatttg   1620

tttctagctt cattatcaaa acctgatttt aaaatcgata cgccaaaaac tcgtgatatt   1680

tatctttata tgcccgctag aatgtctttg atttttttcta cggtggctag tttttctttt   1740

attaatttag atacaggagt tttggataaa cctttacct ttagcacagc ttatccactt   1800

gatgttaaaa atggagaaat ttatcttagc aacggagtgg ttttaagcga tgattttaga   1860

agttttaaaa taggtgataa tgtggtttct gtaaatagta tcgtagagat taattctatt   1920

aaacaaggtg aatacaaaat cactccaatt gatgataagg ctcagtttta tattttttat   1980

ttaaaggata gtgctattcc ttacgcacaa tttattttaa tggataaaac catgtttaat   2040

agtgcttatg tgcaaatgtt ttttttagga aattatgata agaatttatt tgacttggtg   2100

attaattcta gagatgctaa ggtttttaaa cttaaaattt aa                      2142
```

<210> SEQ ID NO 10
<211> LENGTH: 636
<212> TYPE: DNA
<213> ORGANISM: Francisella tularensis

<400> SEQUENCE: 10

-continued atgattatga gtgagatgat aacaagacaa caggtaacaa gtggcgagac cattcatgtg 60
agaactgatc ctactgcatg tataggatct catcctaatt gtagattatt tattgattct 120
ttaactatag ctggggagaa acttgataaa aatatcgttg ctatagatgg tggagaggat 180
gtcacgaaag ctgattcggc tacagctgct gctagtgtaa tacgtttatc tataacgcca 240
ggctctataa atccaacaat aagtattact cttggtgttc taattaaatc aaatgttaga 300
actaaaattg aagagaaagt ttcgagtata ttacaagcaa gtgctacaga tatgaaaatt 360
aagttaggta attctaataa aaaacaagag tataaaactg atgaagcatg gggtattatg 420
atagatctat ctaatttaga gttatatcca ataagtgcta aggcttttag tattagtata 480
gagccaacag aacttatggg tgtttcaaaa gatggaatga gatatcatat tatatctata 540
gatggtctta caacatctca aggaagtttg ccagtatgtt gcgcagctag cacagataaa 600
ggagttgcta aaataggata tattgcagct gcatag 636

<210> SEQ ID NO 11
<211> LENGTH: 1929
<212> TYPE: DNA
<213> ORGANISM: Francisella tularensis

<400> SEQUENCE: 11
atgggaaaaa taataggtat agatttaggt actactaact cttgtcttgc tattatggat 60
ggcaagactg ctaaagttat tgagaatgct gaaggacata gaacaacacc ttcagttgtg 120
gcatatactg atagcggtga aatattagta ggtcaagctg ctaaaagaca agctgtaact 180
aaccctgata atacattctt tgctatcaag agacttatag gtcgtaagta cgatgataaa 240
gctgtacaag aagatattaa aaagaaagta ccttatgcgg taattaaagc tgataatggt 300
gatgcttggg ttgctactaa agaaggcaaa aaaatggctc caccacaagt ttctgcagaa 360
gttctaagaa aaatgaaaaa aacagcagaa gactatctag gtgaaccagt tacagaagct 420
gtaattacag tgccagcata ctttaacgat agtcaaagac aagctacaaa agatgctggt 480
aaaatagcag gtcttgaagt taaaagaatt atcaacgagc ctacagcggc agcgctggca 540
tatggtgtag actctaagaa aggtgagcaa actgtagcgg tgtatgacct aggtggtggt 600
acattcgata tctcaattat tgagattgct gatgttgatg gcgataacca aatcgaagta 660
ttatcaacca atggtgatac tttcttaggt ggtgaagact tcgacttggc tttaatgaac 720
tatctaattg acgagttcaa aaaagagcaa ggtatagatc ttcacaatga taagcttgct 780
ttacaaagag ttagagaggc tgctgagaaa gctaaagtag aattatcttc agcacaacaa 840
actgatgtta acctacctta catcacagca gatgctactg gacctaagca cttaaatatc 900
aaagtaacta gagctaagtt tgagtcttta gtttctgatc ttgtaatgag atcacttgag 960
ccttgtaaga aagctcttga agatgctggt ttaagtaagt ctgatattac agaagtatta 1020
ctagtgggtg gacaaactcg tatgcctcta gtacaagaga aagtaaaaga gtttttttggt 1080 aaagagccac gtaaagatgt gaaccctgat gaagctgttg cagttggtgc ggctattcaa 1140
ggtggtgtat tagcaggtga tgttaaagat attcttttat tggatgtaac accgctttct 1200
ctaggtattg agactatggg aggtgttatg actaagctta tcgagagaaa tactacgatt 1260
cctactaaga agtcgcaagt attctcaaca gctgaagata accagcctgc ggtaactatt 1320
catgtacttc aaggtgagcg tgaaatggct tctgcaaaca aatctttagg tagatttgat 1380
ctggcagata ttccaccagc gccacgtggt atgccacaaa ttgaggttac ttttgatata 1440
gatgctaacg gtatattaaa tgtgtctgct aaagataaag ctactggtaa agagcaaaat 1500

```
attgtgatta agtcttcaag tggtttatct gaagaggata tcgaaaaaat ggtacaagac   1560

gctgaagcta atgcagaagc agataaaaag ttccatgatt tagttactgc tagaaatact   1620

gctgataact taattcatag ctcaagaaaa gcaattcaag aactgggtga caaagtaaca   1680

gcagcagaaa aagaaaaaat cgaagaagct tgtaaagagc ttgaagcagc aactaaaggt   1740

gatgataagc aagcgattga atctaaaact aaggctctag aagaagcatt tgcgccaata   1800

gctcaaaaag cttatgctga gcaagctcaa gctgctgttg cccaaggtgg tgctaaagct   1860

gaagaaccta agaaagaaga agatgttgtt gatgctgact ttgaggatgt tgaagacgac   1920

aaaaaataa                                                           1929
```

<210> SEQ ID NO 12
<211> LENGTH: 71
<212> TYPE: DNA
<213> ORGANISM: artificial sequence
<220> FEATURE:
<223> OTHER INFORMATION: primer

<400> SEQUENCE: 12

```
gtgaatttac tgacagtgag tactgatctc atcagtattt ttttattcac tgtgtaggct     60

ggagctgctt c                                                          71
```

<210> SEQ ID NO 13
<211> LENGTH: 450
<212> TYPE: DNA
<213> ORGANISM: Francisella tularensis

<400> SEQUENCE: 13

```
atgaaaaaaa taattaagct tagtctttta tctttatcaa tcgcaggttt agcgagctgt     60

tctactctag ggttaggtgg ctctgatgat gcaaaagctt cagctaaaga tactgctgct    120

gctcagacag ctactactga gcaagctgct gctgtatcta agccaactgc aaaagtaagt    180

ttaaataaac ttggtcagga taaaataaaa gcaactgtat atacagcata caataataac    240

ccacaaggaa gtgtaagatt acaatggcag gctccagaag gttctaagtg ccatgataca    300

agcttcccaa ttactaagta tgctgagaag aacgataaaa cttgggcaac tgtaacagtt    360

aagcaaggta ataacttctg tagcggtaag tggacagcta atgtagttta tgacaaagaa    420

gtaatcgctt ctgattcaat aaatatttaa                                    450
```

<210> SEQ ID NO 14
<211> LENGTH: 1545
<212> TYPE: DNA
<213> ORGANISM: Francisella tularensis

<400> SEQUENCE: 14

```
atggtaagta gggaggattt tattatgaca ataaataaat taagtctcac tgatgaactt     60

ttaaataatt ttgggggatc tacagaagtt gatagtgtac tcaaaaatat agattttgat    120

gtttcagatg atgcttctaa agttttatct ttatctactg actacaatgc tagaaacctt    180

atggcgctat ctttggtatt agcaaataat gataatataa ataattataa tcaaaaatat    240

atccagaaag ttattacagt tattgataag cttattgatt tacaagttaa ttctattata    300

tctaatgatg agtttagagc acttgagcaa gaatggctaa aggtgcaaga ggtttgtcaa    360

gaagactatg ataatgttga agtaagtata ttagatgtaa aaaaagaaga gctacaatat    420

gatttcgaga gaaatttata tgatatatct agtagtgact tttcaaaaa agtttacgtt    480
```

-continued

```
tcagaatttg atcaatatgg tggcgaacct tatggcgcaa tattaggatt gtataatttt    540
gaaaatacca caaatgatat aatttggttg actggaatgg gtatggtggc aaagaattct    600
catgcaccat ttattgcatc aattgataag tcattctttg gtgttaagga tttatcagaa    660
atcactcata taaaaagttt tgaagctttg cttgagcatc ctagatataa agagtggaat    720
gattttagaa accttgatgt tgctgcatat ataggtttga ccgtaggtga ttttatgttg    780
cggcaaccat ataatcctga gaataatcca gttcagtata aacttatgga aggctttaat    840
gagtttgttg attatgataa gaatgaaagt tatctatggg gacctgcttc aattcatcta    900
gttaagaata tgatgagatc ttatgataaa actagatggt tccaatatat aagaggagtt    960
gagagtggtg gttatgtaaa gaacttggta gcttgcgtat atgataataa aggcattcta   1020
gaaactaagt cacctttaaa tgtattattc gctgattata tggagttatc acttgcaaat   1080
attggtttaa taccatttgt aagtgaaaaa ggtactagta acgcttgttt ctttagtgta   1140
aattctgcta aaaaagtcga agaatttgta gatggatttg actcagcaaa ctcaagatta   1200
attgctaacc tttcttacac tatgtgtata tcgagaatat ctcattatat taaatgtgta   1260
attagagata agattggtag tattgtggat gtcgagtcga ttcaaaaaat tctttctgat   1320
tggatatcag aatttgtcac cacagtctat caaccaaccc ctttagaaat ggcgagatat   1380
cctttcagaa acgtttctat cgaggttgaa accataccgg gtaagcctgg ctggtattca   1440
tgcaaaataa atgtaattcc ccacattcaa tttgaaggaa tgaatactac aatgactata   1500
gatactaggc ttgaaccaga attattcggt acaaataata actaa                   1545
```

```
<210> SEQ ID NO 15
<211> LENGTH: 288
<212> TYPE: DNA
<213> ORGANISM: Francisella tularensis

<400> SEQUENCE: 15

atgaacattc gtccattaca agatagagta ttagttcgtc gtgcagaaga agaaaaaaaa     60
tctgctggtg gaattatctt aactggtagt gctcaagaga aacctagcca aggtgaggtt    120
gttgctgttg gtaatggtaa aaaattggat aatggcacta cgctacctat ggatgtaaaa    180
gttggtgata aagtgctgtt tggtaaatac tctggtagtg aagtaaaagt tggtgatgaa    240
actcttctaa tgatgagaga agaagatatc atgggtatta ttgcataa                288
```

```
<210> SEQ ID NO 16
<211> LENGTH: 1635
<212> TYPE: DNA
<213> ORGANISM: Francisella tularensis

<400> SEQUENCE: 16

atggctgcaa aacaagtttt attttcagat gaagctcgtg caaaaatgct agatggtgtt     60
aacacactag caaatgctgt aaaagttact ttaggtccaa aaggtcgtaa tgttgtttta    120
gataaatcat ttggcacgcc tactatcact aaagatggtg tatctgttgc taaagaaatt    180
gaactagaag ataagtttga gaatatgggt gctcagatag ttaaagaagt agcttcaaag    240
acagcggatg ttgctggtga tggtactact acagcgactg tacttgctca ggcattattg    300
acagagggtc taaaagctgt cgctgcaggt atgaatccta tggatctaaa aagaggtatc    360
gacaaagcaa ctgctaggtt agttgaagaa ttaaaagcac tttctaaacc atgttcagat    420
ccaaaatcaa ttgagcaagt tggtactatc tctgctaact ctgatgctac tgtaggtaag    480
cttatcgctg acgcaatggc aaaagttggt aaagaaggtg tgattacagt tgaagaaggc    540
```

```
aaaggctttg aagatgagct tgatgtagtt gaaggtatgc agtttgatag aggttatcta    600
tctccgtatt ttgcaacaaa tcaagagaat atgactactg atttagagaa tccatatatt    660
ctaatagttg ataagaaaat ctctaatatc cgcgatttat taccgatatt agaaggtgtt    720
tctaaatctg gtagagcgtt actaataata gctgaagatg tagaaagtga agctctagct    780
actttagttg taaataatat gcgtggtgta gttaaagtat gtgctgtcaa agctcctggc    840
tttggtgata gaagaaaagc tatgctagaa gatatcgcta ctctaactgg agctacgttt    900
gtatcagaag acctaagcat gaagttagaa gaaactaaca tggagcattt aggtacggct    960
agtagagtac aagtaacaaa agataataca acaattattg atggtgctgg tgaaaaagaa   1020
gctatcgcta aacgaataaa tgtaatcaaa gctaatattg ctgaagctaa ctctgattat   1080
gatcgtgaga agctgcaaga aagattggct aaactttctg gtggtgtcgc ggtgataaaa   1140
gttggtgctg ttacagaagc tgagatgaaa gagaagaaag atcgtgtcga tgatgcttta   1200
catgctactc gtgcggctgt agaagaaggt attgttgctg gtggtggcgt tgctttaatt   1260
agagcacaaa aagcattaga tggcttaaca ggtgaaaatg acgatcaaaa ctatggtata   1320
gcgctactta gaaaagcaat agaagctcct ctaagacaga tagtatcaaa tgctggcggt   1380
gagtcttctg tagttgttaa ccaagttaaa gctaatcaag gtaactatgg ttataatgct   1440
gcaaatgata cttatggtga tatggttgag atgggtattt tagatcctac taaagttact   1500
cgttcagctc tacaacatgc tgcttcaatt gctggactta tgatcactac agaggcgatg   1560
atcggtgaga tcaaagaagc tgctcctgct atgcctatgg gcggtggcat gggcggtatg   1620
cctggcatga tgtaa                                                    1635
```

<210> SEQ ID NO 17
<211> LENGTH: 1104
<212> TYPE: DNA
<213> ORGANISM: eschericia coli

<400> SEQUENCE: 17

```
gtgaatttac tgacagtgag tactgatctc atcagtattt ttttattcac gacactgttt     60
ctgtttttttg cccgtaaggt ggcaaaaaaa gtcggtttag tggataaacc aaacttccgc    120
aaacgtcacc agggattgat acctctcgtt ggggggattt cggtttacgc agggatttgc    180
ttcacgttcg gaattgtcga ttactatatt ccgcatgcat ctctctatct cgcttgtgcc    240
ggtgtgcttg ttttcattgg cgcgctggat gaccgttttg atatcagcgt aaaaatccgt    300
gccaccatac aggccgctgt tggcattgtt atgatggtgt tcggcaagct ttatctcagt    360
agcctgggtt atatctttgg ctcctgggag atggtgctcg gaccgtttgg ttacttcctg    420
acgctatttg ccgtctgggc ggccattaat gcgttcaaca tggttgatgg cattgatggc    480
ttgctgggcg ggttgtcctg cgtctcgttt gcagcaatcg gtatgatttt gtggttcgac    540
gggcaaacca gcctcgcaat ctggtgcttt gcgatgatcg ccgccatcct gccatacatc    600
atgcttaacc ttggtatcct gggtcgccgc tacaaagtct ttatgggtga tgcgggcagt    660
acgctgattg gttttaccgt tatctggatc ctgctcgaaa cgacccaggg caaaacccat    720
cccatcagcc cggttaccgc tttgtggata atcgccattc cgctaatgga tatggtggcg    780
attatgtacc gtcgcctgcg taaaggcatg agcccattct ctcctgaccg tcagcatatt    840
caccatttga tcatgcgtgc cgggtttact tcccgtcagg cgtttgtgct gattaccctt    900
gccgcagcac tgctcgcttc cattggcgtg ctggcagaat attctcattt tgtcccggag    960
```

```
tgggtcatgc tggtgctctt tttgctagca ttcttcctct atggatattg cattaagcgt   1020

gcctggaaag ttgctcgctt tattaagcgc gtaaaacgca gactgcgtag aaatcgtggt   1080

ggcagcccca atttaaccaa ataa                                          1104


<210> SEQ ID NO 18
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any amino acid
      except proline

<400> SEQUENCE: 18

Asp Xaa Asn Xaa Ser
1               5


<210> SEQ ID NO 19
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any aminoacid
      except proline

<400> SEQUENCE: 19

Asp Xaa Asn Xaa Thr
1               5


<210> SEQ ID NO 20
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any amino acid
      except proline

<400> SEQUENCE: 20

Glu Xaa Asn Xaa Ser
1               5


<210> SEQ ID NO 21
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any aminoacid
      except proline

<400> SEQUENCE: 21

Glu Xaa Asn Xaa Thr
1               5
```

<210> SEQ ID NO 22
<211> LENGTH: 713
<212> TYPE: PRT
<213> ORGANISM: Campylobacter jejuni

<400> SEQUENCE: 22

```
Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
        115                 120                 125

Gly Phe Val Ala Ala Leu Leu Ala Ser Ile Ala Asn Ser Tyr Tyr Asn
    130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
        195                 200                 205

Leu Ile Tyr Thr Leu Ile Phe His Arg Lys Glu Lys Ile Phe Tyr Ile
    210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
    290                 295                 300

Phe Met Tyr Phe Asn Val Asn Gln Thr Ile Gln Glu Val Glu Asn Val
305                 310                 315                 320

Asp Leu Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
        355                 360                 365

Gly Gly Leu Arg Phe Thr Ile Tyr Ser Val Pro Val Met Ala Leu Gly
    370                 375                 380
```

```
Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
        435                 440                 445

Asn Arg Glu Asp Tyr Val Val Thr Trp Trp Asp Tyr Gly Tyr Pro Val
    450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
        515                 520                 525

Met Met Lys Asp Tyr Asn Gln Ser Asn Val Asp Leu Phe Leu Ala Ser
    530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
        595                 600                 605

Leu Ser Asn Gly Val Val Leu Ser Asp Asp Phe Arg Ser Phe Lys Ile
    610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
        675                 680                 685

Leu Gly Asn Tyr Asp Lys Asn Leu Phe Asp Leu Val Ile Asn Ser Arg
    690                 695                 700

Asp Ala Lys Val Phe Lys Leu Lys Ile
705                 710
```

<210> SEQ ID NO 23
<211> LENGTH: 2133
<212> TYPE: DNA
<213> ORGANISM: Campylobacter sputorum

<400> SEQUENCE: 23

```
atgtcaaatt ttaatttcgc taaatttcta aataaattac ctagactttc taaacatact      60

attttaatga ttgttttagc tgtttgtttt gggatatttt gcagatttta ctgggtagtt     120

tgggctagtg cttatccgca ttttatatgg aatgatcagc ttatgataag cacaaatgac     180

ggatatgcat ttgctgaggg cacaagagat atgatagctg gttttcatca accaaacgat     240
```

```
ctttcttact atggctcatc tctttcgacg cttagcatgt ggttatataa cattttgcca    300
ttttcattag aaactatact tttgtatatg agtacatttt tatctccact cttagctgtg    360
cctttgatac ttataggtaa agaactaaac gcttcaaaag cgggttttat agctgcactt    420
ctagctatta ttgcaaatag ttattataat agaacaatga gtggatatta cgatacggat    480
atgctaaata tcactcttcc tatgatggtt ttttggagca taacaagact tgttcaaaga    540
aaagagagag taaatttaat atttattccg gtttttatgg cgatatatgg atggtggtat    600
ccatcttctt actcactatt acttgccatg attggaatgt ttttttata taccattgtt    660
tttgaaagat acgaaaaact aaactatgaa gctatggttt ttatgatttt agcaatcaca    720
agcttttcta tacaaattaa atttattata gttattgttt tgtatgcttt aatctatttt    780
taccaaagat tttttgataa aaaagtaata tttgcattaa ttatggcttc gttaatatgc    840
tttatatggc ttggcgggct aaaccctata ctttttaaca ttaaatttta tatatttaga    900
gacattgcag atagcggtga tgctgttttt aaatttttca atgtaaatca aacaataaga    960
gaaagttctg cgatagattt taacacagtt gtaactagga ttagcgggca tttaatagta   1020
tttttggtat ctattatagg atatatttta tttataaaaa acaataaaat tttactacta   1080
actttaccga ttctgttttt gggtcttatg tcatttaaaa gtggtttaag atttacaata   1140
tactcagttc cagtaatggc tcttggtttt ggctattttg ttatgtattg ttttgcaaaa   1200
atagatataa aagatcgttt tttaggttat gtgtttttat ttgttgtaac atttagtgca   1260
ttatatccat ctttaaaaca tatttatgat tataaagtat ttcctgtttt tacacatagc   1320
gaagttgaaa gtttggataa tttaaaaaat attgcaaaaa gagaagatta tgtgctttct   1380
tggtgggatt atggttatcc gatcagatat tattcagatg taaaaactct catagatgga   1440
ggaaaacatc ttggaagtga taacttcgcc gttagctttg cacttggaag cgatcaaaat   1500
agctctgcaa atatggcaag attagaagtt gaatatacag aaaaaaatta tgaagaaaaa   1560
tttggattaa atttaaaaaa gatgatgaaa gattataatg ctacaaatgt taatgagttt   1620
ttattatcat taaaagatga aaatttaact ctgccaaagc aaacaagaga tatttattac   1680
tatttaccag atagaatgat atacatatat ccgatagtgc tagatttttc tagacttgat   1740
ttgacaacag ggcaagaatt tgcccagccg ttttttatgg ttagtgagag attttcagct   1800
acaaatgata atcaaataat gttaaataac aatgtcatat taagtaatga tggcactaaa   1860
ttatcgataa atggcaactc ttatagtgta aatacatatg ttgaaacaag ttatgatcaa   1920
aacgaaaaat taaatgtaaa ttattttaac atagatccaa atagcaattt ttatgtgatt   1980
tttatgaaag attatttgag aattttggtt ttagataaaa ctttgtatga tagtgcgtat   2040
attcaacttt ttgtattaga aaattatgat aaaaatttat ttgaaccagt gattttaaac   2100
ggatcaacta aaatttataa actcaaaaaa tga                                2133
```

<210> SEQ ID NO 24
<211> LENGTH: 710
<212> TYPE: PRT
<213> ORGANISM: Campylobacter sputorum

<400> SEQUENCE: 24

```
Met Ser Asn Phe Asn Phe Ala Lys Phe Leu Asn Lys Leu Pro Arg Leu
1               5                   10                  15

Ser Lys His Thr Ile Leu Met Ile Val Leu Ala Val Cys Phe Gly Ile
            20                  25                  30

Phe Cys Arg Phe Tyr Trp Val Val Trp Ala Ser Ala Tyr Pro His Phe
```

```
        35                  40                  45

Ile Trp Asn Asp Gln Leu Met Ile Ser Thr Asn Asp Gly Tyr Ala Phe
    50                  55                  60

Ala Glu Gly Thr Arg Asp Met Ile Ala Gly Phe His Gln Pro Asn Asp
65                  70                  75                  80

Leu Ser Tyr Tyr Gly Ser Ser Leu Ser Thr Leu Ser Met Trp Leu Tyr
                85                  90                  95

Asn Ile Leu Pro Phe Ser Leu Glu Thr Ile Leu Leu Tyr Met Ser Thr
            100                 105                 110

Phe Leu Ser Pro Leu Leu Ala Val Pro Leu Ile Leu Ile Gly Lys Glu
        115                 120                 125

Leu Asn Ala Ser Lys Ala Gly Phe Ile Ala Ala Leu Leu Ala Ile Ile
    130                 135                 140

Ala Asn Ser Tyr Tyr Asn Arg Thr Met Ser Gly Tyr Tyr Asp Thr Asp
145                 150                 155                 160

Met Leu Asn Ile Thr Leu Pro Met Met Val Phe Trp Ser Ile Thr Arg
                165                 170                 175

Leu Val Gln Arg Lys Glu Arg Val Asn Leu Ile Phe Ile Pro Val Phe
            180                 185                 190

Met Ala Ile Tyr Gly Trp Trp Tyr Pro Ser Ser Tyr Ser Leu Leu Leu
        195                 200                 205

Ala Met Ile Gly Met Phe Phe Leu Tyr Thr Ile Val Phe Glu Arg Tyr
    210                 215                 220

Glu Lys Leu Asn Tyr Glu Ala Met Val Phe Met Ile Leu Ala Ile Thr
225                 230                 235                 240

Ser Phe Ser Ile Gln Ile Lys Phe Ile Ile Val Ile Val Leu Tyr Ala
                245                 250                 255

Leu Ile Tyr Phe Tyr Gln Arg Phe Phe Asp Lys Lys Val Ile Phe Ala
            260                 265                 270

Leu Ile Met Ala Ser Leu Ile Cys Phe Ile Trp Leu Gly Gly Leu Asn
        275                 280                 285

Pro Ile Leu Phe Asn Ile Lys Phe Tyr Ile Phe Arg Asp Ile Ala Asp
    290                 295                 300

Ser Gly Asp Ala Val Phe Lys Phe Phe Asn Val Asn Gln Thr Ile Arg
305                 310                 315                 320

Glu Ser Ser Ala Ile Asp Phe Asn Thr Val Val Thr Arg Ile Ser Gly
                325                 330                 335

His Leu Ile Val Phe Leu Val Ser Ile Ile Gly Tyr Ile Leu Phe Ile
            340                 345                 350

Lys Asn Asn Lys Ile Leu Leu Leu Thr Leu Pro Ile Leu Phe Leu Gly
        355                 360                 365

Leu Met Ser Phe Lys Ser Gly Leu Arg Phe Thr Ile Tyr Ser Val Pro
    370                 375                 380

Val Met Ala Leu Gly Phe Gly Tyr Phe Val Met Tyr Cys Phe Ala Lys
385                 390                 395                 400

Ile Asp Ile Lys Asp Arg Phe Leu Gly Tyr Val Phe Leu Phe Val Val
                405                 410                 415

Thr Phe Ser Ala Leu Tyr Pro Ser Leu Lys His Ile Tyr Asp Tyr Lys
            420                 425                 430

Val Phe Pro Val Phe Thr His Ser Glu Val Glu Ser Leu Asp Asn Leu
        435                 440                 445

Lys Asn Ile Ala Lys Arg Glu Asp Tyr Val Leu Ser Trp Trp Asp Tyr
    450                 455                 460
```

```
Gly Tyr Pro Ile Arg Tyr Tyr Ser Asp Val Lys Thr Leu Ile Asp Gly
465                 470                 475                 480

Gly Lys His Leu Gly Ser Asp Asn Phe Ala Val Ser Phe Ala Leu Gly
                485                 490                 495

Ser Asp Gln Asn Ser Ser Ala Asn Met Ala Arg Leu Glu Val Glu Tyr
            500                 505                 510

Thr Glu Lys Asn Tyr Glu Glu Lys Phe Gly Leu Asn Leu Lys Lys Met
        515                 520                 525

Met Lys Asp Tyr Asn Ala Thr Asn Val Asn Glu Phe Leu Leu Ser Leu
    530                 535                 540

Lys Asp Glu Asn Leu Thr Leu Pro Lys Gln Thr Arg Asp Ile Tyr Tyr
545                 550                 555                 560

Tyr Leu Pro Asp Arg Met Ile Tyr Ile Tyr Pro Ile Val Leu Asp Phe
                565                 570                 575

Ser Arg Leu Asp Leu Thr Thr Gly Gln Glu Phe Ala Gln Pro Phe Phe
            580                 585                 590

Met Val Ser Glu Arg Phe Ser Ala Thr Asn Asp Asn Gln Ile Met Leu
        595                 600                 605

Asn Asn Asn Val Ile Leu Ser Asn Asp Gly Thr Lys Leu Ser Ile Asn
    610                 615                 620

Gly Asn Ser Tyr Ser Val Asn Thr Tyr Val Glu Thr Ser Tyr Asp Gln
625                 630                 635                 640

Asn Glu Lys Leu Asn Val Asn Tyr Phe Asn Ile Asp Pro Asn Ser Asn
                645                 650                 655

Phe Tyr Val Ile Phe Met Lys Asp Tyr Leu Arg Ile Leu Val Leu Asp
            660                 665                 670

Lys Thr Leu Tyr Asp Ser Ala Tyr Ile Gln Leu Phe Val Leu Glu Asn
        675                 680                 685

Tyr Asp Lys Asn Leu Phe Glu Pro Val Ile Leu Asn Gly Ser Thr Lys
    690                 695                 700

Ile Tyr Lys Leu Lys Lys
705                 710


<210> SEQ ID NO 25
<211> LENGTH: 2133
<212> TYPE: DNA
<213> ORGANISM: Campylobacter sputorum

<400> SEQUENCE: 25

atgtcaaatt ttaatttcgc taaatttcta aataaattac ctagactttc taaacatact     60

atattaatga ttgttttagc tgtttgtttt gggatatttt gcagatttta ctgggtagtt    120

tgggctagtg cttatcccca ttttatatgg aatgatgaac ttatgataag tacaaatgat    180

ggatatgcat ttgctgaggg cacaagagat atgatagctg gttttcatca accaaacgat    240

ctttcttact atggctcatc tctttctaca cttagcatgt ggctatatag cattttgcca    300

ttttcattag aaactatact tttgtatatg agtacatttt tatctccact attagctgtg    360

cctttgatac ttataggtaa agaactaaac gcttcaaaag ctggatttat agctgcactt    420

ctagctgttg ttgcaaatag ttattataat agaacaatga gtggatatta tgatacagat    480

atgctaaata ttactcttcc tatgatggtt ttttggagca taacaagact tgttcaaaga    540

aaagagagag taaatttaat atttattcca gtttttatgg cgatatatgg atggtggtat    600

ccatcttctt actcactatt actcgcaatg attgggatgt ttgttttata taccattgtt    660
```

-continued

```
tttgaaagat atgaaaaact aaactatgaa gctatggttt ttatgatttt ggcaatcaca    720

agctttccta tacaaatcaa atttattata gttattattt tgtatgcttt gatctatttt    780

tatcaaagat tttttgataa aaaagtaata tttgcattaa ttatagcttc atcaatatgc    840

tttatatggc ttggcggatt aaatcctata ctttttaaca ttaaatttta tatatttaga    900

gacattgcag atagtggtga tactgttttt aaatttttca atgtaaatca aacaataaga    960

gaaagttccg cgatagattt taatacagtt gcaactagga ttagtgggca tttgatagta   1020

tttttggtat ctattgtagg atatatttta tttataaaaa acaataaaat tttactacta   1080

actttaccga ttctattttt aggtcttatg tcatttaaaa gtggtttaag atttacaata   1140

tactcagttc cagtaatggc ccttggtttt ggttattttg ttatgtattg ttttacaaag   1200

atagatataa aagatcgttt tttaggttat gcatttttat ttgttgtaac atttagtgca   1260

ttatatccat ctttaaaaca tatttatgat tataaggtat ttcctgtttt tacacatagc   1320

gaagttgaaa gtttggatga tttaaaaaat attgcaaaaa gagaagatta tgtgctttct   1380

tggtgggatt atggttatcc aataagatat tattctgatg taaaaactct catagatgga   1440

ggaaaacatc taggaagtga taacttcgca gttagctttg cacttggaag cgatcaaaac   1500

agctctgcaa atatggcaag attagaagtt gagtatacag aaagaaatta tgaggaaaaa   1560

tttggattaa atttaaaaca gattatgaaa gattataatg ctacaaatgt taatgagttt   1620

ttattatcat taaaagatgc aaatttagct ctgccaaagc aaacaagaga tatttattac   1680

tatttaccag atagaatgat atacatatat ccaacagtgc tagctttttc tagacttgat   1740

ttgacaacag ggcaagaatt tgctgagccg tttttatag ttagtgagag attttcagct    1800

acaaatgata atcaaataat gttaaataat aatgttatat taagtagtga tggcactaaa   1860

ttatcaataa atggaaactc ttatagtgta aatacatatg tagaaacaag ttatgatcaa   1920

aatgaaaaat taaatgtaaa ttattttaac atagatccaa atagcaattt ttatgtgatt   1980

tttatgaaag attatttgag aattttggtt ttagataaaa ctttatatga tagtgcgtat   2040

attcaacttt ttgtattaga aaattatgat aaaaatttat ttgaaccagt gattttaaac   2100

ggatcaacta aaatttataa actcaaaaaa tga                                2133
```

<210> SEQ ID NO 26
<211> LENGTH: 2133
<212> TYPE: DNA
<213> ORGANISM: Campylobacter sputorum

<400> SEQUENCE: 26

```
atgagtaatt ttaattttgc caaatttctg aacaagctgc ctagactaag caaacatacc     60

atcctgatga tcgtgctggc ggtgtgcttt ggcatctttt gtcgctttta ttgggttgtg    120

tgggcgagtg cgtatccaca ttttatttgg aatgatgaac tgatgatctc tacaaatgat    180

ggctatgcgt ttgcggaagg tacacgcgat atgattgccg gctttcatca gccgaatgat    240

ctgtcatatt atggtagttc actgtccact ttaagcatgt ggctgtatag catcctgccg    300

ttttcattag aaaccatctt actgtatatg tcaacgtttc tgagtccact gctggcagtt    360

ccgttaatct taatcggtaa agaactgaat gcgtctaaag caggctttat tgcagccctg    420

ctggcagttg tggccaatag ctattataat cgcaccatgt caggctatta tgatacggat    480

atgctgaata tcaccttacc gatgatggtg ttttggagca tcacccgcct ggttcagcgc    540

aaagaacggg ttaatctcat ctttattcca gtgtttatgg ccatctatgg ttggtggtat    600

ccatcttcat attcactgct gctggccatg atcggcatgt ttgtgctgta taccatcgtg    660
```

```
tttgaacgct atgaaaaact gaattatgaa gcaatggtgt ttatgattct ggcaatcact    720
agctttccga ttcagatcaa gtttatcatc gtgatcattc tgtatgcgtt aatctatttt    780
tatcagcgct ttttcgataa aaaagttatc tttgccttaa tcattgcaag tagcatttgc    840
tttatttggt taggcggctt aaatccaatc ctgtttaata tcaaatttta tatctttcgc    900
gacatagcgg attcaggcga tacggtgttt aaattcttca atgtgaatca gaccattcgc    960
gaaagtagcg ccatcgattt taatacagtt gcgacccgca tctcaggtca tctgattgtg   1020
tttctggtga gcatcgtggg ctatatcctg tttatcaaaa acaacaagat tttactgctg   1080
accttaccga tcctgtttct gggtctgatg tcgtttaaaa gcggcctgcg ctttacaatc   1140
tatagcgttc ctgtaatggc gttaggcttt ggctattttg tgatgtattg ctttacgaaa   1200
atcgacatca aagatcgctt tctgggctat gcctttctgt ttgtggtgac ctttagtgcc   1260
ctgtatccgt cactgaaaca tatctatgat tacaaggtgt ttccagtgtt tacacatagc   1320
gaagtggaaa gcctggatga tctgaaaaat attgccaaac gcgaagatta tgtgctgtct   1380
tggtgggatt atggctatcc gattcgctat tatagcgatg ttaaaacact gatcgatggc   1440
ggtaaacatc taggttcaga taattttgcc gtgagctttg cactgggcag cgatcagaat   1500
agtagtgcaa atatggcccg cttagaagtg gaatatacgg aacgcaatta tgaagaaaaa   1560
tttggtctga atctgaaaca gatcatgaaa gattataatg caaccaatgt gaatgagttt   1620
ctgctgtctc tgaaagatgc caacctggcc ctgcctaaac agacacgcga tatatattat   1680
tatctgccgg atcgcatgat ctatatctat cctacagtgt tagcctttag tcgcctggat   1740
ctgacgacgg gccaggaatt tgcagaaccg tttttcatcg tgagcgaacg ctttagtgca   1800
accaatgata atcagatcat gttaaacaac aatgtgattc tttcatcaga tggaacaaaa   1860
ctgtcaatca atggcaatag ctattcagtt aatacttatg tagaaaccag ctacgatcag   1920
aacgaaaaac tgaatgttaa ttattttaat atcgatccga atagcaattt ttatgtgatc   1980
tttatgaaag attatctgcg catcttagtt ctggataaaa ccctgtatga tagcgcgtat   2040
atccagctgt ttgtgctgga aaattatgat aaaaatctgt ttgaaccagt catcctgaat   2100
ggtagtacga aaatctataa gctgaaaaaa taa                                2133
```

<210> SEQ ID NO 27
<211> LENGTH: 710
<212> TYPE: PRT
<213> ORGANISM: Campylobacter sputorum

<400> SEQUENCE: 27

```
Met Ser Asn Phe Asn Phe Ala Lys Phe Leu Asn Lys Leu Pro Arg Leu
1               5                   10                  15

Ser Lys His Thr Ile Leu Met Ile Val Leu Ala Val Cys Phe Gly Ile
            20                  25                  30

Phe Cys Arg Phe Tyr Trp Val Val Trp Ala Ser Ala Tyr Pro His Phe
        35                  40                  45

Ile Trp Asn Asp Glu Leu Met Ile Ser Thr Asn Asp Gly Tyr Ala Phe
    50                  55                  60

Ala Glu Gly Thr Arg Asp Met Ile Ala Gly Phe His Gln Pro Asn Asp
65                  70                  75                  80

Leu Ser Tyr Tyr Gly Ser Ser Leu Ser Thr Leu Ser Met Trp Leu Tyr
                85                  90                  95

Ser Ile Leu Pro Phe Ser Leu Glu Thr Ile Leu Leu Tyr Met Ser Thr
            100                 105                 110
```

-continued

```
Phe Leu Ser Pro Leu Leu Ala Val Pro Leu Ile Leu Ile Gly Lys Glu
        115                 120                 125

Leu Asn Ala Ser Lys Ala Gly Phe Ile Ala Ala Leu Leu Ala Val Val
    130                 135                 140

Ala Asn Ser Tyr Tyr Asn Arg Thr Met Ser Gly Tyr Tyr Asp Thr Asp
145                 150                 155                 160

Met Leu Asn Ile Thr Leu Pro Met Met Val Phe Trp Ser Ile Thr Arg
                165                 170                 175

Leu Val Gln Arg Lys Glu Arg Val Asn Leu Ile Phe Ile Pro Val Phe
            180                 185                 190

Met Ala Ile Tyr Gly Trp Trp Tyr Pro Ser Ser Tyr Ser Leu Leu Leu
        195                 200                 205

Ala Met Ile Gly Met Phe Val Leu Tyr Thr Ile Val Phe Glu Arg Tyr
    210                 215                 220

Glu Lys Leu Asn Tyr Glu Ala Met Val Phe Met Ile Leu Ala Ile Thr
225                 230                 235                 240

Ser Phe Pro Ile Gln Ile Lys Phe Ile Ile Val Ile Ile Leu Tyr Ala
                245                 250                 255

Leu Ile Tyr Phe Tyr Gln Arg Phe Phe Asp Lys Lys Val Ile Phe Ala
            260                 265                 270

Leu Ile Ile Ala Ser Ser Ile Cys Phe Ile Trp Leu Gly Gly Leu Asn
        275                 280                 285

Pro Ile Leu Phe Asn Ile Lys Phe Tyr Ile Phe Arg Asp Ile Ala Asp
    290                 295                 300

Ser Gly Asp Thr Val Phe Lys Phe Phe Asn Val Asn Gln Thr Ile Arg
305                 310                 315                 320

Glu Ser Ser Ala Ile Asp Phe Asn Thr Val Ala Thr Arg Ile Ser Gly
                325                 330                 335

His Leu Ile Val Phe Leu Val Ser Ile Val Gly Tyr Ile Leu Phe Ile
            340                 345                 350

Lys Asn Asn Lys Ile Leu Leu Leu Thr Leu Pro Ile Leu Phe Leu Gly
        355                 360                 365

Leu Met Ser Phe Lys Ser Gly Leu Arg Phe Thr Ile Tyr Ser Val Pro
    370                 375                 380

Val Met Ala Leu Gly Phe Gly Tyr Phe Val Met Tyr Cys Phe Thr Lys
385                 390                 395                 400

Ile Asp Ile Lys Asp Arg Phe Leu Gly Tyr Ala Phe Leu Phe Val Val
                405                 410                 415

Thr Phe Ser Ala Leu Tyr Pro Ser Leu Lys His Ile Tyr Asp Tyr Lys
            420                 425                 430

Val Phe Pro Val Phe Thr His Ser Glu Val Glu Ser Leu Asp Asp Leu
        435                 440                 445

Lys Asn Ile Ala Lys Arg Glu Asp Tyr Val Leu Ser Trp Trp Asp Tyr
    450                 455                 460

Gly Tyr Pro Ile Arg Tyr Tyr Ser Asp Val Lys Thr Leu Ile Asp Gly
465                 470                 475                 480

Gly Lys His Leu Gly Ser Asp Asn Phe Ala Val Ser Phe Ala Leu Gly
                485                 490                 495

Ser Asp Gln Asn Ser Ser Ala Asn Met Ala Arg Leu Glu Val Glu Tyr
            500                 505                 510

Thr Glu Arg Asn Tyr Glu Glu Lys Phe Gly Leu Asn Leu Lys Gln Ile
        515                 520                 525
```

```
Met Lys Asp Tyr Asn Ala Thr Asn Val Asn Glu Phe Leu Leu Ser Leu
    530                 535                 540

Lys Asp Ala Asn Leu Ala Leu Pro Lys Gln Thr Arg Asp Ile Tyr Tyr
545                 550                 555                 560

Tyr Leu Pro Asp Arg Met Ile Tyr Ile Tyr Pro Thr Val Leu Ala Phe
                565                 570                 575

Ser Arg Leu Asp Leu Thr Thr Gly Gln Glu Phe Ala Glu Pro Phe Phe
            580                 585                 590

Ile Val Ser Glu Arg Phe Ser Ala Thr Asn Asp Asn Gln Ile Met Leu
        595                 600                 605

Asn Asn Asn Val Ile Leu Ser Ser Asp Gly Thr Lys Leu Ser Ile Asn
    610                 615                 620

Gly Asn Ser Tyr Ser Val Asn Thr Tyr Val Glu Thr Ser Tyr Asp Gln
625                 630                 635                 640

Asn Glu Lys Leu Asn Val Asn Tyr Phe Asn Ile Asp Pro Asn Ser Asn
                645                 650                 655

Phe Tyr Val Ile Phe Met Lys Asp Tyr Leu Arg Ile Leu Val Leu Asp
            660                 665                 670

Lys Thr Leu Tyr Asp Ser Ala Tyr Ile Gln Leu Phe Val Leu Glu Asn
        675                 680                 685

Tyr Asp Lys Asn Leu Phe Glu Pro Val Ile Leu Asn Gly Ser Thr Lys
    690                 695                 700

Ile Tyr Lys Leu Lys Lys
705                 710
```

<210> SEQ ID NO 28
<211> LENGTH: 71
<212> TYPE: DNA
<213> ORGANISM: artificial sequence
<220> FEATURE:
<223> OTHER INFORMATION: primer

<400> SEQUENCE: 28

```
gtgaatttac tgacagtgag tactgatctc atcagtattt ttttattcac tgtgtaggct     60

ggagctgctt c                                                          71
```

<210> SEQ ID NO 29
<211> LENGTH: 2112
<212> TYPE: DNA
<213> ORGANISM: Pseudomonas aeruginosa

<400> SEQUENCE: 29

```
atgaaaaaga tttggctggc gctggctggt ttagttttag cgtttagcgc tagcgatcag     60

aacgcgaccg gcggtgacca aaatgccaca ggtggcgatc aaaacgccac cggcggtgac    120

cagaatgcga cagccgccga ggaagccttc gacctctgga acgaatgcgc caaggcctgc    180

gtgctcgacc tcaaggacgg cgtgcgttcc agccgcatga gcgtcgaccc ggccatcgcc    240

gacaccaacg gccagggcgt gctgcactac tccatggtcc tggagggcgg caacgacgcg    300

ctcaagctgg ccatcgacaa cgccctcagc atcaccagcg acggcctgac catccgcctc    360

gaaggcggcg tcgagccgaa caagccggtg cgctacagct acacgcgcca ggcgcgcggc    420

agttggtcgc tgaactggct ggtaccgatc ggccacgaga agccctcgaa catcaaggtg    480

ttcatccacg aactgaacgc cggtaaccag ctcagccaca tgtcgccgat ctacaccatc    540

gagatgggcg acgagttgct ggcgaagctg gcgcgcgatg ccaccttctt cgtcagggcg    600

cacgagagca acgagatgca gccgacgctc gccatcagcc atgccggggt cagcgtggtc    660
```

atggctcagg cccagccgcg ccgggaaaag cgctggagcg aatgggccag cggcaaggtg 720
ttgtgcctgc tcgacccgct ggacggggtc tacaactacc tcgcccagca gcgctgcaac 780
ctcgacgata cctgggaagg caagatctac cgggtgctcg ccggcaaccc ggcgaagcat 840
gacctggaca tcaaggataa taataattct actcccacgg tcatcagtca tcgcctgcat 900
ttccccgagg gcggcagcct ggccgcgctg accgcgcacc aggcctgcca cctgccgctg 960
gaggccttca ctcgtcatcg ccagccgcgc ggctgggaac aactggagca gtgcggctat 1020
ccggtgcagc ggctggtcgc cctctacctg gcggcgcgac tgtcgtggaa ccaggtcgac 1080
caggtgatcc gcaacgccct ggccagcccc ggcagcggcg gcgacctggg cgaagcgatc 1140
cgcgagcagc cggagcaggc ccgtctggcc ctgaccctgg ccgccgccga gagcgagcgc 1200
ttcgtccggc agggcaccgg caacgacgag gccggcgcgg ccagcgccga cgtggtgagc 1260
ctgacctgcc ccgtcgccaa agatcaaaat agaactaaag gggaatgcgc gggcccggcg 1320
gacagcggcg acgccctgct ggagcgcaac tatcccactg gcgcggagtt cctcggcgac 1380
ggcggcgacg tcagcttcag cacccgcggc acgcagaact ggacggtgga gcggctgctc 1440
caggcgcacc gccaactgga ggagcgcggc tatgtgttcg tcggctacca cggcaccttc 1500
ctcgaagcgg cgcaaagcat cgtcttcggc ggggtgcgcg cgcgcagcca ggacctcgac 1560
gcgatctggc gcggtttcta tatcgccggc gatccggcgc tggcctacgg ctacgcccag 1620
gaccaggaac ccgacgcgcg cggccggatc cgcaacggtg ccctgctgcg ggtctatgtg 1680
ccgcgctgga gtctgccggg cttctaccgc accggcctga ccctggccgc gccggaggcg 1740
gcgggcgagg tcgaacggct gatcggccat ccgctgccgc tgcgcctgga cgccatcacc 1800
ggccccgagg aggaaggcgg gcgcgtgacc attctcggct ggccgctggc cgagcgcacc 1860
gtggtgattc cctcggcgat ccccaccgac ccgcgcaacg tcggcggcga cctcgacccg 1920
tccagcatcc ccgacaagga acaggcgatc agcgccctgc cggactacgc cagccagccc 1980
ggcaaaccgc cgcgcgagga cttgaaggat cagaacgcga ccggcggtga ccaaaatgcc 2040
acaggtggcg atcaaaacgc caccggcggt gaccagaatg cgacagtcga ccatcaccat 2100
catcaccatt ga 2112

<210> SEQ ID NO 30
<211> LENGTH: 28
<212> TYPE: DNA
<213> ORGANISM: artificial sequence
<220> FEATURE:
<223> OTHER INFORMATION: Primer

<400> SEQUENCE: 30
ggatcattaa tagctaaatg tagtgctg 28

<210> SEQ ID NO 31
<211> LENGTH: 32
<212> TYPE: DNA
<213> ORGANISM: artificial sequence
<220> FEATURE:
<223> OTHER INFORMATION: Primer

<400> SEQUENCE: 31
ttttgaattc tacaggctgt caatggagaa tg 32

<210> SEQ ID NO 32
<211> LENGTH: 19
<212> TYPE: DNA

-continued

```
<213> ORGANISM: artificial sequence
<220> FEATURE:
<223> OTHER INFORMATION: primer

<400> SEQUENCE: 32

gcgctggctg gtttagttt                                              19


<210> SEQ ID NO 33
<211> LENGTH: 18
<212> TYPE: DNA
<213> ORGANISM: artificial sequence
<220> FEATURE:
<223> OTHER INFORMATION: primer

<400> SEQUENCE: 33

cgcattcgtt ccagaggt                                               18


<210> SEQ ID NO 34
<211> LENGTH: 20
<212> TYPE: DNA
<213> ORGANISM: artificial sequence
<220> FEATURE:
<223> OTHER INFORMATION: primer

<400> SEQUENCE: 34

gacaaggaac aggcgatcag                                             20


<210> SEQ ID NO 35
<211> LENGTH: 20
<212> TYPE: DNA
<213> ORGANISM: artificial sequence
<220> FEATURE:
<223> OTHER INFORMATION: primer

<400> SEQUENCE: 35

tggtgatgat ggtgatggtc                                             20
```

*FRANCISELLA* GLYCOCONJUGATE VACCINES

CROSS REFERENCE TO RELATED APPLICATIONS

This is a divisional of U.S. application Ser. No. 16/326,642, filed Feb. 19, 2019, which is the U.S. National Stage of International Application No. PCT/GB2017/052653, filed Sep. 11, 2017, which was published in English under PCT Article 21(2), which in turn claims the benefit of GB Application No. 1615427.0, filed Sep. 12, 2016.

FIELD OF THE INVENTION

The disclosure relates to a vaccine comprising aglycoconjugate antigenic polypeptides conferring protection against *Francisella tularensis* infections and a method of glycosylating a polypeptide antigen.

BACKGROUND TO THE INVENTION

Subunit vaccines, based on proteins or displayed on the surface of the pathogen are often preferred over inactivated or attenuated pathogens as they are known to cause fewer side effects. However, the development of a subunit vaccine is laborious requiring the identification and isolation of protective antigens from the pathogenic organism, and moreover subunit vaccines often invoke an immune response with low antibody titre, antibodies are short half-life and show low affinity for a specific antigen. It is known that the immunogenicity of polysaccharide antigens can be enhanced by conjugation to a protein carrier. Currently licensed human glycoconjugate vaccines include those against *Haemophilus influenzae, Neisserria meningitidis* and *Streptococcus pneumonia*. These glycoconjugate vaccines use bacterial polysaccharides that are chemically bound to carrier proteins. However, although these vaccines are effective, their production requires both the purification of polysaccharide glycan from the native pathogen and the chemical coupling of the sugar to a suitable protein carrier which can lead to low yields and variation between batches of conjugates making this process is highly costly, inefficient and time consuming.

Several pathogenic bacteria have been identified forming glycoproteins such as for example the Gram negative pathogenic bacterium *Campylobacter jejuni* which harbours a protein glycosylation locus comprising pglA-pglG known to be involved in the glycosylation of over 30 glycoproteins. Part of the gene cluster is PglB, an oligosaccharyltransferase catalysing the transfer of glycans on to a wide range of different non-species related protein acceptors indicating broad substrate specificity. Production of glycoconjugate vaccines comprising a protein carrier and an antigenic polysaccharide O-antigen from *Shigella, E. coli* and *Pseudomonas aeruginosa* using the oligosaccharyltransferase PglB in a bacterial system are disclosed in WO2009/104074.

Tularemia, also known as lemming or rabbit fever, is common in wild rodents and can be passed on to humans by contact with infected animal tissues, ticks or biting flies, or by inhalation of the infectious organism. Tularemia, a highly infectious disease with mortality rates up to 30% is found in North America, parts of Europe and Asia and is caused by the Gram-negative coccobacillus *Francisella tularensis*. The development of vaccines protective against *Francisella tularensis* infections are greatly desired as there are no effective treatment methods available. Lipopolysaccharide (LPS) comprising an O-antigen from *F. tularensis* has shown protective effects in a murine infection model. However, the development of glycoprotein vaccines protecting against highly infectious pathogens are often associated with high safety concerns. Our pending application U.S. Ser. No. 14/655,210 [WO2014/114926] the content of which is incorporated by reference in its entirety, discloses vaccine compositions comprising an antigenic polysaccharide isolated from *Francisella tularensis* which is linked to various carrier polypeptides. The glycoconjugates are produced by a bacterial protein glycan coupling technology (PGCT) that allows the safe production of protective vaccines from the highly virulent wild-type strains of *F. tularensis holarctica* and subsequent purification. These vaccines provide significant protection against subsequent challenges when compared to other LPS based vaccine treatments.

The disclosure relates to vaccines comprising alternative carriers with one or more glycosylation motifs for glycosylation. The glycosylated carriers show effective protection against *F. tularensis* infections. In addition we disclose whole cell glycosylation systems that use modified bacterial cells for the glycosylation of the carriers with *Francisella* O-antigen, in particular bacterial cells that have a non-functional Wec A gene or a non-functional Wec A protein and the effect of expressing genes involved in synthesizing *Francisella* O-antigen glycoconjugates in a Wec $A^+$ and Wec $A^-$ genetic background. Wec A is an integral membrane protein that catalyses the transfer of N-acetylglucosamine (GlcNAC)-1-phosphate to undecaprenyl phosphate (Und-P) to form Und-P-P-GlNAc [Lehrer et al (2007) Journal of Bacteriology 189: 2617-2628].

STATEMENT OF INVENTION

According to an aspect of the invention there is provided a vaccine composition comprising: a carrier polypeptide comprising one or more T-cell dependent epitopes and one or more amino acid sequences having at least one amino acid motif comprising the amino acid sequence D/E-X-N-X-S/T wherein X is any amino acid except proline and crosslinked to said carrier polypeptide an antigenic polysaccharide wherein the polysaccharide is isolated from *Francisella* and is an O-antigen.

According to an aspect of the invention there is provided an immunogenic composition comprising: a carrier polypeptide comprising one or more T-cell dependent epitopes and one or more amino acid sequences having the amino acid motif D/E-X-N-X-S/T wherein X is any amino acid except proline and crosslinked to said carrier polypeptide is an antigenic polysaccharide wherein the polysaccharide is isolated from *Francisella* and is an O-antigen.

The term "carrier" is construed in the following manner. A carrier is an immunogenic molecule which, when bound to a second molecule, augments immune responses to the latter. Some antigens are not intrinsically immunogenic yet may be capable of generating antibody responses when associated with a foreign protein molecule such as keyhole-limpet haemocyanin or tetanus toxoid. Such antigens contain B-cell epitopes but no T cell epitopes. The protein moiety of such a conjugate (the "carrier" protein) provides T-cell epitopes which stimulate helper T-cells that in turn stimulate antigen-specific B-cells to differentiate into plasma cells and produce antibody against the antigen. Examples of glycosylation motifs are set out in SEQ ID NO: SEQ ID NO: 18, SEQ ID NO 19, SEQ ID NO: 20 and SEQ ID NO: 21 and are merely illustrative.

In a preferred embodiment of invention said O-antigen comprises:

2-acetamido-2-deoxy-O-D-galacturonamide, 4,6-dideoxy-4-formamido-D-glucose and/or 2-acetamido-2,6-dideoxy-O-D-glucose and/or N-acetyl glucosamine.

In a preferred embodiment of the invention said O-antigen comprises or consists of:

4)-α-D-GalNAcAN-(1-4)-α-D-GalNAcAN-(1-3)-β-D-QuiNAc-(1-2)-β-D-Qui4NFm-(1-), wherein GalNAcAN is 2-acetamido-2-deoxy-O-D-galacturonamide, Qui4NFm is 4,6-dideoxy-4-formamido-D-glucose and the reducing end group QuiNAc is 2-acetamido-2,6-dideoxy-O-D-glucose.

In an alternative embodiment of the invention said O-antigen comprises or consists of:

4)-α-D-GalNAcAN-(1-4)-α-D-GalNAcAN-(1-3)-β-D-GlcNAc-(1-2)-β-D-Qui4NFm-(1-), wherein GalNacAN is 2-acetomido-2-deoxy-O-D-galacturonamide, Qui4NFm is 4,6-dideoxy-4-formamido-D-glucose and the reducing end group GlcNAc is N-acetyl glucosamine.

In a preferred embodiment of the invention said O-antigen is a tetrasaccharide.

In a preferred embodiment of the invention said carrier polypeptide, or polymorphic sequence variant, comprises an amino acid sequence as set forth in of SEQ ID NO: 1 or a polypeptide fragment comprising one or more glycosylation motifs.

In a preferred embodiment of the invention said carrier polypeptide, or polymorphic sequence variant, comprises an amino acid sequence as set forth in of SEQ ID NO: 2 or a polypeptide fragment comprising one or more glycosylation motifs.

In a preferred embodiment of the invention said carrier polypeptide, or polymorphic sequence variant, comprises an amino acid sequence as set forth in of SEQ ID NO: 3 or a polypeptide fragment comprising one or more glycosylation motifs.

In a preferred embodiment of the invention said carrier polypeptide, or polymorphic sequence variant, comprises an amino acid sequence as set forth in of SEQ ID NO: 4 or a polypeptide fragment comprising one or more glycosylation motifs.

In a preferred embodiment of the invention said carrier polypeptide, or polymorphic sequence variant, comprises an amino acid sequence as set forth in of SEQ ID NO: 5 or a polypeptide fragment comprising one or more glycosylation motifs.

In a preferred embodiment of the invention said carrier polypeptide, or polymorphic sequence variant, comprises an amino acid sequence as set forth in of SEQ ID NO: 6 or a polypeptide fragment comprising one or more glycosylation motifs.

In a preferred embodiment of the invention said carrier polypeptide, or polymorphic sequence variant, comprises an amino acid sequence as set forth in of SEQ ID NO: 7, or a polypeptide fragment comprising one or more glycosylation motifs.

"Polymorphic sequence variant" is a nucleotide or amino acid sequence variant that varies from a nucleotide or amino acid sequence and encodes or has an activity comparable or enhanced when compared to the subject sequence. Typically, polymorphic sequences comprise nucleotide or amino acid sequences that are at least 90%, 91%, 92%, 93%, 94%, 95%, 96%, 97%, 98% or 99% identical over the full length sequence or part thereof.

"Polypeptide fragment" is a fragment of a full length polypeptide but comprises at least one glycosylation motif and is at least 20, 30, 40, 50, 60, 70, 80, 90 or 100 amino acids in length.

In an alternative embodiment of the invention said carrier polypeptide comprises an amino acid sequence as set forth in SEQ ID NO: 1, 2, 3, 4, 5, 6, or 7.

In a preferred embodiment of the invention said composition includes an adjuvant.

In a preferred embodiment of the invention said adjuvant is selected from the group consisting of: cytokines selected from the group consisting of e.g. GMCSF, interferon gamma, interferon alpha, interferon beta, interleukin 12, interleukin 23, interleukin 17, interleukin 2, interleukin 1, TGF, TNFα, and TNFβ.

In a further alternative embodiment of the invention said adjuvant is a TLR agonist such as CpG oligonucleotides, flagellin, monophosphoryl lipid A, poly I:C and derivatives thereof.

In a preferred embodiment of the invention said adjuvant is a bacterial cell wall derivative such as muramyl dipeptide (MDP) and/or trehalose dycorynemycolate (TDM).

In a preferred embodiment of the invention said adjuvant is an aluminium based adjuvant suitable for use in a human subject.

In a preferred embodiment of the invention said adjuvant is selected from the group of consisting of: aluminium hydroxide, aluminium phosphate or calcium phosphate.

Adjuvants (immune potentiators or immunomodulators) have been used for decades to improve the immune response to vaccine antigens. The incorporation of adjuvants into vaccine formulations is aimed at enhancing, accelerating and prolonging the specific immune response to vaccine antigens. Advantages of adjuvants include the enhancement of the immunogenicity of weaker antigens, the reduction of the antigen amount needed for a successful immunisation, the reduction of the frequency of booster immunisations needed and an improved immune response in elderly and immunocompromised vaccinees. Selectively, adjuvants can also be employed to optimise a desired immune response, e.g. with respect to immunoglobulin classes and induction of cytotoxic or helper T lymphocyte responses. In addition, certain adjuvants can be used to promote antibody responses at mucosal surfaces. Aluminium hydroxide and aluminium or calcium phosphate has been used routinely in human vaccines. More recently, antigens incorporated into IRIV's (immunostimulating reconstituted influenza virosomes) and vaccines containing the emulsion-based adjuvant MF59 have been licensed in countries. Adjuvants can be classified according to their source, mechanism of action and physical or chemical properties. The most commonly described adjuvant classes are gel-type, microbial, oil-emulsion and emulsifier-based, particulate, synthetic and cytokines. More than one adjuvant may be present in the final vaccine product. They may be combined together with a single antigen or all antigens present in the vaccine, or each adjuvant may be combined with one particular antigen. The origin and nature of the adjuvants currently being used or developed is highly diverse. For example, aluminium based adjuvants consist of simple inorganic compounds, PLG is a polymeric carbohydrate, virosomes can be derived from disparate viral particles, MDP is derived from bacterial cell walls; saponins are of plant origin, squalene is derived from shark liver and recombinant endogenous immunomodulators are derived from recombinant bacterial, yeast or mammalian cells. There are several adjuvants licensed for veterinary vaccines, such as mineral oil emulsions that are too reactive for human use. Similarly, complete Freund's adjuvant, although being one of the most powerful adjuvants known, is not suitable for human use.

In a preferred embodiment of the invention said composition includes at least one additional anti-bacterial agent.

In a preferred embodiment of the invention said additional anti-bacterial agent is a different antigenic molecule.

In a preferred embodiment of the invention said composition is a multivalent antigenic composition.

In an alternative preferred embodiment of the invention said additional anti-bacterial agent is an antibiotic.

In a preferred embodiment of the invention said vaccine or immunogenic composition is formulated to be delivered as an aerosol.

According to a further aspect of the invention there is provided a vaccine composition according to the invention for use in the prevention or treatment of a *Francisella* infection in a subject.

Preferably said infection is caused by *Francisella tularensis*.

In a preferred embodiment of the invention said vaccine composition is formulated to be delivered as an aerosol.

In a preferred embodiment of the invention said subject is an immune compromised subject.

According to a further aspect of the invention there is provided a method to treat a *Francisella* infection in a subject comprising administering an effective amount of a vaccine or immunogenic composition according to the invention.

Preferably said infection is caused by *Francisella tularensis*.

In a preferred method of the invention said vaccine composition is formulated to be delivered as an aerosol.

In a preferred method of the invention said subject is an immune compromised subject.

According to an aspect of the invention there is provided an antigenic polypeptide comprising: a carrier polypeptide comprising one or more T-cell dependent epitopes and one or more amino acid sequences having at least one amino acid motif comprising the amino acid sequence D/E-X-N-X-S/T wherein X is any amino acid except proline and linked to said carrier polypeptide is an antigenic polysaccharide wherein the polysaccharide is isolated from *Francisella* and is an O-antigen.

In a preferred embodiment of the invention said carrier polypeptide, or polymorphic sequence variant, comprises an amino acid sequence as set forth in of SEQ ID NO: 1, or a polypeptide fragment comprising one or more glycosylation motifs.

In a preferred embodiment of the invention said carrier polypeptide, or polymorphic sequence variant, comprises an amino acid sequence as set forth in of SEQ ID NO: 2, or a polypeptide fragment comprising one or more glycosylation motifs.

In a preferred embodiment of the invention said carrier polypeptide, or polymorphic sequence variant, comprises an amino acid sequence as set forth in of SEQ ID NO: 3, or a polypeptide fragment comprising one or more glycosylation motifs.

In a preferred embodiment of the invention said carrier polypeptide, or polymorphic sequence variant, comprises an amino acid sequence as set forth in of SEQ ID NO: 4, or a polypeptide fragment comprising one or more glycosylation motifs.

In a preferred embodiment of the invention said carrier polypeptide, or polymorphic sequence variant, comprises an amino acid sequence as set forth in of SEQ ID NO: 5, or a polypeptide fragment comprising one or more glycosylation motifs.

In a preferred embodiment of the invention said carrier polypeptide, or polymorphic sequence variant, comprises an amino acid sequence as set forth in of SEQ ID NO: 6, or a polypeptide fragment comprising one or more glycosylation motifs.

In a preferred embodiment of the invention said carrier polypeptide, or polymorphic sequence variant, comprises an amino acid sequence as set forth in of SEQ ID NO: 7, or a polypeptide fragment comprising one or more glycosylation motifs.

In a preferred embodiment of the invention said carrier polypeptide comprises an amino acid sequence as set forth in of SEQ ID NO: 1, 2, 3, 4, 5, 6, or 7.

In a preferred embodiment of invention said O-antigen comprises:

2-acetamido-2-deoxy-O-D-galacturonamide, 4,6-dideoxy-4-formamido-D-glucose and/or 2-acetamido-2,6-dideoxy-O-D-glucose and/or N-acetyl glucosamine.

In a preferred embodiment of the invention said O-antigen comprises or consists of:

4)-α-D-GalNAcAN-(1-4)-α-D-GalNAcAN-(1-3)-β-D-QuiNAc-(1-2)-β-D-Qui4NFm-(1-), wherein GalNAcAN is 2-acetamido-2-deoxy-O-D-galacturonamide, Qui4NFm is 4,6-dideoxy-4-formamido-D-glucose and the reducing end group QuiNAc is 2-acetamido-2,6-dideoxy-O-D-glucose.

In an alternative embodiment of the invention said O-antigen comprises or consists of:

4)-α-D-GalNAcAN-(1-4)-α-D-GalNAcAN-(1-3)-β-D-GlcNAc-(1-2)-β-D-Qui4NFm-(1-), wherein GalNacAN is 2-acetomido-2-deoxy-O-D-galacturonamide, Qui4NFm is 4,6-dideoxy-4-formamido-D-glucose and the reducing end group GlcNAc is N-acetyl glucosamine.

According to a further aspect of the invention there is provided a bacterial cell wherein said cell is genetically modified to include:

i) a nucleic acid molecule comprising the nucleotide sequence of the *Francisella* O-antigen biosynthetic polysaccharide locus [SEQ ID NO: 8];
ii) a nucleic acid molecule comprising a nucleotide sequence of an oligosaccharyltransferase; and/or
iii) a nucleic acid molecule comprising a nucleotide sequence of carrier polypeptide wherein the a carrier polypeptide comprising one or more T-cell dependent epitopes and one or more amino acid sequences having at least one amino acid motif comprising the amino acid sequence D/E-X-N-X-S/T wherein X is any amino acid except proline, wherein said bacterial cell is adapted for expression of each nucleic acid molecule and synthesizes an antigenic polypeptide according to the invention.

In a preferred embodiment said nucleic acid molecule encoding an oligosaccharyltransferase comprises a nucleotide sequence set forth in SEQ ID NO: 9, 23, 25 or 26, or a polymorphic sequence variant thereof, wherein said variant comprises a nucleic acid molecule the complementary strand of which hybridizes under stringent hybridization conditions to the sequence set forth in SEQ ID NO: 9, 23, 25 or 26 and wherein said nucleic acid molecule encodes an oligosaccharyltransferase.

In a preferred embodiment of the invention said carrier polypeptide, or polymorphic sequence variant, comprises an amino acid sequence as set forth in of SEQ ID NO: 1, or a polypeptide fragment comprising one or more glycosylation motifs.

In a preferred embodiment of the invention said carrier polypeptide, or polymorphic sequence variant, comprises an amino acid sequence as set forth in of SEQ ID NO: 2, or a polypeptide fragment comprising one or more glycosylation motifs.

In a preferred embodiment of the invention said carrier polypeptide, or polymorphic sequence variant, comprises an amino acid sequence as set forth in of SEQ ID NO: 3, or a polypeptide fragment comprising one or more glycosylation motifs.

In a preferred embodiment of the invention said carrier polypeptide, or polymorphic sequence variant, comprises an amino acid sequence as set forth in of SEQ ID NO: 4, or a polypeptide fragment comprising one or more glycosylation motifs.

In a preferred embodiment of the invention said carrier polypeptide, or polymorphic sequence variant, comprises an amino acid sequence as set forth in of SEQ ID NO: 5, or a polypeptide fragment comprising one or more glycosylation motifs.

In a preferred embodiment of the invention said carrier polypeptide, or polymorphic sequence variant, comprises an amino acid sequence as set forth in of SEQ ID NO: 6, or a polypeptide fragment comprising one or more glycosylation motifs.

In a preferred embodiment of the invention said carrier polypeptide, or polymorphic sequence variant, comprises an amino acid sequence as set forth in of SEQ ID NO: 7, or a polypeptide fragment comprising one or more glycosylation motifs.

In an alternative embodiment of the invention said carrier polypeptide comprises an amino acid sequence as set forth in of SEQ ID NO: 1, 2, 3, 4, 5, 6 or 7.

In a preferred embodiment of the invention said carrier polypeptide is encoded by a nucleic acid molecule comprising a nucleotide sequence as set forth in SEQ ID NO: 10, or a nucleic acid molecule the complementary strand of which hybridizes under stringent hybridization conditions to the sequence set forth in SEQ ID NO: 10.

In a preferred embodiment of the invention said carrier polypeptide is encoded by a nucleic acid molecule comprising a nucleotide sequence as set forth in SEQ ID NO: 11, or a nucleic acid molecule the complementary strand of which hybridizes under stringent hybridization conditions to the sequence set forth in SEQ ID NO: 11.

In a preferred embodiment of the invention said carrier polypeptide is encoded by a nucleic acid molecule comprising a nucleotide sequence as set forth in SEQ ID NO: 13 or a nucleic acid molecule the complementary strand of which hybridizes under stringent hybridization conditions to the sequence set forth in SEQ ID NO: 13.

In a preferred embodiment of the invention said carrier polypeptide is encoded by a nucleic acid molecule comprising a nucleotide sequence as set forth in SEQ ID NO: 14 or a nucleic acid molecule the complementary strand of which hybridizes under stringent hybridization conditions to the sequence set forth in SEQ ID NO: 14.

In a preferred embodiment of the invention said carrier polypeptide is encoded by a nucleic acid molecule comprising a nucleotide sequence as set forth in SEQ ID NO: 15 or a nucleic acid molecule the complementary strand of which hybridizes under stringent hybridization conditions to the sequence set forth in SEQ ID NO: 15.

In a preferred embodiment of the invention said carrier polypeptide is encoded by a nucleic acid molecule comprising a nucleotide sequence as set forth in SEQ ID NO: 16 or a nucleic acid molecule the complementary strand of which hybridizes under stringent hybridization conditions to the sequence set forth in SEQ ID NO: 16.

In a preferred embodiment of the invention said carrier polypeptide is encoded by a nucleic acid molecule comprising a nucleotide sequence as set forth in SEQ ID NO: 29 or a nucleic acid molecule the complementary strand of which hybridizes under stringent hybridization conditions to the sequence set forth in SEQ ID NO: 29.

In a preferred embodiment said bacterial cell expresses a glycosyltransferase encoded by a nucleic acid molecule comprising the nucleic acid sequence as set forth in SEQ ID NO 17, or a sequence variant thereof wherein said variant comprises a nucleic acid molecule the complementary strand of which hybridizes under stringent hybridization conditions to the sequence set forth in SEQ ID NO: 17 and wherein said nucleic acid molecule encodes an glycosyltransferase;

In a preferred embodiment said glycosyltransferase encoded by a nucleic acid molecule comprising the nucleic acid sequence set forth in SEQ ID NO 17 is modified wherein said modification is the addition, substitution or deletion of at least one nucleic acid base wherein said modified nucleic acid sequence encodes a glycosyltransferase polypeptide which has reduced or undetectable enzyme activity when compared to an unmodified glycosyltransferase polypeptide.

In a preferred embodiment of the invention said bacterial cell is deleted for all or part of the nucleic acid sequence set forth in SEQ ID NO: 17 to provide a non-functional glycosyltransferase polypeptide.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, NY, 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand.

The following is an exemplary set of hybridization conditions and is not limiting.

Very High Stringency (Allows Sequences that Share at Least 90% Identity to Hybridize)

a) Hybridization: 5×SSC at 65° C. for 16 hours
b) Wash twice: 2×SSC at room temperature (RT) for 15 minutes each
c) Wash twice: 0.5×SSC at 65° C. for 20 minutes each High Stringency (Allows Sequences that Share at Least 80% Identity to Hybridize)

a) Hybridization: 5×-6×SSC at 65° C.-70° C. for 16-20 hours
b) Wash twice: 2×SSC at RT for 5-20 minutes each
c) Wash twice: 1×SSC at 55° C.-70° C. for 30 minutes each Low Stringency (Allows Sequences that Share at Least 50% Identity to Hybridize)

i) Hybridization: 6×SSC at RT to 55° C. for 16-20 hours ii) Wash at least twice: 2×-3×SSC at RT to 55° C. for 20-30 minutes each.

A variant oligosaccharyltransferase polypeptide as herein disclosed may differ in amino acid sequence by one or more substitutions, additions, deletions, truncations that may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the same biological function and activity as the reference polypeptide from which it varies.

In one embodiment, the variant polypeptides have at least 50% or 55% identity, more preferably at least 60%, 65%, 70%, 75%, 80%, 85%, 90%, 95% identity, or at least 99% identity with the full length amino acid sequence illustrated herein.

In a preferred embodiment of the invention at least the oligosaccharyltransferase of ii) above is integrated into the bacterial genome to provide a stably transfected and expressing oligosaccharyltransferase.

In a further preferred embodiment of the invention one or more nucleic acid molecules encoding carrier polypeptides are also integrated into the bacterial genome.

According to a further aspect of the invention there is provided a bacterial cell culture comprising a genetically modified bacterial cell according to the invention.

According to a further aspect of the invention there is provided a process for the production of one or more glycoconjugates comprising:

i) providing a bacterial cell culture according to the invention;
ii) providing cell culture conditions; and
iii) isolating one or more glyconjugates from the bacterial cell or cell culture medium.

According to a further aspect of the invention there is provided a cell culture vessel comprising a bacterial cell culture according to the invention.

In a preferred embodiment of the invention said cell culture vessel is a fermentor.

Bacterial cultures used in the process according to the invention are grown or cultured in the manner with which the skilled worker is familiar, depending on the host organism. As a rule, bacteria are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The products produced can be isolated from the bacteria as described above by processes known to the skilled worker, for example by extraction, distillation, crystallization, if appropriate precipitation with salt, and/or chromatography. In this process, the pH value is advantageously kept between pH 4 and 12, preferably between pH 6 and 9, especially preferably between pH 7 and 8.

An overview of known cultivation methods can be found in the textbook Bioprocess technology 1. Introduction to Bioprocess technology (Gustav Fischer Verlag, Stuttgart, 1991) or in the textbook by Storhas (Bioreaktoren und periphere Einrichtungen [Bioreactors and peripheral equipment] (Vieweg Verlag, Brunswick/Wiesbaden, 1994)).

The culture medium to be used must suitably meet the requirements of the bacterial strains in question. Descriptions of culture media for various bacteria can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing bacteria usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF SUMMARY OF THE DRAWINGS

An embodiment of the invention will now be described by example only and with reference to the following figures:

FIG. 3: amino acid sequence of carrier protein DnaK (*Francisella tularensis*) (SEQ ID NO 2);

FIG. 4: amino acid sequence of carrier protein IglC (*Francisella tularensis*) (SEQ ID NO 1);

FIGS. 5A-5H: nucleotide sequence encoding the *Francisella* O-antigen biosynthetic polysaccharide (SEQ ID NO 8);

FIG. 6: nucleotide sequence encoding the oligosaccharyltransferase PglB (*C. jejuni*) (SEQ ID NO 9);

FIG. 7: Pgl B amino acid sequence (*C. jejuni*) (SEQ ID NO 22);

FIG. 8: nucleotide sequence of carrier protein DnaK (*Francisella tularensis*) (SEQ ID NO 11);

FIG. 9: nucleotide acid sequence of carrier protein IglC (*Francisella tularensis*) (SEQ ID NO 10);

FIG. 10: amino acid sequence of carrier protein ExoA (*Pseudomonas aeruginosa*) (SEQ ID NO 3);

FIG. 11: amino acid sequence of carrier protein TUL4 (*Francisella tularensis*) (SEQ ID NO 4);

FIG. 12: amino acid sequence of carrier protein FTT1713c (*Francisella tularensis*) (SEQ ID NO 5);

FIG. 13: amino acid sequence of carrier protein FTT1695 (*Francisella tularensis*) (SEQ ID NO 6);

FIG. 14: amino acid sequence of carrier protein FTT1696 (*Francisella tularensis*) (SEQ ID NO 7);

FIG. 15: PglB amino acid sequence (*C. jejuni*) (SEQ ID NO 22);

FIG. 16: nucleotide sequence encoding the oligosaccharyltransferase PglB (*Campylobacter sputorum*) (SEQ ID NO 23);

FIG. 17: amino acid sequence (full length) of PglB (*Campylobacter sputorum*) (SEQ ID NO 24).

FIGS. 18A-18C: *P. aeruginosa* ExoA with additional glycosylation sequons is heavily glycosylated by *F. tularensis* O-antigen by *C. jejuni* PglB in *E. coli* CLM24. Two-colour Western blots were used to simultaneously detect the degree of glycosylation of ExoA using monoclonal mouse mAb FB011 FIG. 18(A) (red) and rabbit anti-6× His FIG. 18(B) (green). The two IR secondary antibody channels when overlaid (IR 800/680) result in images with overall yellow colour indicating conjugation FIG. 18(C). Marker, PageRuler Plus Prestained protein ladder (Life technologies); Lane 1, pGVXN150 only; Lane 2, pGVXN150 ExoA glycosylated with the *F. tularensis* O-antigen (same construct from Cuccui et al., 2013); Lane 3, ExoA heavily glycosylated with the *F. tularensis* O-antigen due to additional terminal glycosylation sequons;

FIGS. 19A-19C: Survival (FIG. 19A) and disease of rats following aerosol challenge with a range of doses of *F. tularensis* Schu S4. Groups of 5 Fischer 344 rats were challenged via the aerosol route and monitored daily for mortality. Indicated challenge doses represent calculated dose from sampling of aerosol during challenge. Signs of disease in these animals were monitored twice daily Average cumulative signs for each group is presented for animals which had not succumbed to disease (FIG. 19B). Weight was monitored daily. Average weight change for each group is presented for animals which had not succumbed to disease (FIG. 19C);

BF=Brightfield

SSC=Side Scatter

Composite=CD45, CD3 and nucleus

*=p<0.01 by two-way ANOVA and Dunnett's post tests

Figure 21:
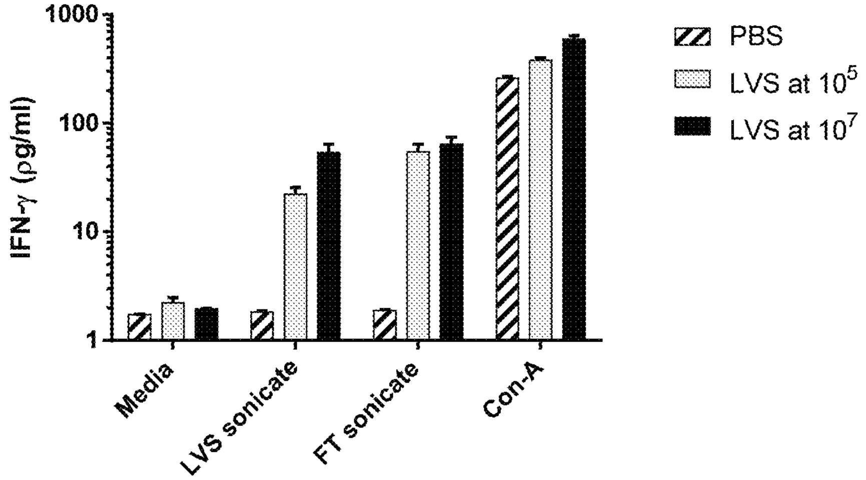
Figures 22A, 22B, 22C, 22D, 22E, 22F:
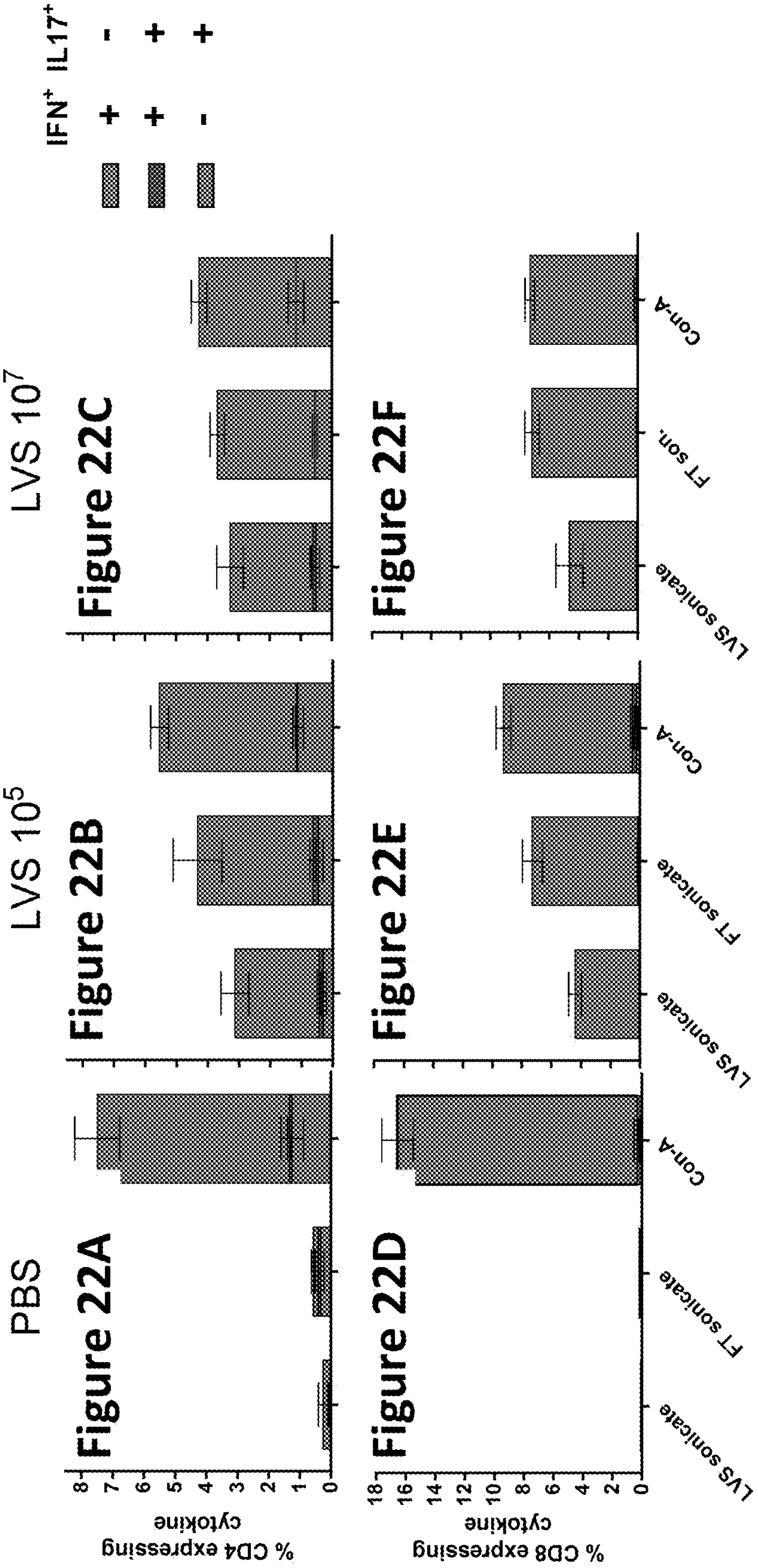
Figure 23:
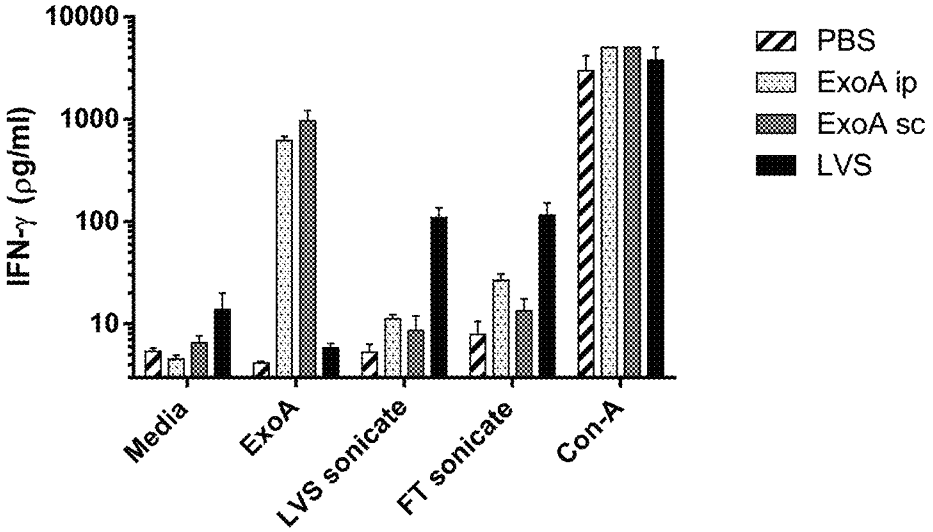
Figure 24A:
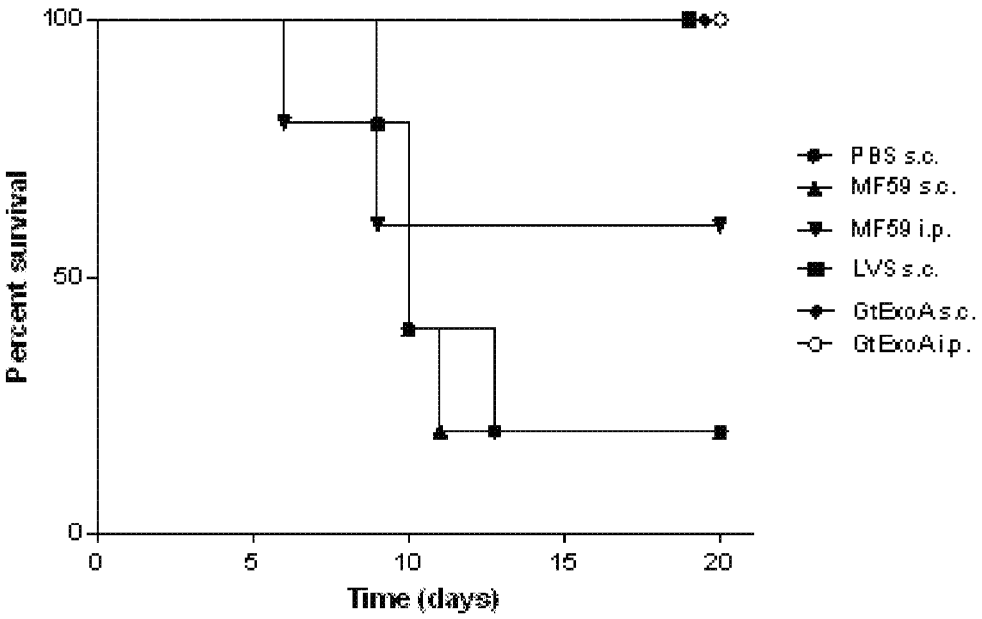
Figure 24B:
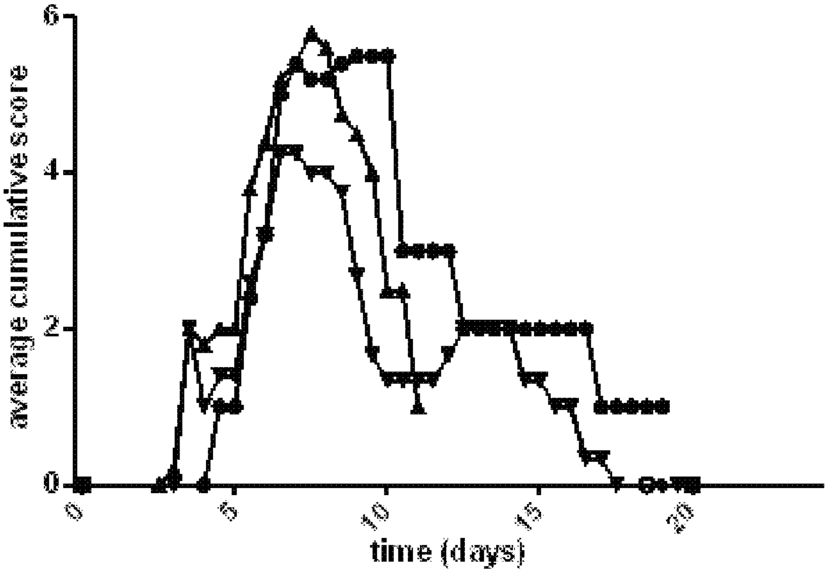
Figure 24C:
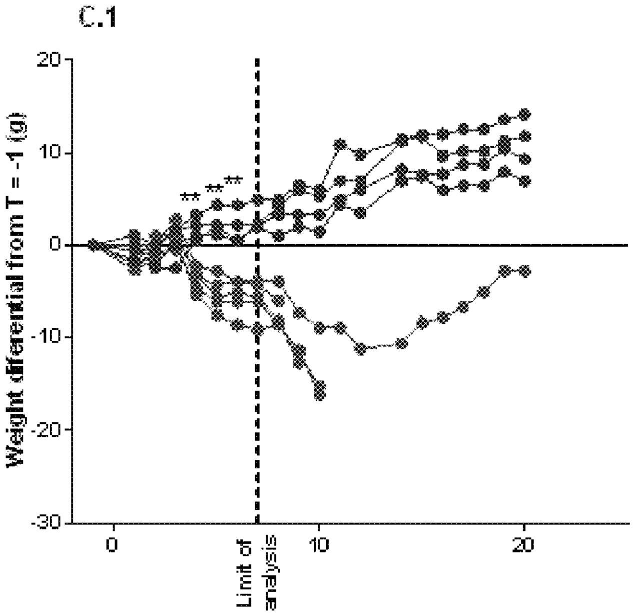
Figure 24D:
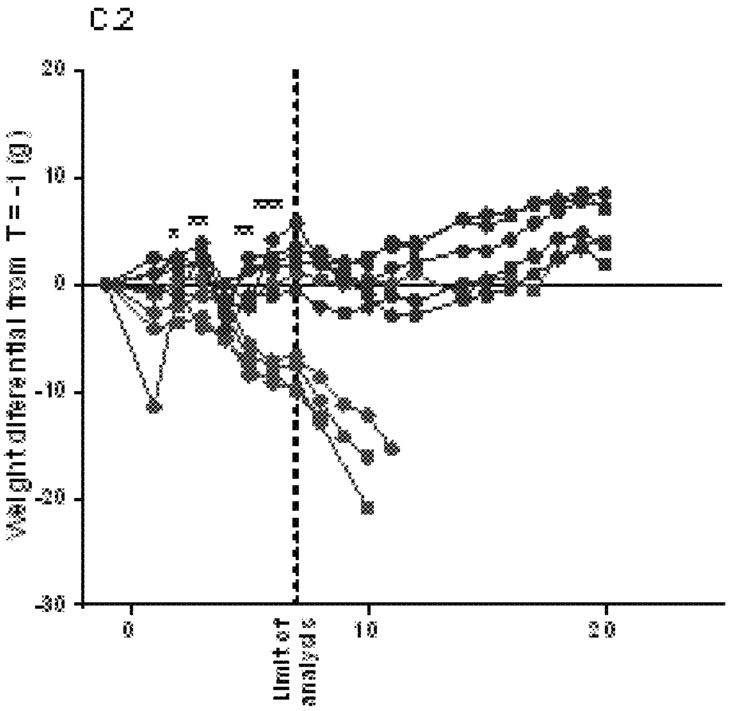
Figure 24E:
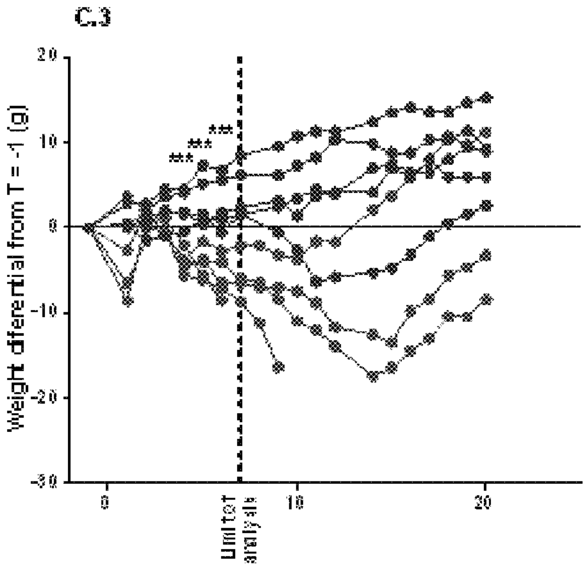
Figures 25A, 25B, 25C, 25D, 25E, 25F, 25G, 25H, 25I:
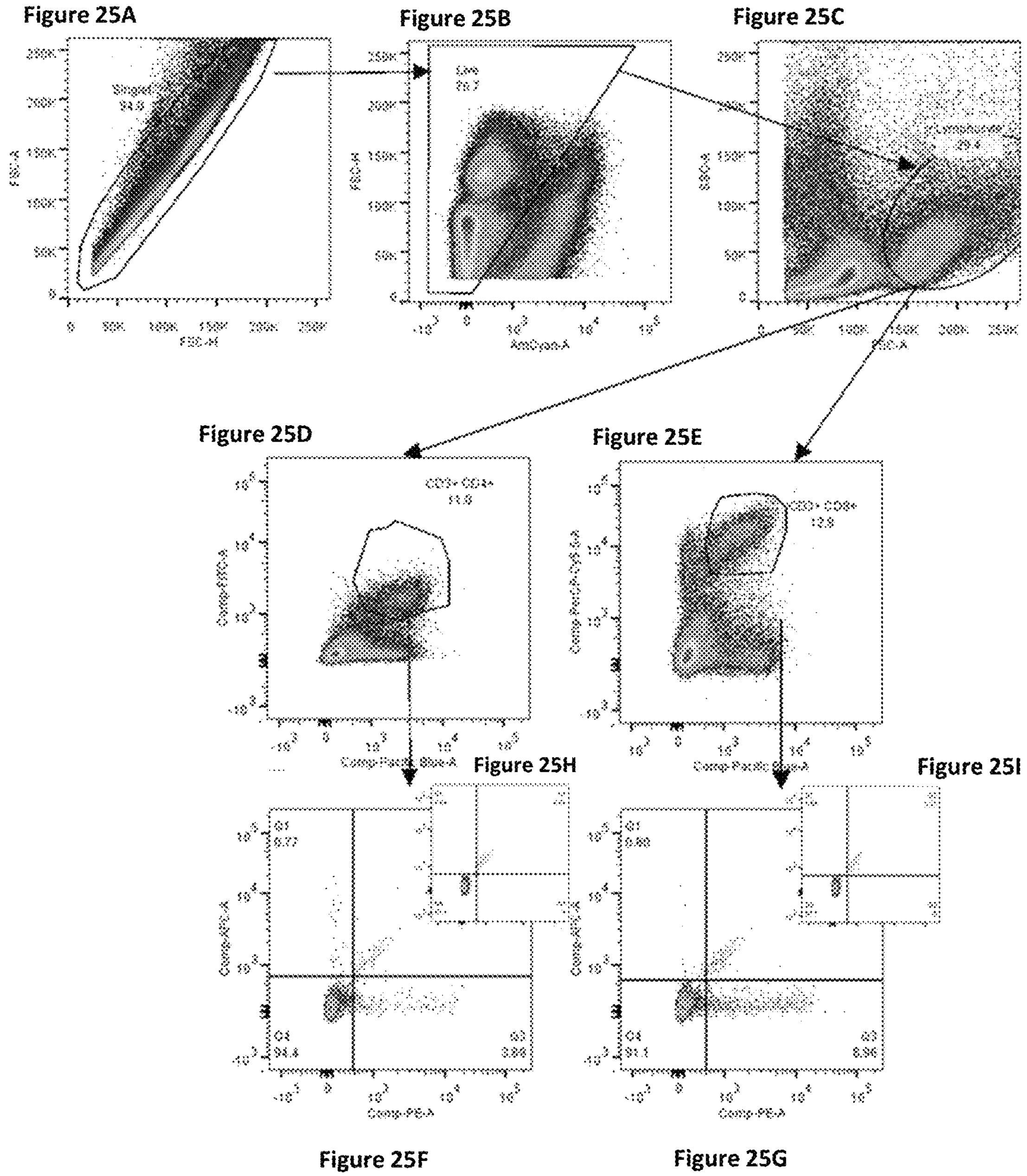

Images are representative of populations gated and fluorescence markers are optimised for visual impact with IDEAS®;

FIG. 21: Antigen stimulated IFNγ response in LVS infected rats. Splenocytes isolated from rats 21 days following infection with $10^5$ CFU LVS (grey bars), $10^7$ CFU LVS (black bars) or the PBS controls (hashed bars) were cultured in the presence of LVS sonicate, *F. tularensis* sonicate, Con-A or medium and then expression of IFNγ in 72 hour culture supernatants measured by ELISA. IFNγ responses (ρg/ml) are presented as mean response for each group (n=5)±SEM;

FIGS. 22A-22F: Measurement of antigen stimulated intracellular expression of IFNγ and IL17. Splenocytes isolated from LVS infected or PBS control rats 21 days-post infection were cultured in the presence of LVS sonicate, *F. tularensis* sonicate, Con-A or medium and then intracellular co-expression of IFNγ and/or IL17 was determined by flow cytometry. The percentage of antigen stimulated $CD4^+$ (FIGS. 22A-22C) and $CD8^+$ (FIGS. 22D-22F) T-cells expressing either IFN and/or IL17 is presented for each of the 3 treatment groups and for each of the antigens (medium control response subtracted). These data are presented by stacked bar graphs representing mean response for each group (n=5)±SEM;

FIG. 23: Antigen stimulated IFNγ response in glyco-conjugate vaccinated rats. Splenocytes isolated from rats immunised with glyco-conjugate vaccine administered i.p. (light grey bars) or s.c. (dark grey bars), and from rats infected with LVS (black bars) or the PBS controls (hashed bars) were cultured in the presence of LVS sonicate, *F. tularensis* sonicate, Con-A or medium. The expression of IFNγ in 72 hour culture supernatants was measured by ELISA. Responses were measured 6 weeks post vaccination for glyco-conjugate and PBS groups and 3 weeks post infection for the LVS group. IFNγ responses (ρg/ml) are presented as mean response for each group (n=5 except for LVS group where n=4)±SEM;

FIGS. 24A-24E: Protection of Fischer 344 rats against aerosol delivered Schu S4 with LVS and glyco-conjugate Groups of five Fischer 344 rats were vaccinated three times, two weeks apart with 10 μg glyco conjugate in MF59 or MF59 alone via the s.c. or i.p. route, or $5.38\times10^7$ LVS. 5 weeks after final vaccination, rats were challenged with $5.48\times10^2$ Schu S4 via the aerosol route and monitored twice daily for mortality (FIG. 24A). Signs of disease were recorded twice daily and average cumulative signs for surviving rats in each group of 5 presented (FIG. 24B). Rats were weighed once daily. Presented data is average weight change of surviving rats in groups of 5 (FIGS. 24C-24E). Each group is presented with its apposite control: LVS s.c. and PBS s.c. (FIG. 24C), G-tExoA+MF59 s.c. and MF59 s.c. (FIG. 24D), Gt-ExoA+MF59 i.p and MF59 i.p. (FIG. 24E). Significance in divergence of weight change between groups is denoted as * p<0.05,  p<0.005 and * p<0.0005 for each day; and FIGS. 25A-25I: Example gating strategy used to measure intracellular expression of IFNγ and IL17. Splenocytes were stimulated with either antigen (LVS and *F. tularensis* sonicates), mitogen (Con-A) or medium control prior to surface staining with rat CD3, CD4 and CD8 antibodies and then intracellular staining for IFNγ and IL17. Histograms were initially gated in accordance with the following hierarchy, singlet cells (FIG. 25A), live cells (FIG. 25B) and lymphocytes (FIG. 25C) prior to gating for co-expression for $CD3^+CD4^+$ and $CD3^+CD8^+$ (FIG. 25D and FIG. 25E, respectively). The example expression of IFNγ and IL17 from the $CD4^+$ and $CD8^+$ T-cell populations derived from splenocytes isolated from a rat infected with $10^7$ CFU LVS and then stimulated with *F. tularensis* sonicate antigen is presented in FIG. 25F and FIG. 25G. The equivalent response to the medium control stimulated splenocytes is shown in the corresponding inset FIG. 25H and FIG. 25I to demonstrate the antigen-specific nature of the $IFN\gamma^+$ and $IL17^+$ response presented.

TABLE 1

Summary of Sequence Information

| SEQ ID NO | Gene/protein |
|---|---|
| 1 | IgIC protein |
| 2 | DNAk protein |
| 3 | Exo A protein |
| 4 | Tul4 protein |
| 5 | FTT1713c protein |
| 6 | FTT1695 protein |
| 7 | FTT1696 protein |
| 8 | *Francisella* O antigen locus DNA |
| 9 | *Campylobacter jejuni* PgI B DNA |
| 10 | IgIC DNA |
| 11 | DNAk DNA |
| 12 | KnR |

TABLE 1-continued

| Summary of Sequence Information | |
|---|---|
| SEQ ID NO | Gene/protein |
| 13 | Tul4 DNA |
| 14 | FTT1713c DNA |
| 15 | FTT1695 DNA |
| 16 | FTT1696 DNA |
| 17 | Wec A |
| 18 | DXNXS |
| 19 | DXNXT |
| 20 | EXNXS |
| 21 | EXNXT |

TABLE 1-continued

| Summary of Sequence Information | |
|---|---|
| SEQ ID NO | Gene/protein |
| 22 | PgIB *C. jejuni* |
| 23 | PgIB1 *C. sputorum* |
| 24 | PgIB1 *C. sputorum* |
| 25 | PlgB2 *C. sputorum* |
| 26 | PlgB2 *C. sputorum* optimised |
| 27 | PgIB2 *C. sputorum* |
| 28 | KnF |
| 29 | ExoA DNA |

TABLE 2

| Strains and plasmids used | | |
|---|---|---|
| Strain/plasmid | Description | Source |
| *E. coli* Top10 | F-mcrA Δ(mrr-hsdRMS-mcrBC) φ80lacZΔM15 ΔlacX74 nupG recA1 araD139 Δ(ara-leu)7697 galE15 galK16 rpsL($Str^R$) endA1 $\lambda^-$ | Invitrogen |
| *E. coli* DH5α | F-φ80lacZΔM15 Δ(lacZYA-argF) U169 deoRrecA1 endA1 hsdR17 (rk−, mk+), gal-phoAsupE44λ-thi-1 gyrA96 relA1 | Invitrogen |
| *E. coli* XL-1 | endA1 gyrA96(nalr)thi-1 relA1 lac gln V44 F'[::Tn10 proAB+ laclq Δ (lacZ)M15] hsdR17 ($r_k^- m_k^+$) | Stratagene |
| *E. coli* CLM24 | rph-I IN(rrnD-rrnE) 1, ΔwaaL | 5 |
| *F. tularensis* subs. *tularensis* strain SchuS4 | Type A strain | DSTL, Porton Down laboratories |
| *F. tularensis* subs. *holarctica* strain HN63 | Type B strain, isolated in Norway from an infected Hare | Green, M., et al., Efficacy of the live attenuated *Francisella turlarenis* vaccine (LVS) in a murine model of disease. Vaccine, 2005. 23(20): p. 2680-6 |
| pGEM-T Easy | TA cloning vector, $amp^r$ | Promega |
| pGH | Vector construct GT-ExoA was synthesized in prior to subcloning into pGVXN150 | Celtek Bioscience, LLC |
| pLAFR1 | Low copy expression vector, $tet^r$ | Vanbleu E, Marchal K, Vanderleyden J. Genetic and physical map of the pLAFR1 vector. DNA Seq. 2004 June; 15(3): 225-7. |
| pGAB1 | *F. tularensis* O antigen coding region inserted into MCS of pGEM-T easy | This study |
| pGAB2 | *F. tularensis* subs. *tularensis* strain SchuS4 O antigen coding region inserted into Ecorl site of pLAFR. | This study |
| pGVXN114 | Expression plasmid for CjPgIB regulated from the Lac promoter in pEXT21. IPTG inducible, HA tag, $Spec^r$. | GlycoVaxyn |
| pGVXN115 | Expression plasmid for *C. jejuni*non functionalPgIB due to a mutation at $_{457}$WWDYGY$_{462}$ to | GlycoVaxyn |

TABLE 2-continued

| Strains and plasmids used | | |
|---|---|---|
| Strain/plasmid | Description | Source |
| | $_{457}$WAAYGY$_{462}$, regulated from the Lac promoter in pEXT21. IPTG inducible, HA tag, Spec$^r$. | |
| pGVXN150$_{260}$DNQNS$_{264}$ | Expression plasmid for *Pseudomonas aeruginosa* PA103 (DSM111/) Exotoxin A with the signal peptide of the *E. coli*DsbA protein, two inserted bacterial N-glycosylation sites, AA at position 262 altered from N to Q and a hexahis tag at the C-terminus. Induction under control of an arabinose inducible promoter, Amp$^r$ | This study |
| pGVXN150$_{402}$DQQRT$_{406}$ | Expression plasmid for *Pseudomonas aeruginosa* PA103 (DSM111/) Exotoxin A with the signal peptide of the *E. coli*DsbA protein, two inserted bacterial N-glycosylation sites, AA at position 404 altered from N to Q and a hexahis tag at the C-terminus. Induction under control of an arabinose inducible promoter, Amp$^r$ | This study |
| pGVXN150$_{260}$DNQNS$_{264}$/$_{402}$DQQRT$_{406}$ | Expression plasmid for *Pseudomonas aeruginosa* PA103 (DSM111/) Exotoxin A with the signal peptide of the *E. coli*DsbA protein, two inserted bacterial N-glycosylation sites, AA at position 262 and 404 altered from N to Q and a hexahis tag at the C-terminus. Induction under control of an arabinose inducible promoter, Amp$^r$ | This study |
| pGVXN150:GTExoA | Expression plasmid for *P. aeruginosa* PA103 Exotoxin A (ExoA) with the signal peptide of the *E. coli* DsbA protein, two inserted bacterial N-glycosylation sites, two extra terminal glycosylation sites on the N and C-termini, and a hexa-His tag at the C-terminus. Induction under control of an arabinose inducible promoter, Amp$^r$ | This study |
| pACYCpgl | pACYC184 carrying the CjPglB locus, Cm$^r$ | 5 |
| *E. coli* CedAPglB | *E. coli* strain CLM24 with a chromosomally inserted IPTG inducible copy of PglB | This study |
| pGVXN150 | Expression plasmid for *P. aeruginosa* PA103 ExoA with the signal peptide of the *E. coli* DsbA protein, two inserted bacterial N-glycosylation sites, and a hexa-His tag at the C-terminus. Induction under control of an arabinose inducible promoter, Amp$^r$ | GlycoVaxyn, Cuccui et al., 2013 |

Materials and Methods

Bacterial Strains

*Escherichia coli* strains were grown in LB at 37° C., 180 rpm for small scale tests, or 110 rpm for large scale vaccine production. Antibiotics and or supplements were used at the following concentrations; tetracycline 20 μg/ml, ampicillin 100 μg/ml, spectinomycin 80 μg/ml and chloramphenicol 30 μg/ml. The host strain for initial cloning experiments was *E. coli* XL-1, subsequent strains used for glycoconjugate production were *E. coli* DH5α and CLM24 (Table 1). For efficacy studies, mice were challenged with *F. tularensis* subsp. *holarctica* strain HN63. The bacterium was cultured on blood cysteine glucose agar plates (supplemented with 10 ml of 10% (wt/vol) histidine per litre) at 37° C. for 18 hours.

For vaccination of rats with LVS, Lot 4, bacteria were inoculated onto blood cysteine glucose agar (BCGA) and incubated at 37° C. for 48 h. Bacterial growth was recovered from the agar and re-suspended in phosphate buffered saline (PBS), and the $OD_{600}$ adjusted to 0.14. The suspension was serially diluted ten-fold to the desired concentration for immunisation.

For challenge studies, *F. tularensis* Schu S4 was inoculated onto BCGA and incubated at 37° C. for 24 h. Growth was recovered from agar, re-suspended in PBS and the $OD_{600}$ adjusted to 0.1. One ml of this suspension was inoculated into 100 ml modified cysteine partial hydrolysate (MCPH) broth with 4% glucose and incubated with shaking at 180 rpm, at 37° C. for 48 h. $OD_{600}$ of the culture was adjusted to 0.1 in PBS, and serially diluted to the desired concentration for aerosol challenge.

To determine bacterial load in organs, organs were weighed, then homogenised through a 40 μm cell sieve, serially diluted in PBS, and plated onto BCGA.

Cloning, Sequencing and Expression of the *F. tularensis* O-Antigen Coding Region DNA was prepared from the *F. tularensis* subsp. *tularensis* strain SchuS4 by phenol extraction as described by Karlsson et al. (2000). The O-antigen coding region was amplified using the primers FTfragment2rev (5'-GGATCATTAATAGCTAAATGTAGTGCTG-3'; SEQ ID NO:30) and Oant1ftfwd (5'-TTTTGAATTCTACAGGCTGTCAATGGAGAATG-3'; SEQ ID NO:31) using the following cycling conditions: 94° C., 15 sec, 55° C., 15 sec, 68° C., 20 min; 35 cycles using Accuprime TaqHifi (Invitrogen U.K.). This was cloned into the TA cloning vector pGEM-T Easy to generate the vector pGAB1. The plasmid pGAB1 was digested with EcoRI and the insert was subcloned into the vector pLAFR to generate the construct pGAB2.

Immunofluorescence Imaging of *E. coli* Cells Carrying *F. tularensis* O Antigen Coding Region Immunofluorescence was carried out as previously described [17] with the modification that the IgG2a mouse monoclonal antibody FB11 was used to detect *F. tularensis* O antigen (1 μl/ml in 5% (v/v) FCS/PBS).

Bacterial Strains and Plasmid Construction

*Escherichia coli* CLM24 (17) was used as the host strain for protein expression and glycoconjugate production. CLM24 (a ligase negative strain) was stably transformed with the plasmid pGab2 (24), a construct created from insertion of the *F. tularensis* subspecies *tularensis* strain SchuS4 O-antigen into the low copy number expression plasmid pLAFR (25). pGab2 is tetracycline-selectable and constitutively expressed. Following confirmation of the expression of the *F. tularensis* O-antigen, the resulting strain was then transformed with the plasmid CLM24 contained a plasmid encoded *C. jejuni* PglB, pGVXN114, which expresses the *C. jejuni* glycotransferase pglB Finally, the resulting strain was transformed with the plasmid pGVXN150:GT-ExoA, creating a three plasmid system for production of the glycoconjugate. The GT-ExoA construct was engineered to expressed a modified version of *P. aeruginosa* Exotoxin A that was synthesized by Celtek Bioscience, LLC in the vector pGH and closed into a vector derived from pEC415 using the restriction enzymes NheI and EcoRI (NEB). The synthesized protein contains two internal modifications that allow glycosylation of the protein by PglB (24), as well as containing four N-glycosylation sequons at the N terminal and an additional 4 at the C terminals glycotags. In addition, a hexa-histidine tag was added to the C-terminus of the protein to facilitate putification and an and an *E. coli* DsbA signal peptide was added to the N-terminal sequences enabling Sec-dependent secretion to the periplasm. pGVXN150: GT-ExoA is ampicillin resistant and L-(+)-Arabinose inducible. The construct sequence was then confirmed using Sanger sequences with the primers GTExoA NF (GCGCTGGCTGGTTTAGTTT, SEQ ID NO 32), GTExoA NR (CGCATTCGTTCCAGAGGT, SEQ ID NO 33), GTExoA CF (GACAAGGAACAGGCGATCAG, Seq ID NO 34) and GTExoA CR (TGGTGATGATGGTGATGGTC, SEQ ID NO 35).

Culture and Glycoprotein Expression Conditions

For all experiments, *E. coli* CLM24 was cultured in Luria-Bertani (LB) broth (Fisher Scientific) supplemented with appropriate antibiotics in the following concentrations: ampicillin 100 μg/mL, tetracycline 20 μg/mL, and spectinomycin 80 μg/mL. The addition of manganese chloride at the time of protein and PglB induction was at a final concentration of 4 mM, and made up as a 1 M stock fresh prior to each experiment. Cultures were incubated at 37° C. at 110 RPM for 16-20 hrs for large-scale preparation. For three plasmid system glycoconjugate production, an overnight LB culture of *E. coli* CLM24 harbouring p114, pGvn150:GT-ExoA and pGab2 was sub-cultured in a 1:10 dilution of LB broth (Fisher Scientific) with antibiotics, and grown to mid log phase. pGVXN150:GT-ExoA was induced by addition of 0.2% L-(+)-Arabinose (Sigma), and *C. jejuni* PglB induced with 1 mM IPTG, followed by incubation for an initial 4 hours. Another addition of 0.4% L-(+)-Arabinose was then added and cultures were incubated overnight.

Production and Purification of Glycoconjugate Vaccine

*E. coli* CLM24 carrying the vectors pGAB2, pGVXN114 and pGVXN150 was grown for 16 h in 200 mL LB broth at 37° C., 180 rpm. This was used to inoculate 1.8 L of LB broth and further incubated at 110 r.p.m. 37° C. to an OD.600 nm reading of 0.4 to 0.6. L-(+)-arabinose was then added to a final concentration of 0.2% w/v and IPTG to a final concentration of 1 mM to induce expression of ExoA and Cj PglB respectively; At this point in time manganese chloride at a final concentration of 4 mM was also added. Following 5 hours of incubation, 0.2% w/v L-(+)-arabinose was added again and the culture left to incubate overnight.

Cells were harvested by centrifugation at 5300 g for 30 min, and pelleted cells were then resuspended in an ice cold lysis solution composed of 50 mM $NaH_2PO_4$, 300 mM NaCl, 10 mM imidazole, pH 8.0 (adjusted with 5 M NaOH) supplemented with 1 mg/ml lysozyme and 1 μl/ml Benzonase nuclease (Novagen). Then, cells were subjected to five rounds of lysis using a pre-chilled Stansted High Pressure Cell Disruptor (Stansted Fluid Homogenizer) under ~60,000 psi in continuous mode. Cell debris was removed by centrifugation at 10,000 r.p.m. for 60 m, the supernatant was collected The resulting supernatant was kept on ice while being loaded onto a GE Healthcare HIS trap HP 1 mL column. Then, the column was washed in buffer containing 50.0 mM $NaH_2PO_4$; 300 mM $NaCl_2$; 20 mM imidazole lysis while attached to an AKTA purifier. Material was eluted and collected in 1 mL fractions with an imidazole gradient of 30-500 mM elution buffer that also contained 20% v/v glycerol and 5% w/v glucose. The collected fractions were then visualised by Western blot and the most glycosylated *F. tularensis* carrier proteins conjugated to *F. tularensis* O-antigen were chosen for pooling and buffer exchange (using VivaSpin 2 (VivaProducts) into PBS 20 v/v % glycerol, prior to quantification with a BCA Protein Assay Kit (Pierce Biotechnology, USA).

This generated a typical yield of 2-3.5 mg/ml of glycoconjugate per 2 L of *E. coli* culture.

The same techniques were used for the generation of the 'sham' *C. jejuni* heptasaccharide ExoA glycoconjugate encoded by pACYCpgl [18].

Using the *E. coli* Chromosomally Inserted Strain CLM 24 CedAPglB:

*Escherichia coli* strain CLM24 with a chromosomally inserted copy of pglB were grown in Luria-Bertani (LB) broth at 37° C., with shaking. Antibiotics were used at the following concentrations: tetracycline 20 μg $ml^{-1}$ and ampicillin 100 μg $ml^{-1}$. Tetracycline was used to maintain the plasmid pGAB2 coding for *Francisella tularensis* O antigen and ampicillin was used to maintain the plasmid coding for the acceptor carrier protein.

*E. coli* cells were grown for 16 h in 200 ml LB broth at 37° C., with shaking. This was used to inoculate 1.8 l of LB broth and further incubated with shaking at 37° C. until an $OD_{600}$ reading of 0.4-0.6 was reached. At this point L-(+)-arabinose was added to a final concentration of 0.2% w/v and IPTG to a final concentration of 1 mM to induce expression of the acceptor protein and pglB, respectively; after another 5 h of incubation, 0.2% w/v L-(+)-arabinose was added again and the culture left to incubate overnight.

Cells were harvested by centrifugation at 5300×g for 30 min, and pelleted cells were incubated at room temperature for 30 min in a lysis solution composed of 10× BugBuster protein extraction reagent (Novagen) diluted to 1× in 50 mM $NaH_2PO_4$, 300 mM NaCl, 10 mM imidazole, pH 8.0 supplemented with 0.1 percent Tween, 1 mg $ml^{-1}$ lysozyme and 1 μl $ml^{-1}$ Benzonase nuclease (Novagen). Cell debris was removed by centrifugation at 7840 g for 30 min, the supernatant was collected and 1 ml Ni-NTA agarose (QIAGEN) was added to the supernatant. The slurry-lysate was incubated for 1 h at 4° C. with shaking then loaded into 10 ml polypropylene columns (Thermo Scientific). His-tagged ExoA was purified by the addition of an elution buffer according to manufacturer's instructions (QIA expressionist, QIAGEN) containing 250 mM imidazole with the addition of 20 percent glycerol and 5 percent glucose.

Alternatively cells were grown in LB agar plates containing tetracycline, ampicillin, IPTG to a final concentration of 50 μM and L-(+)-arabinose to a final concentration of 0.2% for 16 h at 37° C. Cells were subsequently harvested by scraping and protein purified as indicated above.

Immunoblot Analysis

To verify transfer and presence of the *F. tularensis* O antigen, samples were analysed by western blotting. *E. coli* cells were grown o/n in 10 ml LB broth and diluted to an O.D.600 nm of 1.0. Cells were centrifuged at 13,000 r.p.m. for 10 min, supernatant was removed and cells were resuspended in 100 μl Laemmli buffer and lysed by boiling for 10 min before analysis by western blotting or silver staining. Mouse anti *F. tularensis* O-antigen monoclonal antibody FB011 (AbCam U.K.) was used at a dilution of 1:1,000, rabbit anti HIS monoclonal antibody was used to detect ExoA at a dilution of 1:10,000 (AbCam U.K.). Secondary antibodies used were goat anti mouse IRDye680 and IRDye800 conjugates used at 1:5000 dilutions. Signal detection was undertaken using the Odyssey® LI-COR detection system (LI_COR Biosciences GmbH).

Cytokine Response Analysis

Spleen supernatants were assessed using mouse inflammatory cytometric bead array kit (CBA-BD biosciences) for IL-10, IL-12p70, IFN-γ, IL-6, TNF-α, and MCP-1. Samples were incubated with the combined capture bead cocktail, and incubated for 1 h at room temperature. Following incubation, PE detection antibodies were added and incubated for a further 1 h. Samples were then washed and resuspended in FACS buffer. Cytokine concentrations were measured via quantification of PE fluorescence of samples in reference to a standard curve.

BALB/c Mouse Challenge Studies

Female Balb/C mice were obtained from Charles River Laboratories (Kent, U.K.) at 6-8 weeks of age. The pilot study was done in groups of 10 mice immunised with either 0.5 μg *F. tularensis* LPS, 0.5 μg *F. tularensis* glycoconjugate, 0.5 μg *F. tularensis* glycoconjugate+SAS, 0.5 μg 'sham' glycoconjugate+SAS, 0.5 μg 'sham' glycoconjugate or SAS only. One group of mice were left untreated as challenge efficacy controls. Immunisations occurred on days 0, 14 and 28 via intra-peritoneal (IP) route. Mice were challenged 35 days post-immunisation with 100 CFU of *F. tularensis* strain HN63 by the IP route, delivered in 0.1 ml. Subsequent experiments used the same schedule with 15 mice per group and doses of 10 μg of material per immunisation. Four weeks following final vaccination 5 mice from each group were tail bled to obtain sera for antibody analysis and culled at day 3 post-infection with spleens harvested to analyse bacterial load and cytokine response. For the enumeration of bacteria, spleen samples were homogenized in 2 ml of PBS through 40 μm cell sieves (BD Biosciences) and 100 μl aliquots were plated onto BCGA plates. *F. tularensis* LPS-specific IgM and total IgG levels were determined by ELISA as previously described [19]. All work was performed under the regulations of the Home Office Scientific Procedures Act (1986).

Statistical Analysis

Statistical analyses were performed using the program PASW (SPSS release 18.0). Survival data was analysed by pair-wise Log Rank test stratified by experiment. Cytokine and bacterial load data were analysed using univariate general linear models, using Bonferroni's post tests to further clarify significant differences.

Production and Purification of Glycoconjugate Vaccine

*E. coli* CLM24 carrying the vectors pGAB2, pGVXN114 and pGVXN150 was grown for 16 h in 200 mL LB broth at 37° C., 180 rpm. This was used to inoculate 1.8 L of LB broth and further incubated at 110 rpm. 37° C. until an O.D600 reading of 0.4 to 0.6 was reached. At this point L-(+)-arabinose was added to a final concentration of 0.2% and IPTG to a final concentration of 1 mM to induce expression of exoA and CjpglB respectively; after another 5 hours of incubation, 0.2% w/v L-(+)-arabinose was added again and the culture left to incubate o/n.

Cells were harvested by centrifugation at 6,000 rpm. for 30 m, and pelleted cells were incubated at room temperature for 30 m in a lysis solution composed of 10×BugBuster protein extraction reagent (Novagen) diluted to 1× in 50 mM NaH2PO4, 300 mM NaCl, 10 mM imidazole, pH 8.0 supplemented with 0.1% Tween, 1 mg/ml lysozyme and 1 μl/ml Benzonase nuclease (Novagen). Cell debris was removed by centrifugation at 10,000 r.p.m. for 30 m, the supernatant was collected and 1 ml Ni-NTA agarose (QIAgen) was added to the supernatant. The slurry-lysate was incubated for 1 h at 4° C. with shaking then loaded into 10 ml polypropylene columns (Thermo scientific). His tagged ExoA was purified by the addition of an elution buffer according to manufacturer's instructions (QIA expressionist, QIAGEN) containing 250 mM imidazole with the addition of 20% w/v glycerol and 5% w/v glucose. Protein yields were estimated using a bicinchonic acid assay kit according to manufacturer's instructions (Pierce® Biotechnology BCA protein Assay Kit, U.S.A.).

For large-scale protein purification, material was isolated using GE Healthcare HIS trap columns and an AKTA purifier with an imidazole gradient of 30 mM to 500 mM. The collected fraction containing ExoA glycosylated with *F. tularensis* O-antigen was further purified using a resource Q anionic exchange column (GE Healthcare) with a NaCl gradient from 0 to 500 mM in 20 mM TrisHCl pH 8.0. This generated a typical yield of 2-3 mg/ml of glycoconjugate per 2 L of *E. coli* culture.

The same techniques were used for the generation of the 'sham' *C. jejuni* heptasaccharide ExoA glycoconjugate. The plasmid coding for this heptasaccharide was pACYCpgl carrying the entire Cjpgl cluster from *C. jejuni* 81116 [1].

Protein Expression

*Escherichia coli* strain CLM24 with a chromosomally inserted copy of pglB were grown in Luria-Bertani (LB) broth at 37° C., with shaking. Antibiotics were used at the following concentrations: tetracycline 20 μg ml-1 and ampicillin 100 μg ml-1. Tetracycline was used to maintain the plasmid pGAB2 coding for *Francisella* O-antigen and ampicillin was used to maintain the plasmid coding for the acceptor carrier protein. Additionally, a final concentration of 4 mM Manganese chloride was added as an additional co-factor to the cultures.

*E. coli* cells were grown for 16 h in 200 ml LB broth at 37° C., with shaking. This was used to inoculate 1.8 l of LB broth and further incubated with shaking at 37° C. until an OD600 reading of 0.4-0.6 was reached. At this point L-(+)-arabinose was added to a final concentration of 0.2% w/v, 4 mM final concentration of manganese chloride, and IPTG to a final concentration of 1 mM to induce expression of the acceptor protein and pglB, respectively; after another 5 h of incubation, 0.2% w/v L-(+)-arabinose was added again and the culture left to incubate overnight.

Cells were harvested by centrifugation at 5300×g for 30 min, and pelleted cells were incubated at room temperature for 30 min in a lysis solution composed of 10× BugBuster protein extraction reagent (Novagen) diluted to 1× in 50 mM NaH2PO4, 300 mM NaCl, 10 mM imidazole, pH 8.0 supplemented with 0.1 percent Tween, 1 mg ml-1 lysozyme and 1 μl ml-1 Benzonase nuclease (Novagen). Cell debris was removed by centrifugation at 7840 g for 30 min, the supernatant was collected and 1 ml Ni-NTA agarose (QIAGEN) was added to the supernatant. The slurry-lysate was incubated for 1 h at 4° C. with shaking then loaded into 10 ml polypropylene columns (Thermo Scientific). His-tagged ExoA was purified by the addition of an elution buffer according to manufacturer's instructions (QIA expressionist, QIAGEN) containing 250 mM imidazole with the addition of 20 percent glycerol and 5 percent glucose.

Creation of WecA$^-$ *E. coli* Strain

The kanamycin resistance cassette from plasmid pKD4 was amplified using the following primers KnF 5'-GTGAATTTACTGACAGTGAGTACTGATCTCATCAGTATTTTTTTATTCACTGTGTAGGCT GGAGCTGCTTC-3' (SEQ ID NO 28) and KnR 5'-GTAAAACGCAGACTGCGTAGAAATCGTGGTGGCAGCCCCAATTTAACCAACATATGAA TATCCTCCTTAGCTGCAG-3' (SEQ ID NO 12) using accuprime taq hifi (Invitrogen UK) and the following cycling conditions 94° C./30 s, followed by 30 cycles of 94° C./30 s, 56° C./30 s, 68° C./90 s. These primers carry 5' end tails that are homologous to the wecA gene of *Escherichia coli* K-12. The PCR product was digested with DpnI and purified before transforming 1 μg into *E. coli* K 12 carrying, the lambda red helper plasmid pKD20 (Datsenko and Wanner PNAS, One-step inactivation of chromosomal genes in *Escherichia coli* K-12 using PCR products, Jun. 6, 2000 pp. 6640-6645). Bacteria were grown on LB agar plates containing 10 mM L-arabinose to induce rec recombinase expression for 48 hrs prior to plating on kanamycin plates. wecA gene deletions were detected by gene specific PCR and resistance to kanamycin.

Animals

Animals were kept in accordance with the Animals (Scientific Procedures) Act 1986. Codes of Practice for the Housing and Care of Animals used in Scientific Procedures 1989. Following challenge with *F. tularensis*, all animals were handled under UK Advisory Committee on Dangerous Pathogens animal containment level 3 conditions within a half-suit isolator compliant with British Standard BS5726.

Female Fischer 344 rats were obtained from Harlan, UK. Rats were implanted with biotherm microchips sub-cutaneously.

Rats were vaccinated with LVS in PBS via the sub-cutaneous (s.c.) route. Rats were vaccinated with 10 μg glycoconjugate in 100 μl PBS via the s.c. or intra-peritoneal route 3 times, 2 weeks apart. Aerosol challenge with *F. tularensis* Schu S4 occurred five weeks following final vaccination.

Following challenge, animals were observed twice daily, and signs of disease and sub-cutaneous temperature recorded. Disease signs were assigned a score, and a cumulative score for disease observed was calculated. Animals were weighed once daily. Weight data was analysed using IBM SPSS V21.0. Weight data was taken as the differential weight from 1 day prior to challenge. Data was found to fit the normal, Gaussian distribution using Q-Q plots (not shown). The data was then analysed using a repeated measures General Linear Model. Validity of the data for this test was further established using Levene's tests for unequal variance (not shown). Individual comparisons, pairwise and dependant or independent of time points, were performed using the Bonferroni's correction. Humane end points of more than 15% weight loss, and/or sub-cutaneous temperature reading of less than 33° C. were used. Animals underwent Schedule 1 euthanasia with i.p. administered euthatal.

Aerosol Challenge

Rats were exposed to an aerosol of *F. tularensis* SchuS4 by the inhalational route in a nose-only exposure unit (DstI, in house) utilising a 6-jet Collison atomiser (DstI, in house) attached to a contained Henderson Piccolo arrangement to condition the aerosol to 50% (±5%) relative humidity, and controlled by the (AeroMP) Aerosol Management Platform aerosol system (Biaera Technologies L.L.C.). The animals were exposed to the aerosolised bacteria for 10 minutes, with impingement of the aerosol cloud sampled at the midway point of challenge into PBS via an All-Glass Impinger (AGI-30; Ace Glass, Vineland, NJ).

Following challenge, the impinged aerosol was enumerated by serial dilution and plating onto BCGA plates. Calculated retained dose was calculated from aerosol concentration (cfu/L of air), using Guyton's formula (27), for minute respiratory volume, and assuming 40% retention of 1-3 μm droplets (26).

Cell Isolation and Culture

Rat spleens were homogenised through a 40 μm sieve using a sterile plunger and colleved into L15 medium. The isolated splenocytes were diluted to $2\times10^6$ cells/ml in medium and cultured in the presence of either medium alone, sonicated LVS whole cells (10 μg/ml, DstI), sonicated Schu S4 whole cells (10 μg/ml, DstI), purified ExoA (5 μg/ml, LSHTM) or Concanavalin-A (Con-A, 5 μg/ml, Sigma-Aldrich). For cultures of cells from LVS infected or PBS control rats, splenocytes were diluted in L-15 medium (Life Technologies) supplemented with 10% Foetal Bovine Serum (Sigma), non-essential amino acids (Life Technologies), 2-mercaptoethanol (Life Technologies), 100 U/ml penicillin and 100 mg/ml streptomycin sulphate (Life Technologies) and then cultured at 37° C. in the absence of a controlled $CO_2$ environment. For cultures of cells from ExoA vaccinated rats, splenocytes were diluted in RPM11640 medium (Life Technologies), supplemented as described above and then cultured at 37° C. with 5% $CO_2$.

Measurement of IFNγ by Enzyme Linked Immunosorbent Assay (ELISA). Splenocytes ($2\times10^5$ per assay well) were cultured in duplicate in the presence of antigen for 72 hours and supernatants harvested and stored at −20° C. prior to use. The expression of IFNγ was determined in plasma supernatants using a commercial rat IFNγ ELISA kit (Mabtech) with responses determined by measurement of optical density at 450 nm ($OD_{450\ nm}$). For reporting, the $OD_{450\ nm}$ results were normalised by transformation into units of ρg/ml by generating a standard curve using recombinant rat IFNγ, as supplied with the assay kit.

Flow cytometry. Splenocytes ($2\times10^6$ cells per assay well) were cultured in the presence of antigen for 20 hours with Brefeldin-A (10 ug/ml, Sigma-Aldrich) added to culture medium for the final 4 hours of the culture. Cells were harvested by centrifugation (300 g/5 mins) and stained using the following anti-rat surface marker antibodies; CD3-Brilliant Violet 421, CD4-FITC (clone OX35, eBioscience) and CD8-PerCP eFluor710 (clone OX8, eBioscience). Cells were stained for 15 minutes at 4° C. in the presence of a fixable yellow (405 nm) cell viability dye (Life Technologies) and then fixed for 16 hours at 4° C. in Cytofix fixation reagent (BD Biosciences). Fixed cells were permeabilised in BD Biosciences Permeabilistation Buffer and then stained intracellularly for 30 minutes at 4° C. using anti-rat antibodies IFNγ-PE (clone DB-1, BD Biosciences) and IL17A-APC (clone eBio17B7, eBioscience). Stained samples were analysed using a FACSCanto II analyser equipped with 405, 488 and 633 nm lasers (BD Biosciences). An example gating strategy for measurement of intracellular expression of IFNγ and IL-17 is given in FIG. 25. Data analysis was performed using FlowJo v10 software (TreeStar, USA). All antibodies were titrated prior to use to ensure optimal staining. Median number of live-singlet lymphocyte cell events on which analyses were performed was 62,598 (±18,724 SD)

ImageStream Staining and Data Capture

500 μl whole rat blood was blocked with 5 μl anti-rat CD32 antibody (BD Pharmingen Cat No: 550271), incubated for 5 minutes at room temperature (~23° C.). Following blocking 40 μl anti-rat CD45-FITC (BD Pharmingen Cat No: 554877), 50 μl anti-rat CD3-APC (BD Pharmingen, Cat No: 557030) and 120 μl 0.5% BSA in PBS were added to the blood sample. Samples were then incubated at 4° C. for 45 minutes. Blood samples were subsequently centrifuges at 300×g for 10 minutes and the supernatants removed. 1 ml BD lysis buffer (BD Pharmingen) was added and samples incubated for 10 minutes at room temperature (~23° C.), before being centrifuged at 300×g for 10 minutes. Supernatants were removed and samples were washed and centrifuged again before being re-suspended in 100 μl of 4% paraformaldehyde and stored at 4° C. Samples were counterstained with 3 μM 4',6-diamidino-2-phenylindole (DAPI) 3 minutes before data capture.

Data was collected using an dual camera imagestream X Mk II equipt with a 405 nm laser (set to 2 mW), a 488 nm laser (set to 100 mW) and a 642 nm laser (set to 150 mW). Samples were acquired using Inspire (version 2.0) where a minimum of 20,000 in-focus (Gradient RMS<50) nucleated (Intensity Ch07<$1\times10^4$) were captured per rat. Single stained samples were also created and acquired for the construction of a compensation matrix. This was performed in inspire using the compensation wizard during data capture. Data are generated from a minimum of 4 mice. Statistical analysis was completed using GraphPad Prism version 6.02.

Data validity was first assessed using a Brown-Forsythe test for variance after which a two-way ANOVA was completed with Dunnett's multiple comparisons test was completed.

ELISA for Anti Gt-ExoA Antibody Titre

Plates were coated with 5 μg/ml Gt-ExoA in PBS and, 100 μl per well, and incubated at 4° C. overnight. After blocking with 1% skimmed milk powder in PBS for 2 hours at 37° C., plates were washed three times with 0.05% TWEEN in PBS. Sera was applied to plates at 1:50 and serially diluted 1:2 across the plate, in 1% skimmed milk powder. Bound IgG rat antibody was detected using anti-rat antibody conjugated to HRP at 1:2000 in PBS, and developed using 10 mM 2,2'-azino-bis(3-ethylbenzothiazoline-6-sulphonic acid) in citrate buffer, with 0.01% $H_2O_2$. OD was measured at 414 nm. Antibody titre was defined as the reciprocal of the highest dilution of serum that had a mean OD value at least 3 standard deviations higher than the mean OD of non-vaccinated serum.

EXAMPLE 1

Fischer 344 Rats are Susceptible to <10 CFU *F. tularensis* Schu S4 Via the Aerosol Route Groups of 5 rats were challenged with a range of doses of *Francisella tularensis* Schu S4 via the aerosol route, from approximately 9 cfu to $3.15\times10^4$ cfu. To determine bacterial dissemination following challenge, groups of five rats from each dose group were sacrificed at 7 days post infection. At this time, all rats challenged with $3.15\times10^4$ cfu, and 3 of 5 rats challenged with $2.22\times10^3$ had already succumbed to infection. At 7 days post-infection, all infected animals had highly colonised lungs, containing greater than $1\times10^6$ cfu/g of lung tissue. The most heavily colonised lungs, from animals challenged with $2.22\times10^3$ contained up to $1\times10^8$ cfu/g. Bacteria had disseminated from lungs to liver and spleen in all infected rats. All rat spleens and livers at 7 days post infection contained greater than $1\times10^4$ cfu/g tissue Schu S4 bacteria.

Figure 1:
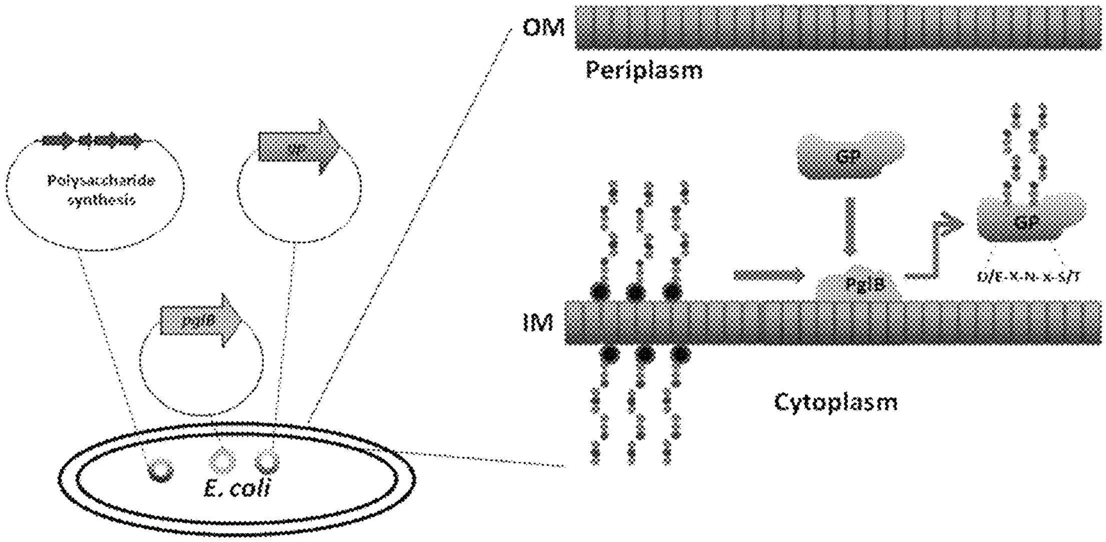
FIG. 1: Principles of Protein Glycan Coupling Technology in *E. coli*. An *E. coli* cell is transformed with three plasmids to generate the cloned glycoconjugate protein (GP). The plasmids encode the oligosaccharyltransferase PglB, the biosynthetic polysaccharide locus and the carrier protein. The polysaccharide is synthesised on an undecaprenol pyrophosphate lipid anchor (•) within the cytoplasm, this is transferred to the periplasmic compartment where PglB recognises the lipid link reducing end sugar and transfers the polysaccharide en bloc onto an acceptor sequon (D/E-X-N-X-S/T) on the carrier protein to produce the glycoconjugate protein (GP). IM, inner membrane; OM, outer membrane.
Figure 2:
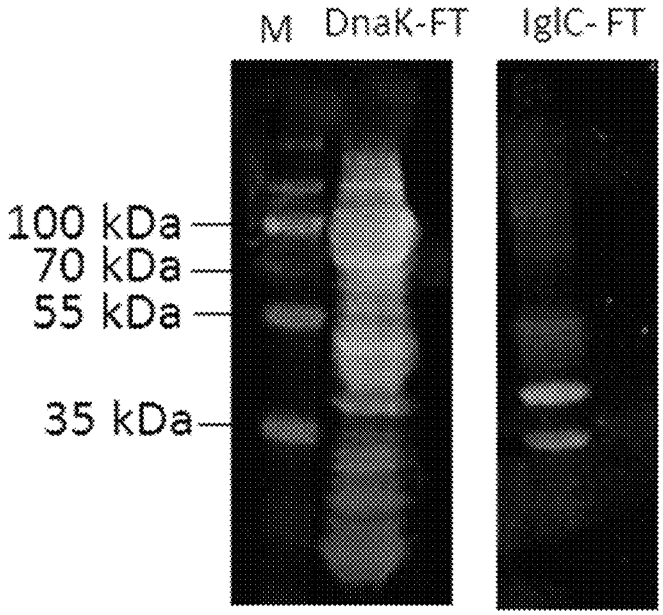
FIG. 2: Western blot of glycoconjugates DnaK-FT and IglC indicate these *F. tularensis* proteins are glycosylated by *C. jejuni* PglB with the *F. tularensis* O-antigen. These are produced in large quantity indicating the suitability of DnaK and IglC as protective vaccine candidates. M: protein marker, DnaK and IglC glycoconjugates were prepared in large scale 2 L batch culture and purified. Western blot indicates protein (green) and *F. tularensis* O-antigen glycan (red) both present in samples.
Figure 19B:
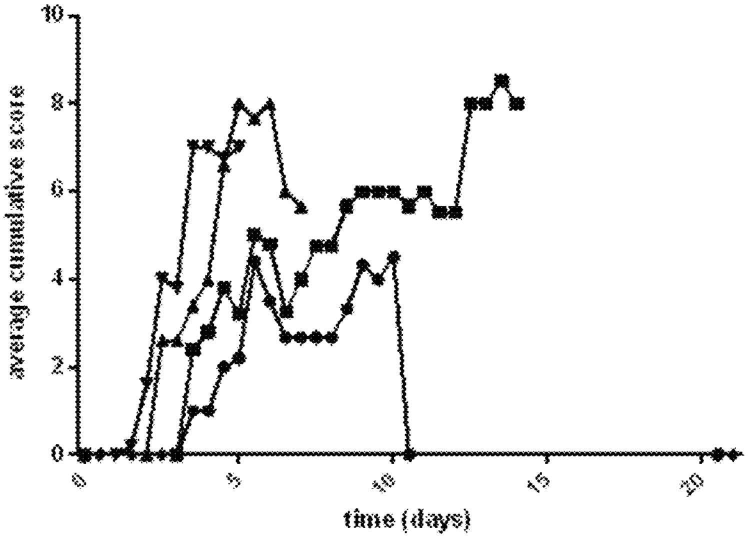
Figure 19C:
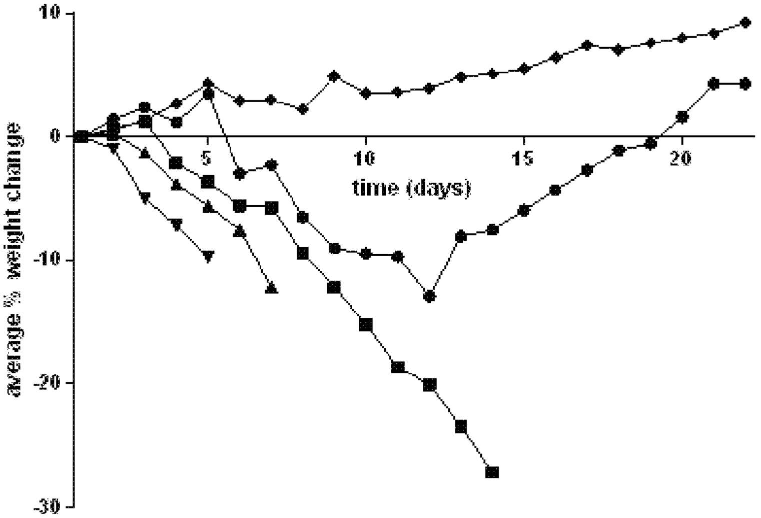

All rats challenged with $2.94\times10^2$ to $3.15\times10^4$ cfu rats succumbed to infection within 14 days of challenge (FIG. 19A). Of rats challenged with CFU of *F. tularensis*, only 1 animal of 5 survived to the end of experiment at 21 days post infection. During the recovery of this animal, its disease signs resolved and some weight was recovered. The MLD is therefore estimated to be less than 9 cfu via the aerosol route. All infected rats underwent a febrile stage, with subcutaneous temperatures which were raised at least 1.5° C. above their baseline temperature (data not shown). All infected rats showed severe signs of disease. Rats first became ruffled, and developed eye problems including secretion of porphyrin and ptosis of the eyelids until their eyes were completely closed, followed by hunched posture alongside rapid breathing. Rats became more lethargic and less responsive to stimuli over the course of disease (FIG. 19B). All infected rats lost weight, in a dose dependent manner (FIG. 19C). Rats which received the highest challenge: $3.15\times10^4$ cfu, rapidly lost between 7 and 10 percent of their body weight within 5 days of challenge. Those rats which received a lower challenge all lost at least 10 percent of their starting weight, and in some cases more than 25 percent of body weight, but over a greater length of time.

EXAMPLE 2

LVS Disseminates to Lungs, Liver, and Spleen Following Challenge, Inducing Expansion of Neutrophil and Macrophage Populations in the Blood.

To determine dissemination and clearance of bacteria, and determine host cell responses to LVS infection, groups of five rats were vaccinated with $5.56\times10^5$ or $5.56\times10^7$ CFU of LVS sub-cutaneously. Following vaccination, rats were sacrificed at 3, 7 and 21 days post-vaccination to determine bacterial dissemination and clearance. There was no significant difference in colonisation of organs between rats vaccinated at the 2 different doses. At 3 days post-vaccination, all rats were colonised in the liver and spleen, whilst lungs had low numbers of detectable bacteria. At 7 days, no bacteria could be detected in lungs and liver of vaccinated rats, whilst spleens were still colonised. No bacteria were detected in lungs, liver or spleen at 21 days post infection.

Figure 20A:
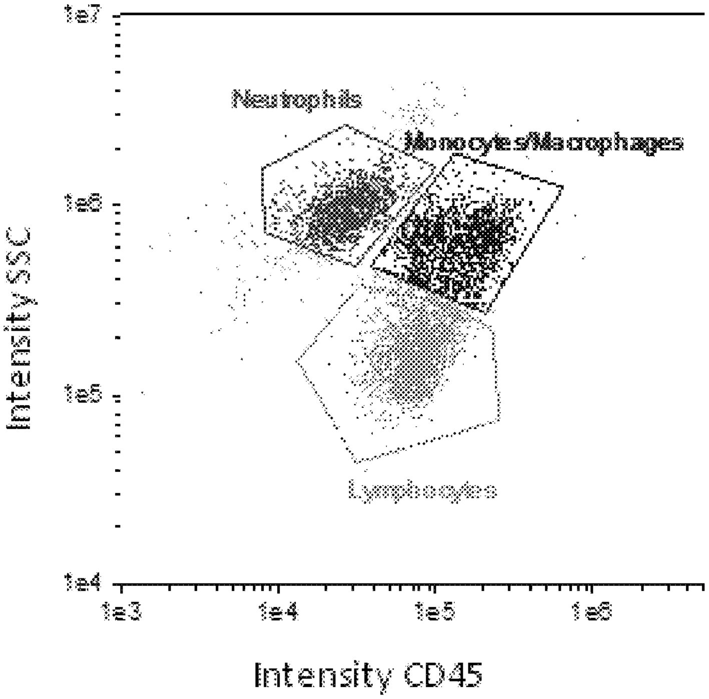
FIGS. 20A-20C: Effect of rat white blood cell counts during vaccination with Ft LVS Imaging flow cytometry was used to assess the effect of LVS vaccination on the rat immune response. Whole rat blood was labelled with CD45, CD3 and counter stained with DAPI for nuclear visualisation. Quantification of lymphocytes, monocytes/macrophages and neutrophils was achieved using CD45 vs side scatter (SSC) (FIG. 20A). Cell we gated as follows SSC high CD45 low for neutrophils, SSC low CD45 high for lymphocytes and SSC medium CD45 high for monocytes/macrophages (FIG. 20B). Data (FIG. 20C) shows the % gated of each cell type and each rat over the 21 day time course. Data shows a decrease in lymphocytes at day with returning to control levels at day 7 and 21. It also shows increased in neutrophils at day 3 returning to normal level at days 7 and 21. A significant increase in monocytes/macrophages is only observed in the LVS $10^7$ group at day 3 again this returns to normal levels by day 7 and 21.
Figure 20B:
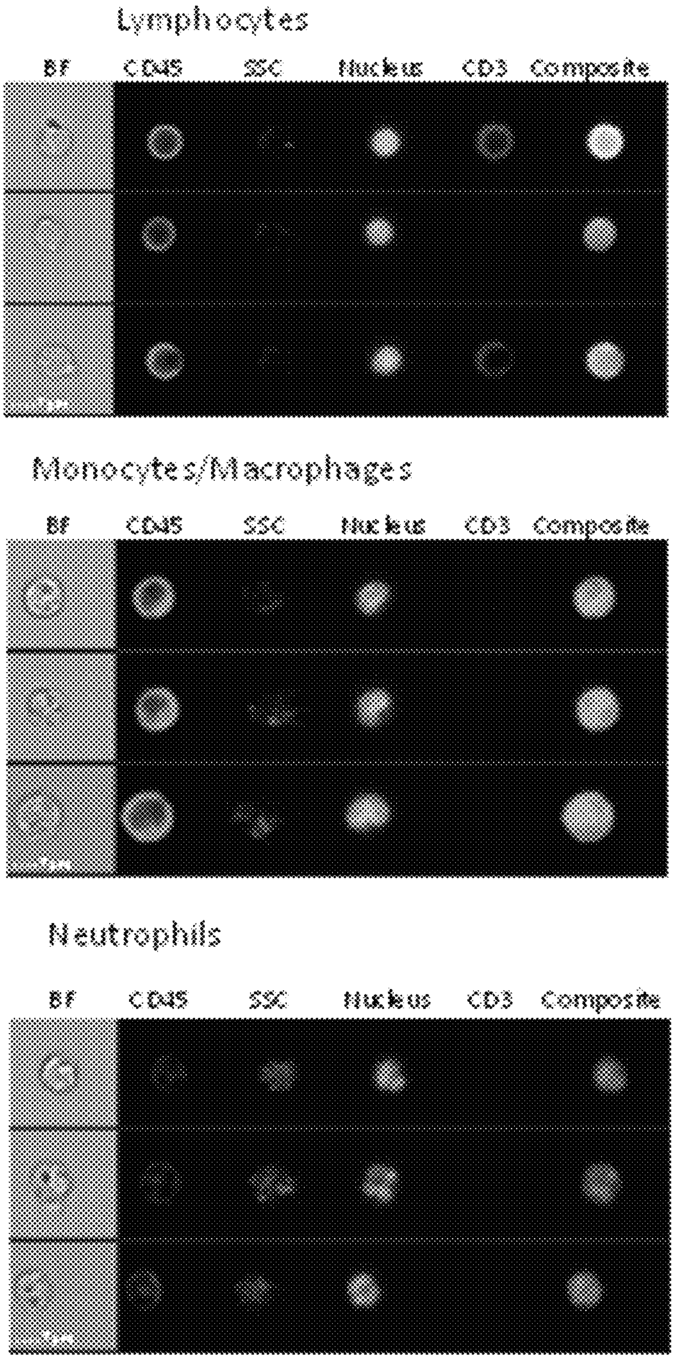
Figure 20C:
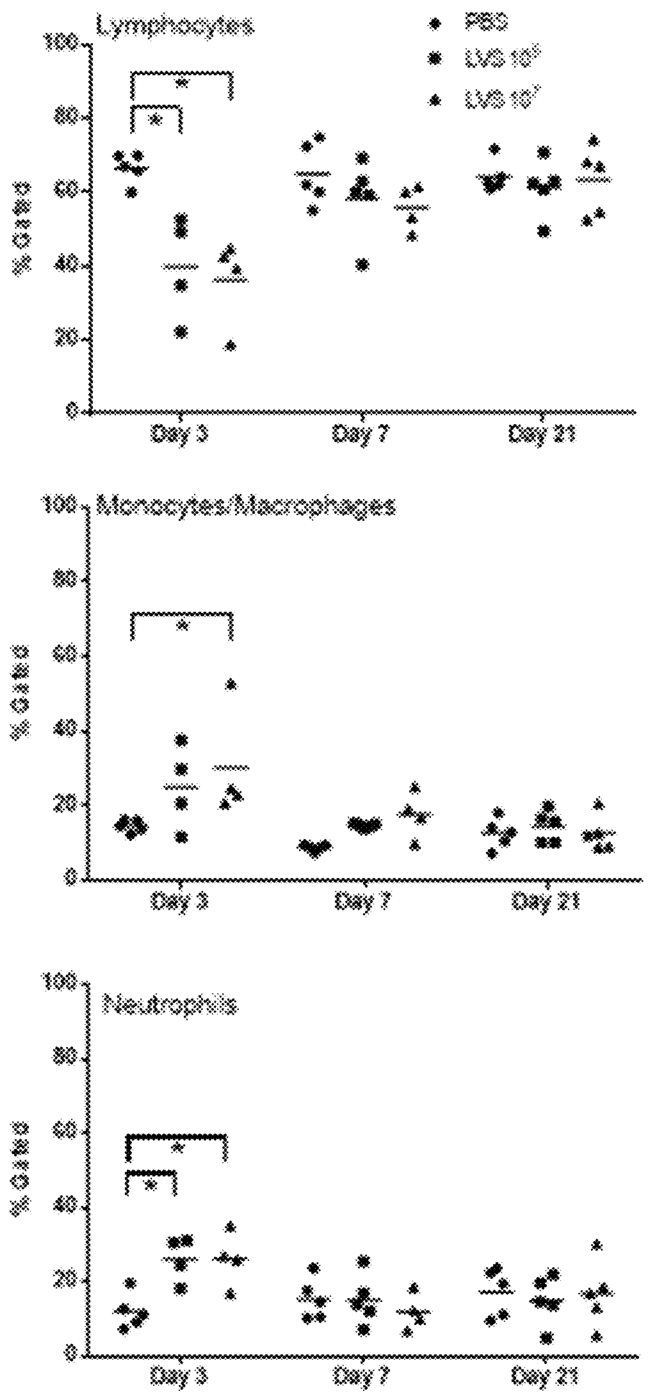

Rat immune cells in whole blood were quantified using the ImageStream X MkII. Cell types were differentiated by CD45 intensity verses side scatter intensity identifying three distinct populations namely, lymphocytes, monocytes/macrophages and neutrophils (FIGS. 20A and B). There was a significant decrease in lymphocyte counts in rats challenged with both $10^5$ and $10^7$ LVS at day 3 post vaccination ($p<0.01$), with a return to baseline at day 7 and day 21. This is mirrored in the neutrophil count, with a significant increase in neutrophils at day 3 in both dose groups decreasing back to baseline at day 7 and 21. Monocyte/macrophage numbers in rats challenged with $10^7$ LVS were significantly increased at day 3, returning to baseline levels at days 7 and 21.

EXAMPLE 3

LVS Induces T Cell Memory Response Characterised by IFNγ and IL-17 Expression on Re-Stimulation To determine the splenocyte re-stimulation response following LVS vaccination, 5 rats were sacrificed at day 21 and day 35 post-vaccination and splenocytes were harvested from rat spleens. IFNγ secretion by splenocytes was measured following re-stimulation with a range of antigens. The absence of responses in the PBS control rats indicates the antigen specific nature of these memory re-call responses, whilst all cells secreted IFNγ in response to the mitogen ConA indicating the cells potential for responding. LVS vaccinated rat splenocytes secreted significantly more IFNγ in response to stimulation with all three *F. tularensis* whole cell antigen preparations than PBS vaccinated rats (FIG. 21).

FIG. 4. Antigen stimulated IFNγ response in LVS infected rats. Splenocytes isolated from rats 21 days following infection with $10^5$ CFU LVS (grey bars), $10^7$ CFU LVS (black bars) or the PBS controls (hashed bars) were cultured in the presence of LVS sonicate, *F. tularensis* sonicate, Con-A or medium and then expression of IFNγ in 72 hour culture supernatants measured by ELISA. IFNγ responses (ρg/ml) are presented as mean response for each group (n=5)±SEM.

Further investigation of memory response to LVS was investigated by measurement of intracellular expression of IFNγ and IL-17 following antigen stimulation, 21 days post-infection with LVS. LVS infection resulted in the induction of both CD4 and CD8 effector memory responses, as demonstrated by antigen-specific IFNγ responses by these cell phenotypes (FIG. 22). Additionally, CD4+ memory cells that express IL-17 upon antigen stimulation are also generated by LVS infection in the rats (FIG. 22).

EXAMPLE 4

Glycoconjugate Induces Antigen Specific Memory Response and IgG Antibody

Similarly to LVS vaccinated rats, splenocytes were isolated from glycoconjugate vaccinated rats at 35 days post final vaccination. Cells were re-stimulated both with crude antigen preparations, and recombinant ExoA protein for 72 hours. IFNγ secretion following re-stimulation of splenocytes from LVS challenged rats with crude *F. tularensis* antigens, corroborates intracellular IFNγ expression previously described (FIG. 23). In addition, the measurement of ExoA antigen specific IFNγ responses only in Gt-ExoA vaccinated rats confirmed the recognition of the Gt-ExoA conjugate by the cell mediated compartment of the immune system (FIG. 23). Serum from Gt-ExoA vaccinated rats and their appropriate MF59 only controls were measured for IgG recognition of Gt ExoA. Sera from MF59 only controls showed no appreciable binding to Gt-ExoA. IgG titres from rats vaccinated with Gt-ExoA by the i.p. route were 1:204800, and by the s.c. route 1:102400, demonstrating an antigen specific IgG response to vaccine.

EXAMPLE 5

LVS and *F. tularensis* O-Antigen+Exoprotein A Glycoconjugate Both Protect Against Pulmonary Tularemia Rats were vaccinated with $5.39\times10^7$ LVS via the s.c. route, and glyconojugate by both the s.c. and i.p. route. Five weeks later the animals were challenged with an average $5.48\times10^2$ *F. tularensis* Schu S4. All vaccinated rats survived 21 days post aerosol challenge (FIG. 24A). Of five rats vaccinated with MF59 alone via the i.p route, one rat survived to 21 days post infection (FIG. 24A). Three of five rats vaccinated with MF59 alone via the s.c. route survived to 21 days post infection, which is not significantly different from rats vaccinated with glycoconjugate via the s.c. route (FIG. 24A).

Rats vaccinated with Gt-ExoA by either route, or with LVS did not become febrile (data not shown) and showed no signs of disease (FIG. 24B). Comparatively, rats vaccinated with PBS s.c. and adjuvant only via i.p and s.c. routes all become febrile (data not shown), and all showed severe signs of disease (FIG. 24B)

Weight change in rats after challenge, compared to 1 day before challenge, was shown to be significantly different over time between all groups of vaccinated rats and their relevant controls (FIG. 24C). Weight change between rats vaccinated with Gt-ExoA by the s.c. route and the relevant control rats, vaccinated with MF59 alone by the s.c. route, significantly diverged on day 2 after challenge FIG. 24D)

(p<0.05). Weight change in rats vaccinated with LVS or with Gt-ExoA via the i.p. route significantly diverged from their apposite controls on day 4 (FIG. 24C and FIG. 24E) (p<0.005, p<0.0005 respectively).

The surviving control rats all resolved signs of disease and had recovered some weight by 21 days following infection. *F. tularensis* was not detected in lungs, liver or spleen of LVS and glycoconjugate vaccinated rats at 21 days post infection whilst all surviving MF59 only vaccinated rats were colonised with *F. tularensis* in lung, liver and spleen at 21 days post infection.

REFERENCES

1. Shinefield H R, Black S, Ray P, et al. Safety and immunogenicity of heptavalent pneumococcal CRM197 conjugate vaccine in infants and toddlers. The Pediatric infectious disease journal 1999; 18:757-63.
2. Grijalva C G, Nuorti J P, Arbogast P G, Martin S W, Edwards K M, Griffin M R. Decline in pneumonia admissions after routine childhood immunisation with pneumococcal conjugate vaccine in the USA: a time-series analysis. Lancet 2007; 369:1179-86.
3. Theodoratou E, Johnson S, Jhass A, et al. The effect of *Haemophilus influenzae* type b and pneumococcal conjugate vaccines on childhood pneumonia incidence, severe morbidity and mortality. International journal of epidemiology 2010; 39 Suppl 1:i172-85.
4. Sucher A J, Chahine E B, Nelson M, Sucher B J. Prevnar 13, the new 13-valent pneumococcal conjugate vaccine. The Annals of pharmacotherapy 2011; 45:1516-24.
5. Feldman M F, Wacker M, Hernandez M, et al. Engineering N-linked protein glycosylation with diverse O antigen lipopolysaccharide structures in *Escherichia coli*. Proceedings of the National Academy of Sciences of the United States of America 2005; 102:3016-21.
6. Terra V S, Mills D C, Yates L E, Abouelhadid S, Cuccui J, Wren B W. Recent developments in bacterial protein glycan coupling technology and glycoconjugate vaccine design. Journal of medical microbiology 2012; 61:919-26.
7. Langdon R H, Cuccui J, Wren B W. N-linked glycosylation in bacteria: an unexpected application. Future microbiology 2009; 4:401-12.
8. Dennis D T, Inglesby T V, Henderson D A, et al. Tularemia as a biological weapon: medical and public health management. JAMA: the journal of the American Medical Association 2001; 285:2763-73.
9. Reintjes R, Dedushaj I, Gjini A, et al. Tularemia outbreak investigation in Kosovo: case control and environmental studies. Emerging infectious diseases 2002; 8:69-73.
10. McCrumb F R. Aerosol Infection of Man with *Pasteurella tularensis*. Bacteriological reviews 1961; 25:262-7.
11. Oyston P C, Sjostedt A, Titball R W. Tularaemia: bioterrorism defence renews interest in *Francisella tularensis*. Nature reviews Microbiology 2004; 2:967-78.
12. Fulop M, Manchee R, Titball R. Role of lipopolysaccharide and a major outer membrane protein from *Francisella tularensis* in the induction of immunity against tularemia. Vaccine 1995; 13:1220-5.
13. Weintraub A. Immunology of bacterial polysaccharide antigens. Carbohydrate research 2003; 338:2539-47.
14. Fulop M, Mastroeni P, Green M, Titball R W. Role of antibody to lipopolysaccharide in protection against low- and high-virulence strains of *Francisella tularensis*. Vaccine 2001; 19:4465-72.
15. Conlan J W, Shen H, Webb A, Perry M B. Mice vaccinated with the O-antigen of *Francisella tularensis* LVS lipopolysaccharide conjugated to bovine serum albumin develop varying degrees of protective immunity against systemic or aerosol challenge with virulent type A and type B strains of the pathogen. Vaccine 2002; 20:3465-71.
16. Prior J L, Prior R G, Hitchen P G, et al. Characterization of the O antigen gene cluster and structural analysis of the O antigen of *Francisella tularensis* subsp. *tularensis*. Journal of medical microbiology 2003; 52:845-51.
17. Cuccui J, Milne T S, Harmer N, et al. Characterization of the *Burkholderia pseudomallei* K96243 capsular polysaccharide I coding region. Infection and immunity 2012; 80:1209-21.
18. Wacker M, Linton D, Hitchen P G, et al. N-linked glycosylation in *Campylobacter jejuni* and its functional transfer into *E. coli*. Science 2002; 298:1790-3.
19. Eyles J E, Hartley M G, Laws T R, Oyston P C, Griffin K F, Titball R W. Protection afforded against aerosol challenge by systemic immunisation with inactivated *Francisella tularensis* live vaccine strain (LVS). Microbial pathogenesis 2008; 44:164-8.
20. Ihssen J, Kowarik M, Dilettoso S, Tanner C, Wacker M, Thony-Meyer L. Production of glycoprotein vaccines in *Escherichia coli*. Microbial cell factories 2010; 9:61.
21. Friedman A M, Long S R, Brown S E, Buikema W J, Ausubel F M. Construction of a broad host range cosmid cloning vector and its use in the genetic analysis of *Rhizobium* mutants. Gene 1982; 18:289-96.
22. Pedersen C, Petaja T, Strauss G, et al. Immunization of early adolescent females with human papillomavirus type 16 and 18 L1 virus-like particle vaccine containing AS04 adjuvant. The Journal of adolescent health: official publication of the Society for Adolescent Medicine 2007; 40:564-71.
23. Fisher A C, Haitjema C H, Guarino C, et al. Production of secretory and extracellular N-linked glycoproteins in *Escherichia coli*. Applied and environmental microbiology 2011; 77:871-81.
24. Cuccui J, Thomas R M, Moule M G, D'Elia R V, Laws T R, Mills D C, et al. Exploitation of bacterial N-linked glycosylation to develop a novel recombinant glycoconjugate vaccine against *Francisella tularensis*. Open Biology. 2013; 3.
25. Karlsson J, Prior R G, Williams K, Lindler L, Brown K A, Chatwell N, et al. Sequencing of the *Francisella tularensis* strain Schu 4 genome reveals the shikimate and purine metabolic pathways, targets for the construction of a rationally attenuated auxotrophic vaccine. Microbial and Comparative Genomics. 2000; 5(1):25-39.
26. Harper G J, Morton J D. The respiratory retention of bacterial aerosols—experiments with radioactive spores. Journal of Hygiene. 1953; 51(3):372-85.
27. Guyton A C. Measurement of the respiratory volumes of laboratory animals. American Journal of Physiology. 1947; 150(1):70-7.

The invention claimed is:

1. A vaccine or immunogenic composition, comprising:

a carrier polypeptide comprising at least 95% identity over the full length of the amino acid sequence of SEQ ID NO: 3 and an O-antigen antigenic polysaccharide isolated from *Francisella* crosslinked to the carrier polypeptide, wherein the O-antigen antigenic polysaccharide comprises 4)-α-D-GalNAcAN-(1-4)-α-D-GalNAcAN-(1-3)-β-D-GlcNAc-(1-2)-β-D-Qui4NFm-(1-), and wherein GalNacAN is 2-acetomido-2-deoxy-O-D-galacturonamide, Qui4NFm is 4,6-dideoxy-4-formamido-D-glucose, and the reducing end group GlcNAc is N-acetyl glucosamine.

2. The vaccine or immunogenic composition according to claim 1, wherein the carrier polypeptide comprises at least 96% identity over the full length of the amino acid sequence of SEQ ID NO: 3.

3. The vaccine or immunogenic composition according to claim 1, wherein the carrier polypeptide comprises at least 97% identity over the full length of the amino acid sequence of SEQ ID NO: 3.

4. The vaccine or immunogenic composition according to claim 1, wherein said composition further includes an adjuvant.

5. The vaccine or immunogenic composition according to claim 4, wherein said adjuvant is an aluminium based adjuvant suitable for use in a human subject.

6. A method of preventing a *Francisella* infection, comprising:

administering the vaccine or immunogenic composition of claim 1 to a subject, thereby preventing the *Francisella* infection in the subject.

7. An antigenic polypeptide, comprising:

a carrier polypeptide comprising at least 95% identity over the full length amino acid sequence of SEQ ID NO: 3, and an O-antigen antigenic polysaccharide isolated from *Francisella* crosslinked to the carrier polypeptide;

wherein the O-antigen comprises

4)-α-D-GalNAcAN-(1-4)-α-D-GalNAcAN-(1-3)-β-D-GlcNAc-(1-2)-β-D-Qui4NFm-(1-), and wherein GalNacAN is 2-acetomido-2-deoxy-O-D-galacturonamide, Qui4NFm is 4,6-dideoxy-4-formamido-D-glucose, and the reducing end group GlcNAc is N-acetyl glucosamine.

8. The antigenic polypeptide according to claim 7, wherein the carrier polypeptide comprises at least 96% identity over the full length of the amino acid sequence of SEQ ID NO: 3.

9. A vaccine or immunogenic composition, comprising:

a carrier polypeptide comprising the amino acid sequence of SEQ ID NO: 3, and an O-antigen antigenic polysaccharide isolated from *Francisella* and crosslinked to said carrier polypeptide, wherein the O-antigen is 4)-α-D-GalNAcAN-(1-4)-α-

D-GalNAcAN-(1-3)-β-D-GlcNAc-(1-2)-β-D-Qui4NFm-(1-), wherein GalNacAN is 2-acetomido-2-deoxy-O-D-galacturonamide, Qui4NFm is 4,6-dideoxy-4-formamido-D-glucose, and the reducing end group GlcNAc is N-acetyl glucosamine.

10. The vaccine or immunogenic composition according to claim 9, wherein the composition further includes an adjuvant.

11. The vaccine or immunogenic composition according to claim 10, wherein the adjuvant is an aluminium based adjuvant suitable for use in a human subject.

12. A method of preventing a *Francisella* infection, comprising:

administering the vaccine or immunogenic composition of claim 9 to a subject, thereby preventing the *Francisella* infection in the subject.

13. An antigenic polypeptide, comprising:

a carrier polypeptide comprising the amino acid sequence of SEQ ID NO: 3, and an O-antigen antigenic polysaccharide isolated from *Francisella* and crosslinked to the carrier polypeptide, wherein the O-antigen is 4)-α-D-GalNAcAN-(1-4)-α-D-GalNAcAN-(1-3)-β-D-GlcNAc-(1-2)-β-D-Qui4NFm-(1-), wherein GalNacAN is 2-acetomido-2-deoxy-O-D-galacturonamide, Qui4NFm is 4,6-dideoxy-4-formamido-D-glucose, and the reducing end group GlcNAc is N-acetyl glucosamine.

14. The vaccine or immunogenic composition according to claim 1, wherein the carrier polypeptide comprises at least 98% identity over the full length of the amino acid sequence of SEQ ID NO: 3.

15. The vaccine or immunogenic composition according to claim 1, wherein the carrier polypeptide comprises at least 99% identity over the full length of the amino acid sequence of SEQ ID NO: 3.

16. The antigenic polypeptide according to claim 7, wherein the carrier polypeptide comprises at least 97% identity over the full length of the amino acid sequence of SEQ ID NO: 3.

17. The antigenic polypeptide according to claim 7, wherein the carrier polypeptide comprises at least 98% identity over the full length of the amino acid sequence of SEQ ID NO: 3.

18. The antigenic polypeptide according to claim 7, wherein the carrier polypeptide comprises at least 99% identity over the full length of the amino acid sequence of SEQ ID NO: 3.

* * * * *